US011839550B1

(12) United States Patent
Kellar et al.

(10) Patent No.: US 11,839,550 B1
(45) Date of Patent: Dec. 12, 2023

(54) MACHINE LEARNING BASED JOINT EVALUATION METHOD

(71) Applicant: Little Engine, LLC, Belmont, NC (US)

(72) Inventors: Franz W. Kellar, Gastonia, NC (US); Michael D. Bissette, Belmont, NC (US); Franz Austen Kellar, Gastonia, NC (US)

(73) Assignee: Little Engine, LLC, Belmont, NC (US)

( * ) Notice: Subject to any disclaimer, the term of this patent is extended or adjusted under 35 U.S.C. 154(b) by 0 days.

(21) Appl. No.: 17/851,931

(22) Filed: Jun. 28, 2022

Related U.S. Application Data

(60) Provisional application No. 63/349,714, filed on Jun. 7, 2022, provisional application No. 63/349,719, filed on Jun. 7, 2022.

(51) Int. Cl.
*A61B 34/10* (2016.01)
*A61F 2/38* (2006.01)
(Continued)

(52) U.S. Cl.
CPC ............ *A61F 2/3854* (2013.01); *A61B 34/10* (2016.02); *A61B 34/20* (2016.02); *A61B 34/25* (2016.02);
(Continued)

(58) Field of Classification Search
CPC .............. A61B 34/10; A61B 2034/101; A61B 2034/104; A61B 2034/105; A61B 2034/107; A61B 2034/108
See application file for complete search history.

(56) References Cited

U.S. PATENT DOCUMENTS

| 5,713,897 A | 2/1998 | Goble et al. |
| 5,935,129 A | 8/1999 | McDevitt et al. |

(Continued)

FOREIGN PATENT DOCUMENTS

| WO | WO-2007126917 A2 * | 11/2007 | ........... A61F 2/4684 |
| WO | 2014188184 | 11/2014 | |

(Continued)

OTHER PUBLICATIONS

Attune Knee System, CAS Surgical Technique, Published 2014, accessed at "http://synthes.vo.llnwd.net/o16/LLNWMB8/US%20Mobile/Synthes%20North%20America/Product%20Support%20Materials/Technique%20Guides/DSUS-JRC-0514-0141%20ATTUNE_CAS_ST.pdf".

(Continued)

Primary Examiner — Anu Ramana
(74) Attorney, Agent, or Firm — Trego, Hines & Ladenheim, PLLC

(57) ABSTRACT

A method of evaluating a human joint which includes two or more bones and ligaments, wherein the ligaments are under anatomical tension to connect the bones together, creating a load-bearing articulating joint. The method includes: defining locations of one or more sockets, each socket representing a ligament attachment point to bone; interconnecting the one or more sockets with mathematical relationships that describe the kinematic physics of the one or more sockets relative to one another; providing spatial information to describe the movement of the sockets relative to one another; defining an initial kinematic state of the joint; defining a final kinematic state of the joint; using computer-based system to compute a difference between the initial and final kinematic states; and using a computer-based system to compute modifications to the mathematical relationships of the sockets to achieve a final kinematic state.

25 Claims, 46 Drawing Sheets

(51) Int. Cl.
*G06N 20/00* (2019.01)
*A61B 34/00* (2016.01)
*A61B 34/20* (2016.01)

(52) U.S. Cl.
CPC .......... *A61F 2/3877* (2013.01); *G06N 20/00* (2019.01); *A61B 2034/107* (2016.02)

(56) References Cited

U.S. PATENT DOCUMENTS

| | | | |
|---|---|---|---|
| 6,022,377 | A | 2/2000 | Nuelle et al. |
| 6,080,154 | A | 6/2000 | Reay-Young et al. |
| 6,162,234 | A | 12/2000 | Freedland et al. |
| 6,205,411 | B1 | 3/2001 | DiGioia, III et al. |
| 7,070,598 | B2 | 7/2006 | Lim et al. |
| 7,849,751 | B2 | 12/2010 | Clark et al. |
| 10,076,377 | B2 | 9/2018 | Bonutti et al. |
| 10,405,849 | B1 | 9/2019 | Cole et al. |
| 10,478,171 | B1 | 11/2019 | Cole et al. |
| 10,555,729 | B1 | 2/2020 | Cole et al. |
| 2001/0008971 | A1 | 7/2001 | Schwartz et al. |
| 2003/0032983 | A1 | 2/2003 | Bonutti et al. |
| 2004/0064191 | A1 | 4/2004 | Wasielewski |
| 2005/0222488 | A1 | 10/2005 | Chang et al. |
| 2005/0267485 | A1 | 12/2005 | Cordes et al. |
| 2008/0051798 | A1 | 2/2008 | Colquhoun et al. |
| 2008/0114367 | A1 | 5/2008 | Meyer |
| 2008/0288060 | A1 | 11/2008 | Kaye et al. |
| 2010/0007140 | A1 | 1/2010 | Duquette et al. |
| 2010/0249659 | A1 | 9/2010 | Sherman et al. |
| 2010/0250571 | A1 | 9/2010 | Pierce et al. |
| 2010/0256612 | A1 | 10/2010 | Dell'Oca |
| 2011/0093081 | A1 | 4/2011 | Chana et al. |
| 2012/0095515 | A1 | 4/2012 | Hamilton |
| 2013/0102929 | A1 | 4/2013 | Haight et al. |
| 2013/0131737 | A1 | 5/2013 | Cheng et al. |
| 2014/0025081 | A1 | 1/2014 | Lorio et al. |
| 2014/0094715 | A1 | 4/2014 | Stein et al. |
| 2014/0194907 | A1 | 7/2014 | Bonutti et al. |
| 2014/0277526 | A1 | 9/2014 | Stein et al. |
| 2014/0296979 | A1 | 10/2014 | Delfosse et al. |
| 2014/0257381 | A1 | 11/2014 | Palese |
| 2015/0105782 | A1 | 4/2015 | D'Lima et al. |
| 2016/0007909 | A1 | 1/2016 | Singh et al. |
| 2016/0030156 | A1 | 2/2016 | Cole |
| 2016/0106409 | A1 | 4/2016 | Moholkar |
| 2016/0278944 | A1 | 9/2016 | D'Lima et al. |
| 2017/0035409 | A1 | 2/2017 | Fallin et al. |
| 2017/0065438 | A1 | 3/2017 | Burnikel |
| 2017/0172624 | A1 | 6/2017 | Brunner et al. |
| 2017/0312099 | A1 | 11/2017 | Paziesnyek |
| 2017/0323481 | A1* | 11/2017 | Tran ................ H04N 5/23219 |
| 2018/0049622 | A1 | 2/2018 | Ryan et al. |
| 2018/0116278 | A1 | 5/2018 | Lang |
| 2018/0153599 | A1 | 6/2018 | Daly et al. |
| 2018/0177612 | A1 | 6/2018 | Masei et al. |
| 2018/0185100 | A1 | 7/2018 | Weinstein et al. |
| 2018/0199952 | A1 | 7/2018 | Cole |
| 2018/0296232 | A1 | 10/2018 | Nielsen et al. |
| 2019/0076273 | A1 | 3/2019 | Goodchild et al. |
| 2019/0147128 | A1* | 5/2019 | O'Connor .............. G16H 50/70 703/11 |
| 2019/0167447 | A1 | 6/2019 | Angibaud |
| 2019/0358056 | A1 | 11/2019 | Lerat et al. |

FOREIGN PATENT DOCUMENTS

| | | | | |
|---|---|---|---|---|
| WO | 2017195046 | | 11/2017 | |
| WO | WO-2017214656 | A1 * | 12/2017 | ............ G06F 30/20 |
| WO | WO-2018144872 | A1 * | 8/2018 | ........... A61B 5/1121 |

OTHER PUBLICATIONS

Bathis et al., "Flexion Gap Configuration in Total Knee Arthroplasty Following Hight Tibial Osteotomy", published online Sep. 30, 2004, International Orthopaedics (SICOT) 28: 366-369.

M. J. Winemaker, MD, FRCS (C), "Perfect Balance in Total Knee Arthroplasty, The Elusive Compromise", The Journal of Arthroplasty vol. 17. No. 1 2002, 2002, Churchill Livingstone, Canada.

International Search Report and Written Opinion from the International Searching Authority for International Patent Application No. PCT/US2019/061668 dated Jan. 14, 2020.

International Search Report and Written Opinion from the International Searching Authority for International Patent Application No. PCT/US2021/018545 dated May 6, 2021.

International Search Report and Written Opinion from the International Searching Authority for International Patent Application No. PCT/US2021/031961 dated Sep. 10, 2021.

U.S. Appl. No. 17/851,869, filed Jun. 28, 2022 titled Knee Endoprothesis.

U.S. Appl. No. 17/851,897, filed Jun. 28, 2022 titled Knee Tensioner—Balancer and Method.

U.S. Appl. No. 17/851,948, filed Jun. 28, 2022 titled Knee Evaluation and Arthroplasty Method.

U.S. Appl. No. 17/881,410, filed Aug. 4, 2022 titled Joint Soft Tissue Evaluation Method.

* cited by examiner

| Data Captured - these Values are inputs sent to Algorithm: | Timestamp | Flexion Angle | Load [lbs] | Centerline Height [mm] | Gap Medial [mm] | Gap Lateral [mm] |
|---|---|---|---|---|---|---|
| Datasource: A = Auto, M = Manual | Control System | A: Tracking System (NAV [local or global]) M: "leg protractor" | A: Measured Current [mA] from Motor M: T-Handle Driver (torque) | A: Encoder Counts M: T-Handle Driver (angle) | A: Tracking System (NAV [local or global] or Transducer along top plate pivot axis M: "plate protractor" | |
| | 44:37.0 | 0 | 45 | | 12.0 | 12.4 |
| | 44:37.1 | 2 | 45 | | 11.9 | 12.4 |
| | ... | | | | | |
| | 44:42.9 | 118 | 45 | | 13.3 | 13.9 |
| | 44:43.0 | 120 | 45 | | 13.3 | 14.0 |

Fig. 23

MACHINE LEARNING BASED JOINT EVALUATION METHOD

BACKGROUND

This invention relates generally to medical devices and instruments, and more particularly to methods for knee evaluation and arthroplasty.

Total knee arthroplasty ("TKA") is a procedure for treating an injured, diseased, or worn human knee joint. In a TKA, an endoprosthetic joint is implanted, replacing the bearing surfaces of the joint with artificial members. Proper alignment of the joint and substantially equal tension in the soft tissues surrounding the joint are important factors in producing a good surgical outcome.

A human knee joint "J" is shown in FIGS. 1-4. The joint J is prepared for implantation by cutting away portions of the femur "F" and the tibia "T". FIGS. 1 and 2 show the joint in extension, with cutting planes for a tibial cut 1 and a distal femoral cut 2. The tibial cut 1 and the distal femoral cut 2 cooperate to define an extension gap "EG". FIGS. 3 and 4 show the joint J in flexion, with a cutting plane 3 shown for a posterior cut. The tibial cut 1 and the posterior cut 3 cooperate to define a flexion gap "FG".

FIG. 5 depicts an exemplary endoprosthetic 10 (i.e., implant) of a known type. The endoprosthetic 10 includes a tibial component 12 and a femoral component 14. The tibial component 12 is made up of a tibial tray 16 and an insert 18. The insert 18 has a back surface 20 which abuts the tibial tray 16 and an opposed articular surface 22. The tray includes a prominent keel 24 protruding in the inferior direction (i.e. down a longitudinal axis of the tibia). The tibial tray 16 may be made from a hard, wear-resistant material such as a biocompatible metal alloy. The insert 18 may be made from a low-friction material such as a biocompatible plastic.

The femoral component 14 includes a back surface 36 shaped to abut a surface of the femur F that has been appropriately shaped and an articular surface 38 comprising medial and lateral contact surfaces 39 and 41, respectively. The femoral component 14 may be made from a hard, wear-resistant material such as a biocompatible metal alloy. The back surface 36 includes multiple faces collectively defining a rough "U" or "J" shape. The back surface 36 includes protruding locator pins 50.

The tibial tray 16 is implanted into the tibia T and the femoral component 14 is implanted into the femur F. The insert 18 is placed into the tibial tray 16. The articular surface 22 of the insert 18 bears against the articular surface 38 of the femoral component 14, defining a functional joint.

In the illustrated example, the endoprosthesis 10 is of the cruciate-retaining ("CR") type. It includes a cutout or notch 26 in the posterior aspect of the tibial component 12 which provides a space for the posterior cruciate ligament ("PCL").

A goal of total knee arthroplasty is to obtain symmetric and balanced flexion and extension gaps FG, EG (in other words, two congruent rectangles). These gaps are generally measured in millimeters of separation, are further characterized by a varus or valgus angle measured in degrees, and are measured after the tibia cut, distal femoral cut, and posterior femoral cut have been done (to create flat surfaces from which to measure). It follows that, to achieve this balance, the ligament tension in the lateral and medial ligaments would be substantially equal on each side or have a surgeon-selected relationship, and in each position.

One problem with prior art arthroplasty techniques is that it is difficult and complex to achieve the proper balance. Current state-of-the-art gap balancing devices do not enable balancing with the patella in-place and are large, overly-complicated devices that work only with their respective knee implant systems.

BRIEF SUMMARY OF THE INVENTION

This problem is addressed by a computer-based method of evaluating a human joint.

According to one aspect of the technology described herein, a method is describe of evaluating a human joint which includes two or more bones and ligaments, wherein the ligaments are under anatomical tension to connect the bones together, creating a load-bearing articulating joint. The method includes: defining locations of one or more sockets, each socket representing a ligament attachment point to bone; interconnecting the one or more sockets with mathematical relationships that describe the kinematic physics of the one or more sockets relative to one another; providing spatial information to describe the movement of the sockets relative to one another; defining an initial kinematic state of the joint; defining a final kinematic state of the joint; using computer-based system to compute a difference between the initial and final kinematic states; and using a computer-based system to compute modifications to the mathematical relationships of the sockets to achieve a final kinematic state.

According to another aspect of the technology described herein, a method is described of evaluating a human joint which includes two or more bones and ligaments, wherein the ligaments are under anatomical tension to connect the bones together, creating a load-bearing articulating joint. The method includes: distracting the joint to develop a set of data; the data including at least a stress strain curve, evaluating the stress strain curve to compute an intraoperative procedural pathway; evaluating qualitatively and quantitatively a postoperative patient result as a dataset; using the result dataset as an input into a database; and using the database to develop future procedural pathways and to use as inputs into machine learning-based decisions.

BRIEF DESCRIPTION OF THE DRAWINGS

The invention may be best understood by reference to the following description taken in conjunction with the accompanying drawing figures in which:

FIG. 23 is a diagram showing example of data collected using a tensioner-balancer and tracking markers;

DETAILED DESCRIPTION OF THE INVENTION

Figure 1:
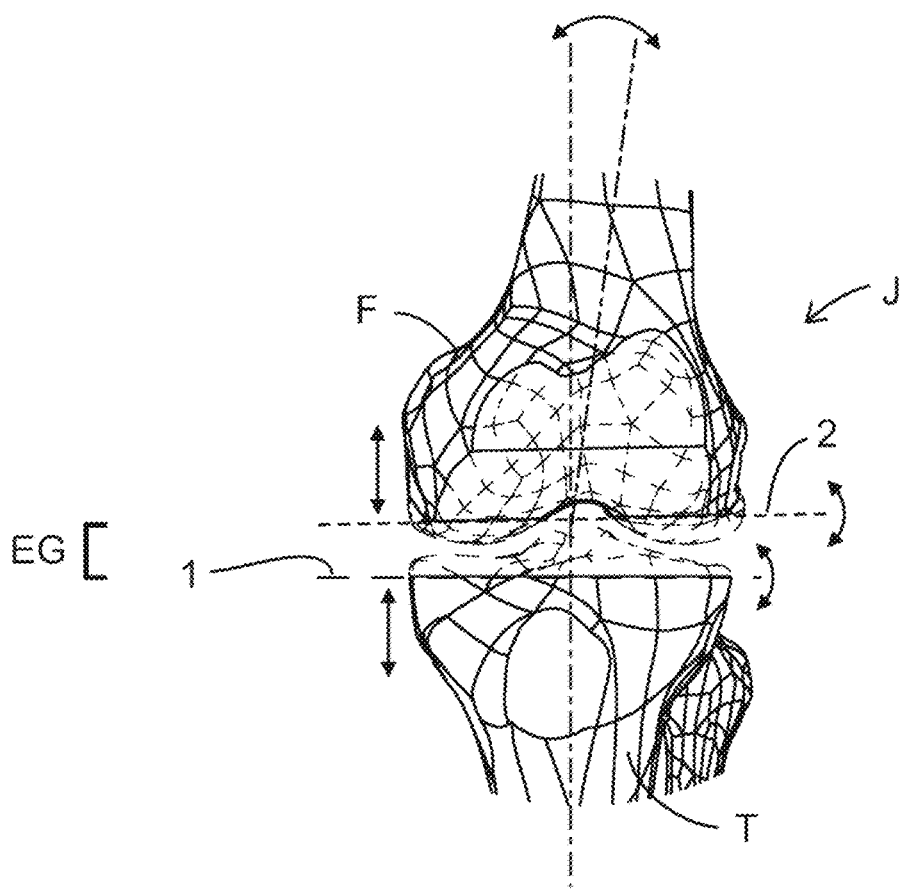
FIG. 1 is a view of the anterior aspect of the human knee joint in extension showing cutting planes for a total knee arthroscopy.
Figure 2:
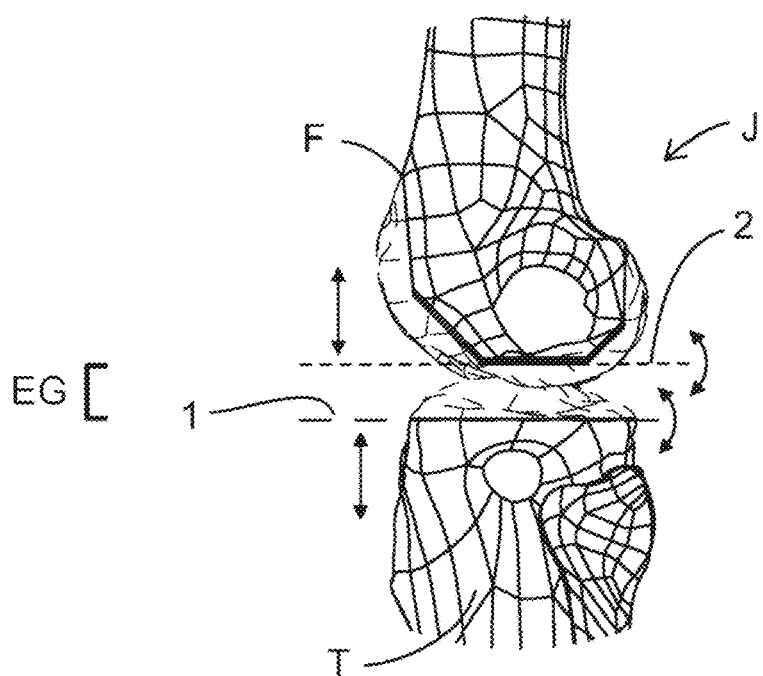
FIG. 2 is a view of the lateral aspect of the human knee joint of FIG. 1.
Figure 3:
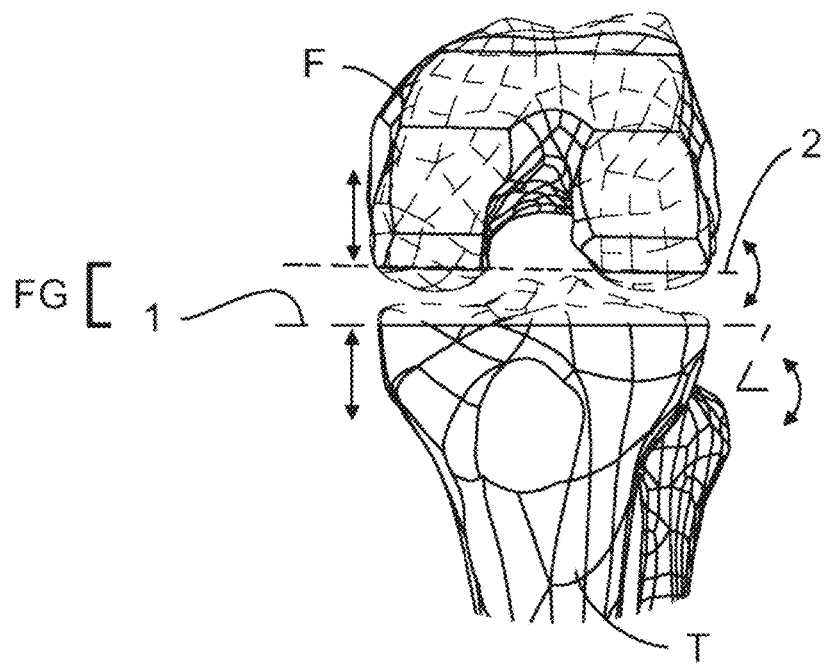
FIG. 3 is a view of the anterior aspect of the human knee joint in flexion showing cutting planes for a total knee arthroscopy.
Figure 4:
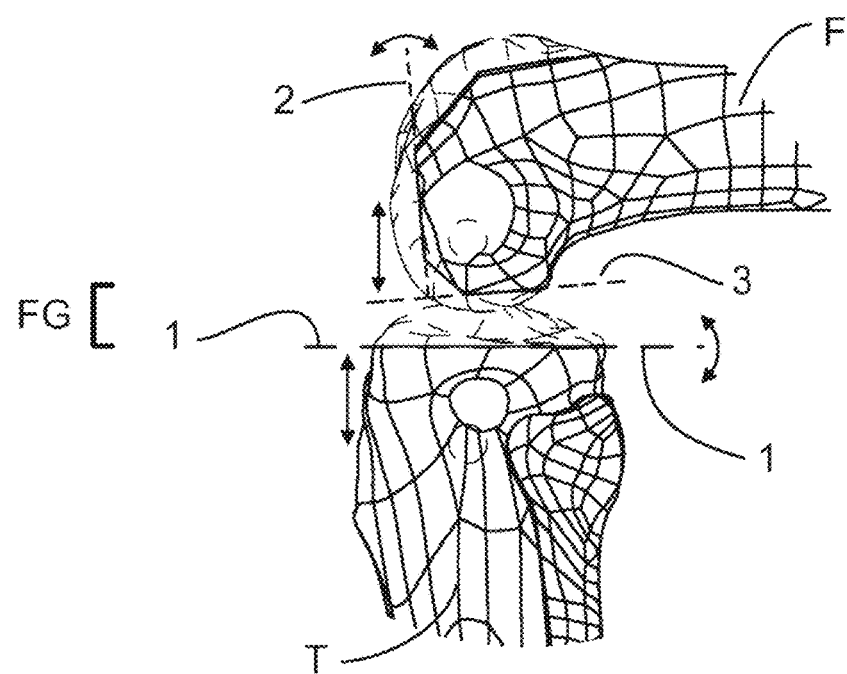
FIG. 4 is a view of the lateral aspect of the human knee joint of FIG. 3.
Figure 5:
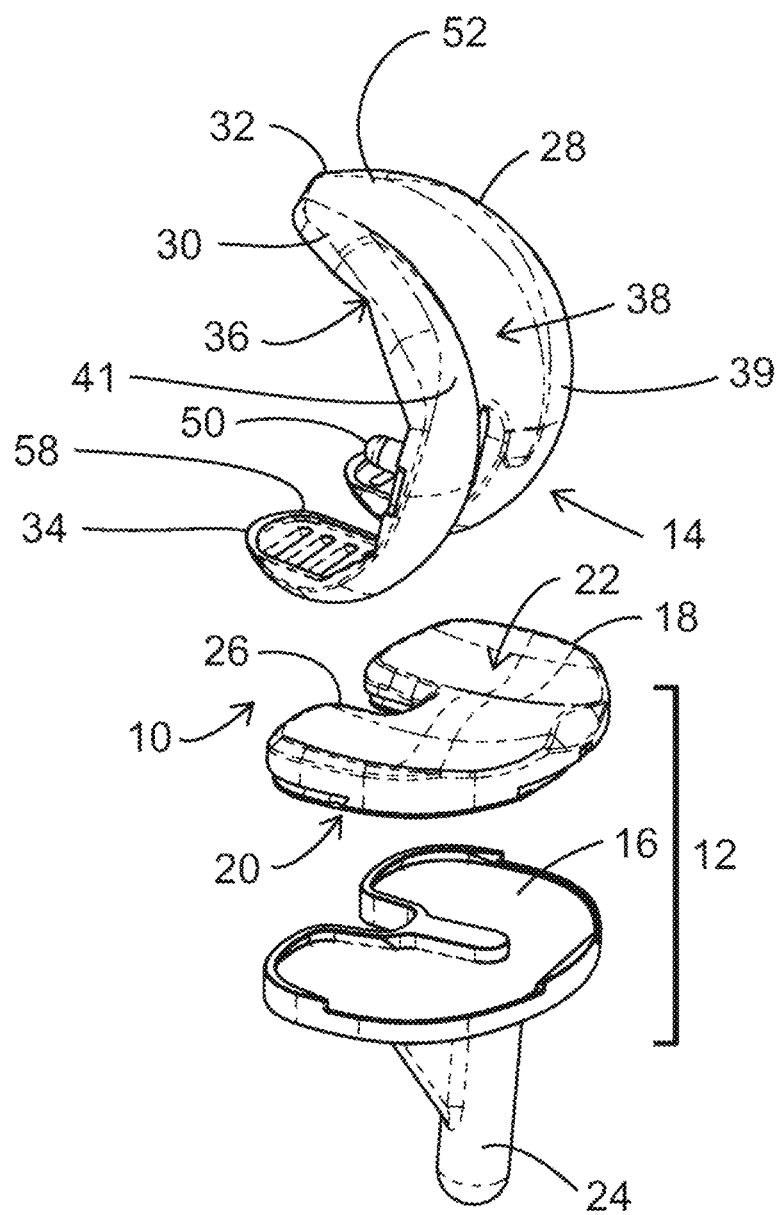
FIG. 5 is an exploded perspective view of a representative knee endoprosthesis.
Figure 6:
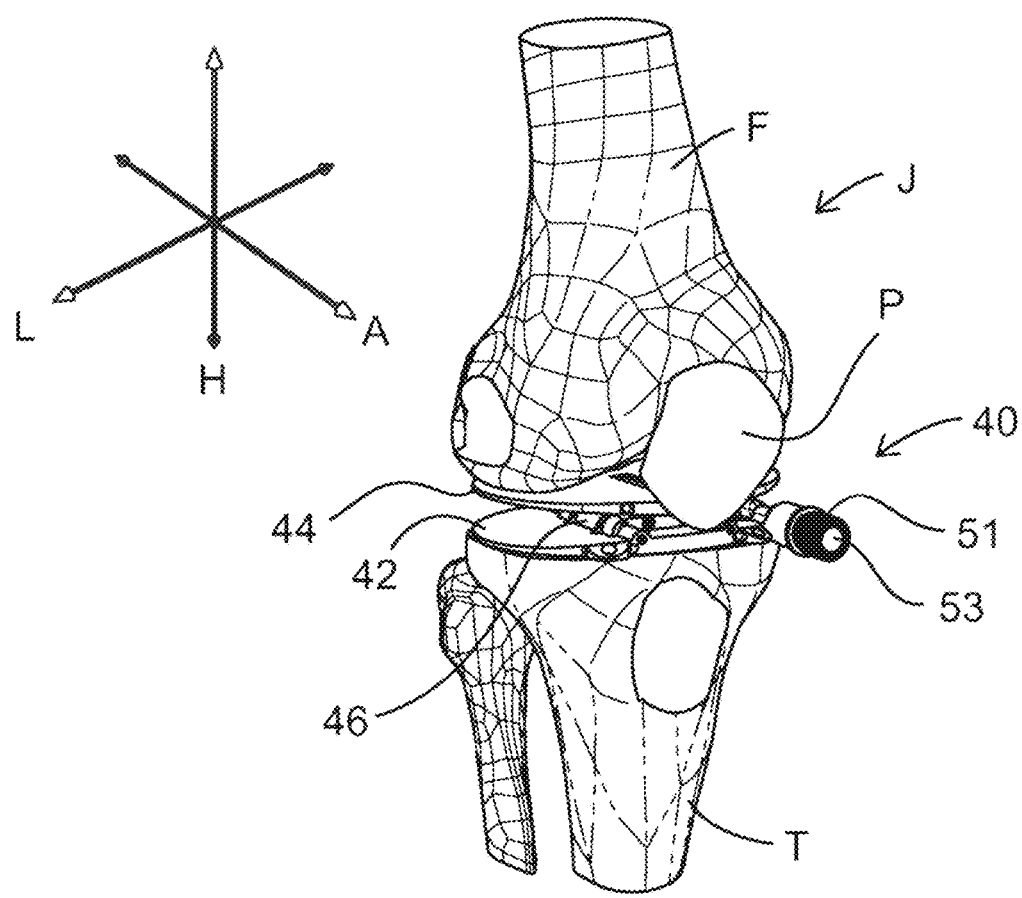
FIG. 6 is a perspective view of a human knee joint in an extended position, with a tensioner-balancer inserted therein.
Figure 7:
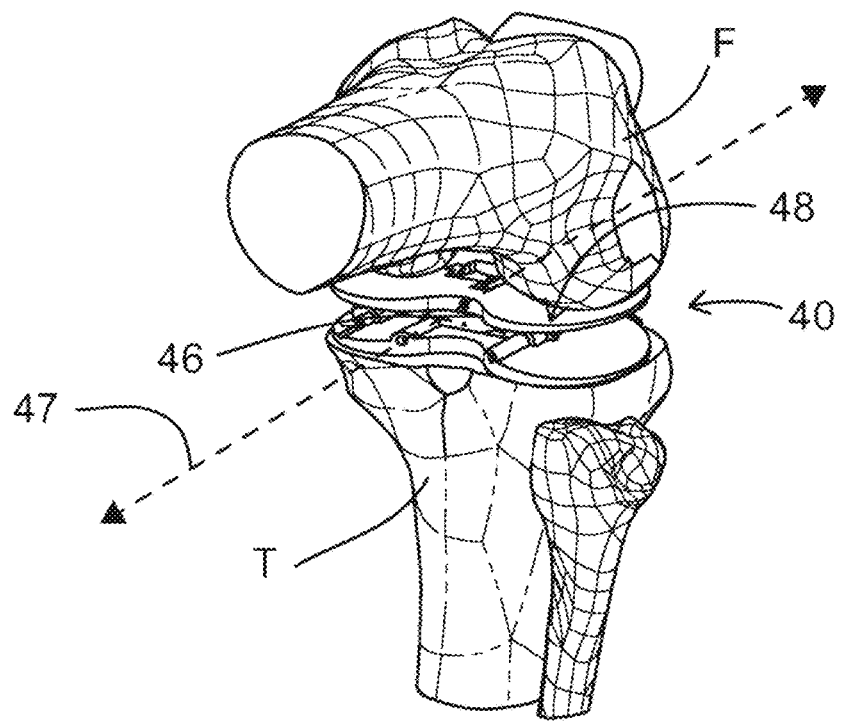
FIG. 7 is a view of the knee joint and tensioner-balancer of FIG. 6, in a flexed position.

Now, referring to the drawings wherein identical reference numerals denote the same elements throughout the various views, FIGS. 6 and 7 depict an exemplary embodiment of a tensioner-balancer 40 (alternatively referred to in various embodiments as a gap balancer, distractor, distractor-tensioner, or jack) which is useful for balancing a gap in a human knee joint as part of a total knee arthroplasty and for other therapeutic procedures.

Solely for purposes of convenient description, the tensioner-balancer 40 may be described as having a length extending along a lateral-to-medial direction "L", a width extending along an axial direction "A", and a height extending along a vertical direction "H", wherein the lateral direction, the axial direction, and the vertical direction are three mutually perpendicular directions. These directional terms, and similar terms such as "top", "bottom", "upper", "lower" are used merely for convenience in description and do not require a particular orientation of the structures described thereby.

In one aspect, the tensioner-balancer 40 may be described as having the ability to control the movement of one degree of freedom (e.g., translation along H) and measure the movement of a second degree of freedom (rotation about A) while constraining or fixing the remaining four degrees of freedom (translation along A and L; rotation about H and L).

The tensioner-balancer 40 comprises a baseplate 42 and a top plate 44 interconnected by a linkage 46. The linkage 46 and the tensioner-balancer 40 are movable between a retracted position in which the top plate 44 lies close to or against the baseplate 42, and an extended position in which the top plate 44 is spaced away from the baseplate 42. As described in more detail below, a means is provided to actuate the linkage 46 in response to an actuating force in order to separate the baseplate 42 and the top plate 44 in a controllable manner. This separation enables it to extend so as to apply a load to a knee joint. While the illustrated tensioner-balancer 40 includes a mechanically-operated linkage 46, it will be understood that this is just one operative example of a "distracting mechanism" operable to move the tensioner-balancer between retracted and extended positions. It is envisioned that the mechanical linkage could be replaced with other types of mechanical elements, or electrical, pneumatic, or hydraulic devices.

The top plate 44 includes a femoral interface surface 48 and is mounted to the linkage 46 in such a manner that it can freely pivot about pivot axis 47 (an axis corresponding to a varus/valgus angulation of the knee).

The baseplate 42 includes a tensioner-balancer coupler 51 having a first interface 53. In the illustrated example, the first interface 53 is configured as a mechanical coupling. The coupler 51 is interconnected to the linkage such that an actuating force applied to the coupler 51, such as a torque, actuates the linkage 46. A drive shaft (not shown) passes through this coupler and connects with the linkage.

Optionally, the tensioner-balancer 40 may incorporate means for measuring a force input. For example, the coupler 51 may incorporate a sensor (not shown) such as a strain gage operable to produce a signal representative of the torque applied to the coupler 51.

As a further option, the tensioner-balancer 40 may incorporate a separate measuring linkage (not shown) connected to the top plate and arranged to follow the movement of the top plate 44. The measuring linkage would be connected to a crank which would be in turn connected to an indicating shaft coaxial to the coupler. The measuring linkage may be arranged such that pivoting movement of the top plate results in rotation of the indicating shaft. The movement of the indicating shaft may be observed visually, or it may be detected by a sensor such as an RVDT or rotary encoder or resolver, which may be part of an instrument described below. This permits measurement of plate angle and/or vertical position.

The tensioner-balancer may be supplied with an appropriate combination of transducers to detect physical properties such as force, tilt angle, and/or applied load and generate a signal representative thereof. For example, the tensioner-balancer may be provided with sensors operable to detect the magnitude of extension (i.e. "gap height"), the angle of the top plate about the pivot axis 47 (i.e. varus/valgus), and/or the applied force in the extension direction. Nonlimiting examples of suitable transducers include strain gages, load cells, linear variable differential transformers ("LVDT"), rotary variable differential transformers ("RVDT"), or linear or rotary encoders or resolvers.

Figure 8:
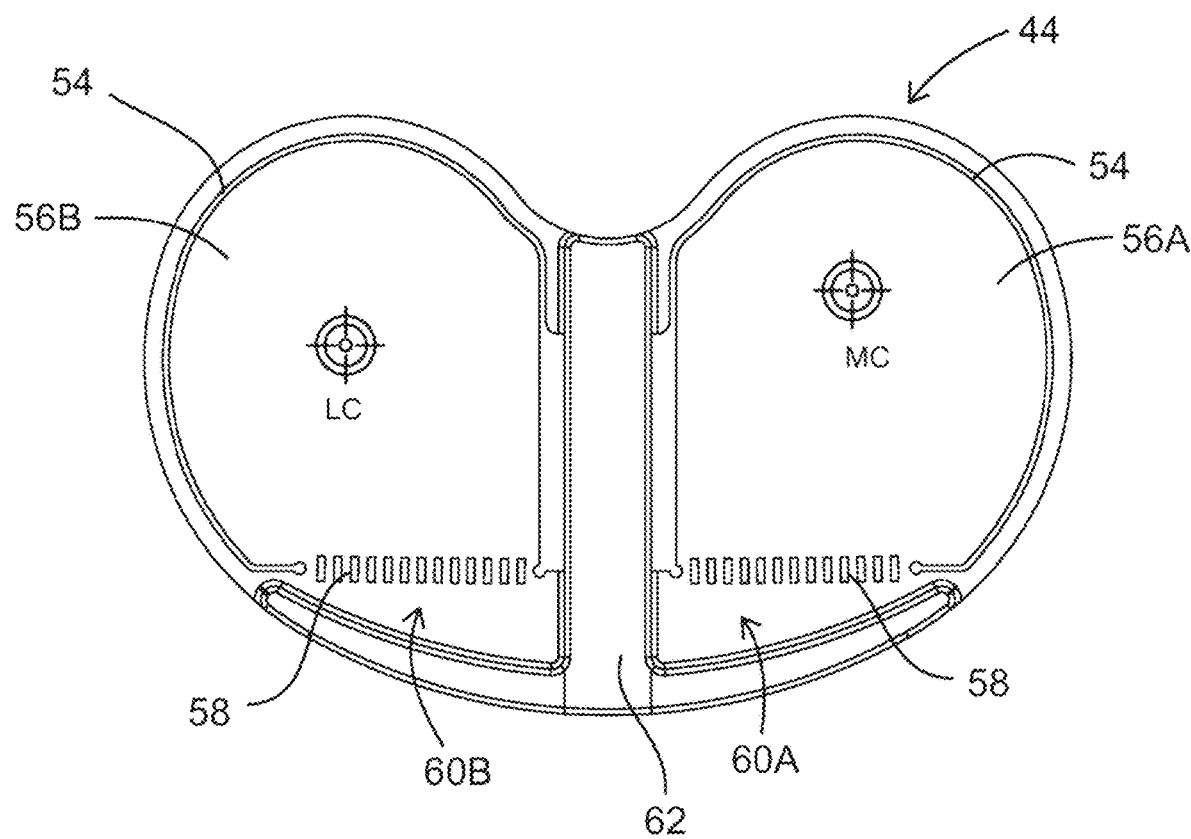
FIG. 8 is a top plan view of a top plate of the tensioner-balancer of FIG. 6.
Figure 9:
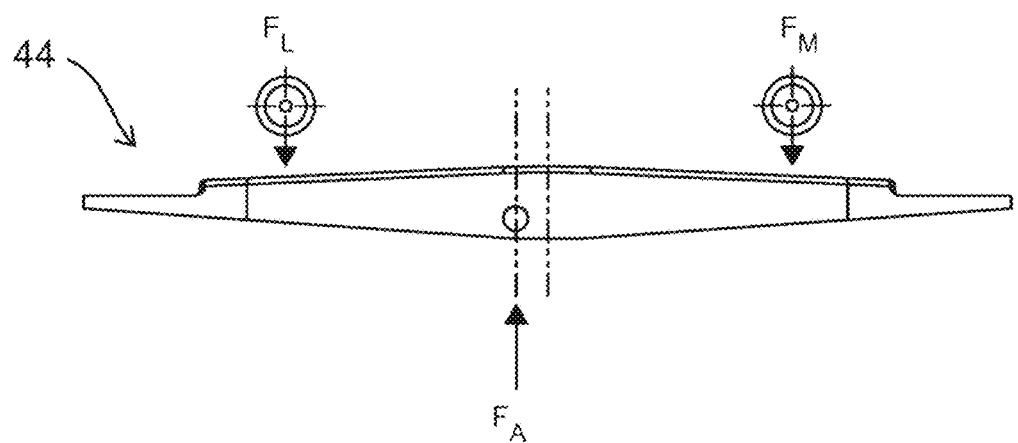
FIG. 9 is a front elevation view of the top plate of FIG. 8.

FIGS. 8 and 9 illustrate an exemplary configuration in which the top plate 44 includes grooves 54 which define medial and lateral cantilevered pads 56A, 56B respectively. Two or more spaced-apart strain gages 58 are mounted to the top plate 44 in a first left-right row 60A at the intersection between the medial pad 56A and the forward portion 62 of the top plate 44. Two or more spaced-apart strain gages 58 are mounted to the top plate 44 in a second fore-aft row 60B at the intersection between the lateral pad 56B and the forward portion 62 of the top plate 44.

Figure 10:
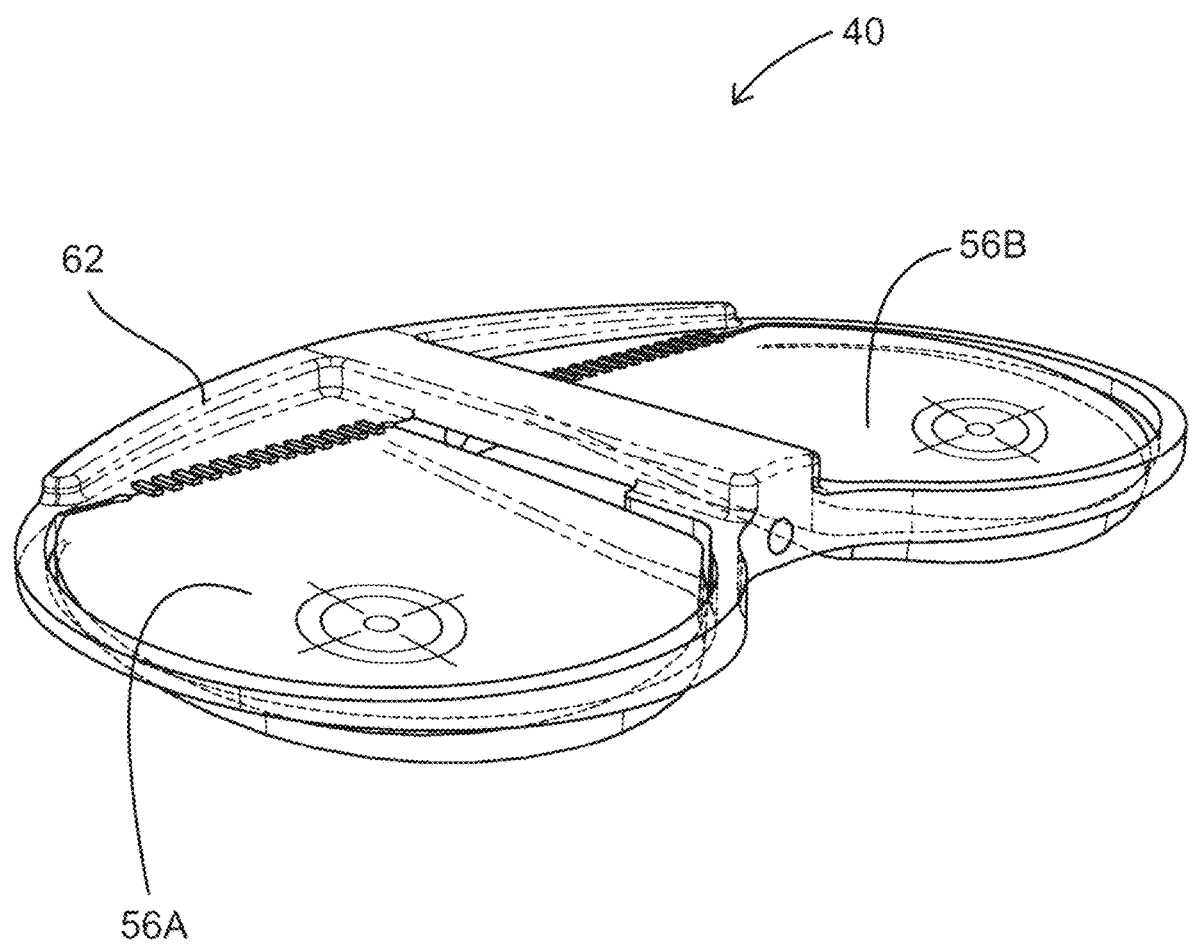
FIG. 10 is a perspective view of the top plate of FIG. 8, in a deflected position.

FIG. 10 shows the medial and lateral cantilevered pads 56A, 56B in a deflected position under load. The magnitude of deflection is greatly exaggerated for illustrative purposes.

Referring to FIG. 8, when the knee joint is articulated it is possible to identify an instantaneous point of peak contact pressure. There is one such point for each of the condyles. These positions are mapped onto the medial and lateral cantilevered pads 56A, 56B and labeled "MC" (standing for "medial load center") and "LC" (standing for "lateral load center").

Figure 11:
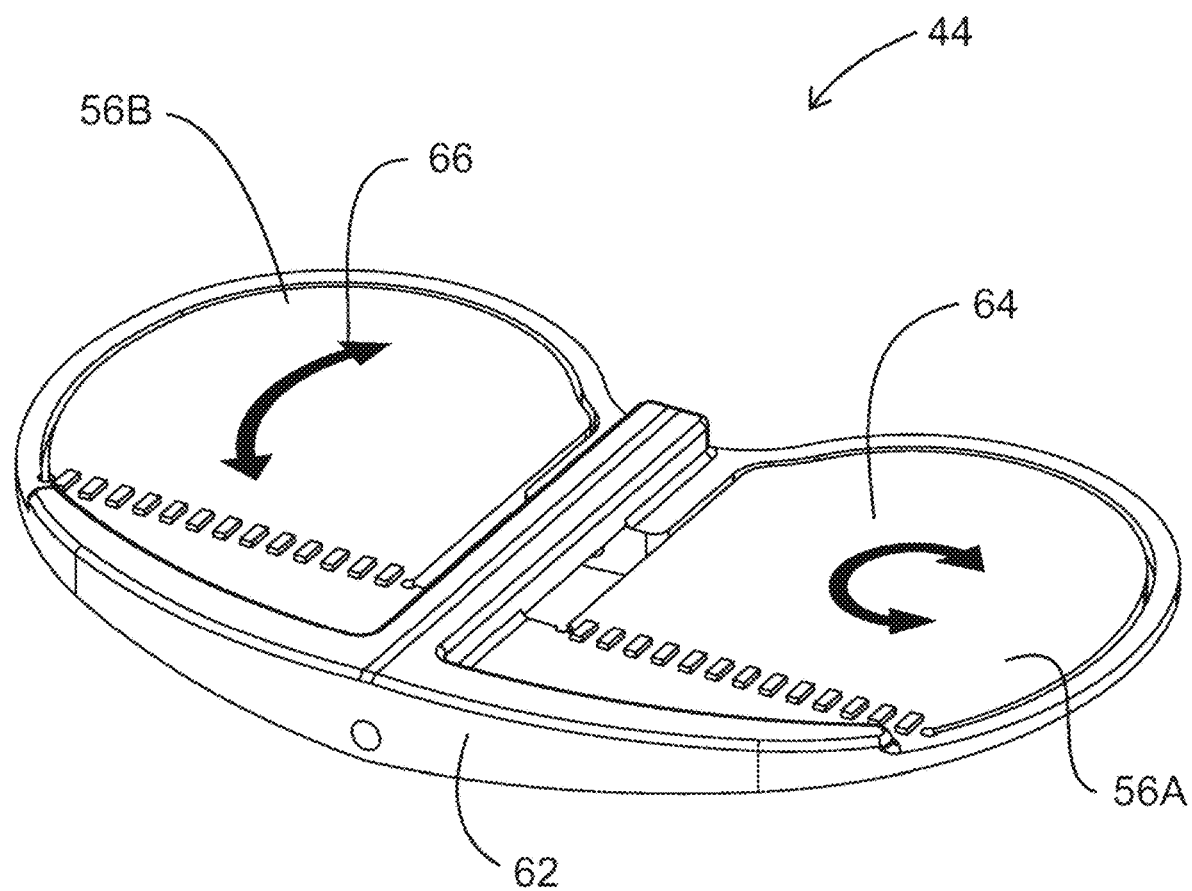
FIG. 11 is a perspective view of the top plate of FIG. 8, showing movement of contact points superimposed thereon.

Analysis by the inventors has shown that using the depicted configuration, with one or more strain gauges provided for each of the cantilevered pads 56A, 56B, it is possible to resolve the position of the load centers LC, MC in two axes. Stated another way, using this hardware, it is possible to identify the instantaneous lateral-medial and anterior-posterior position of the load centers LC, MC. More complex sensors may permit the resolution in two axes using one or more strain gage for each cantilevered pad. Referring to FIG. 11, and as will be described further below, this enables the ability of the tensioner-balancer 40 to track certain relative movements of the femur F. One of these is referred to as "medial pivot" shown by arrow 64 and the other is referred to as "rollback", shown by arrow 66.

Figure 12:
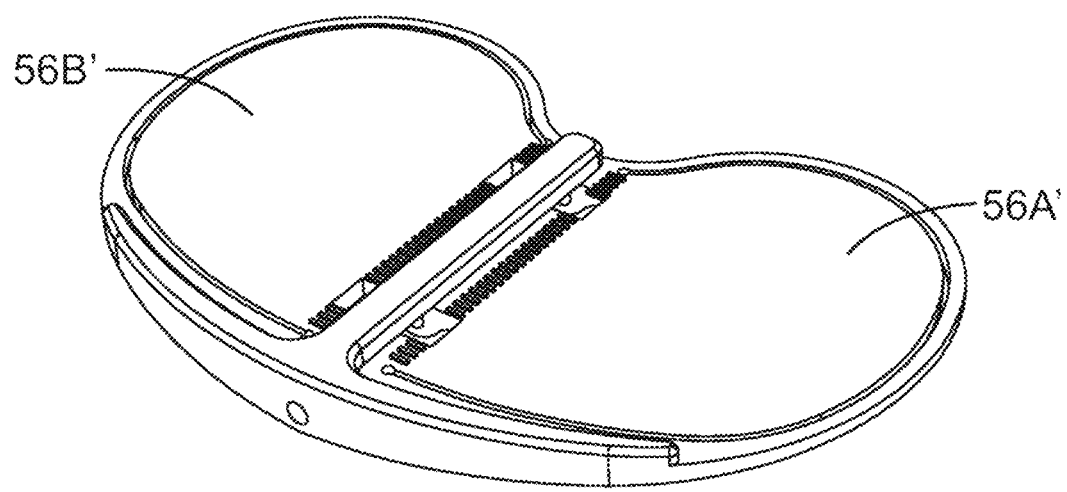
FIG. 12 is a perspective view of an alternative top plate configuration of the tensioner-balancer of FIG. 6.
Figure 13:
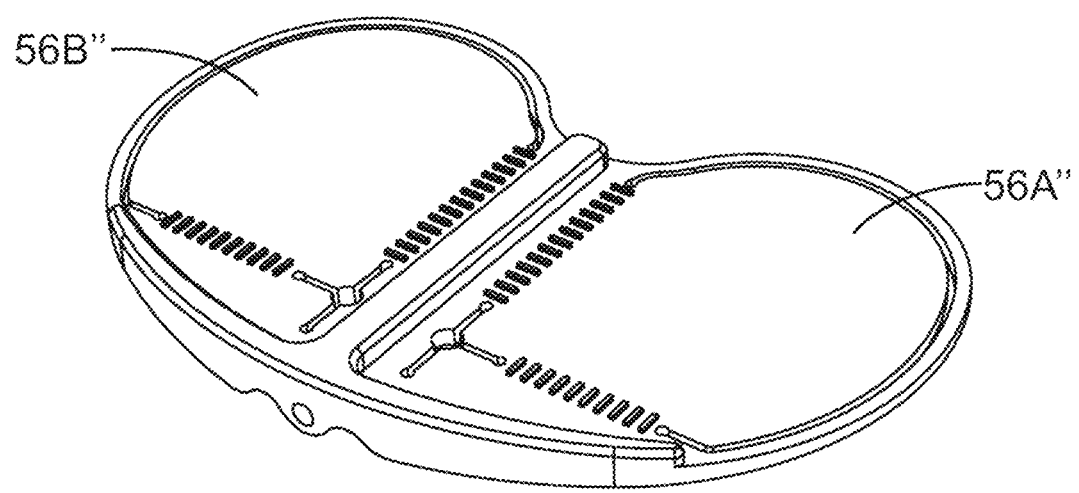
FIG. 13 is a perspective top plan view of an alternative top plate configuration of the tensioner-balancer of FIG. 6.

Various physical configurations of the top plate with cantilevered pads are possible with similar functionality. For example, FIG. 12 illustrates medial and lateral cantilevered pads 56A', 56B' which are cantilevered along an anterior-posterior axis (as opposed to a lateral-medial axis as shown in FIGS. 8-10). As another example, FIG. 13 illustrates medial and lateral cantilevered pads 56A", 56B" which are cantilevered along both an anterior-posterior axis and a lateral-medial axis. As another alternative (not separately illustrated), the lateral pad could be cantilevered along one axis and the medial pad could be cantilevered along a different axis.

Figure 14:
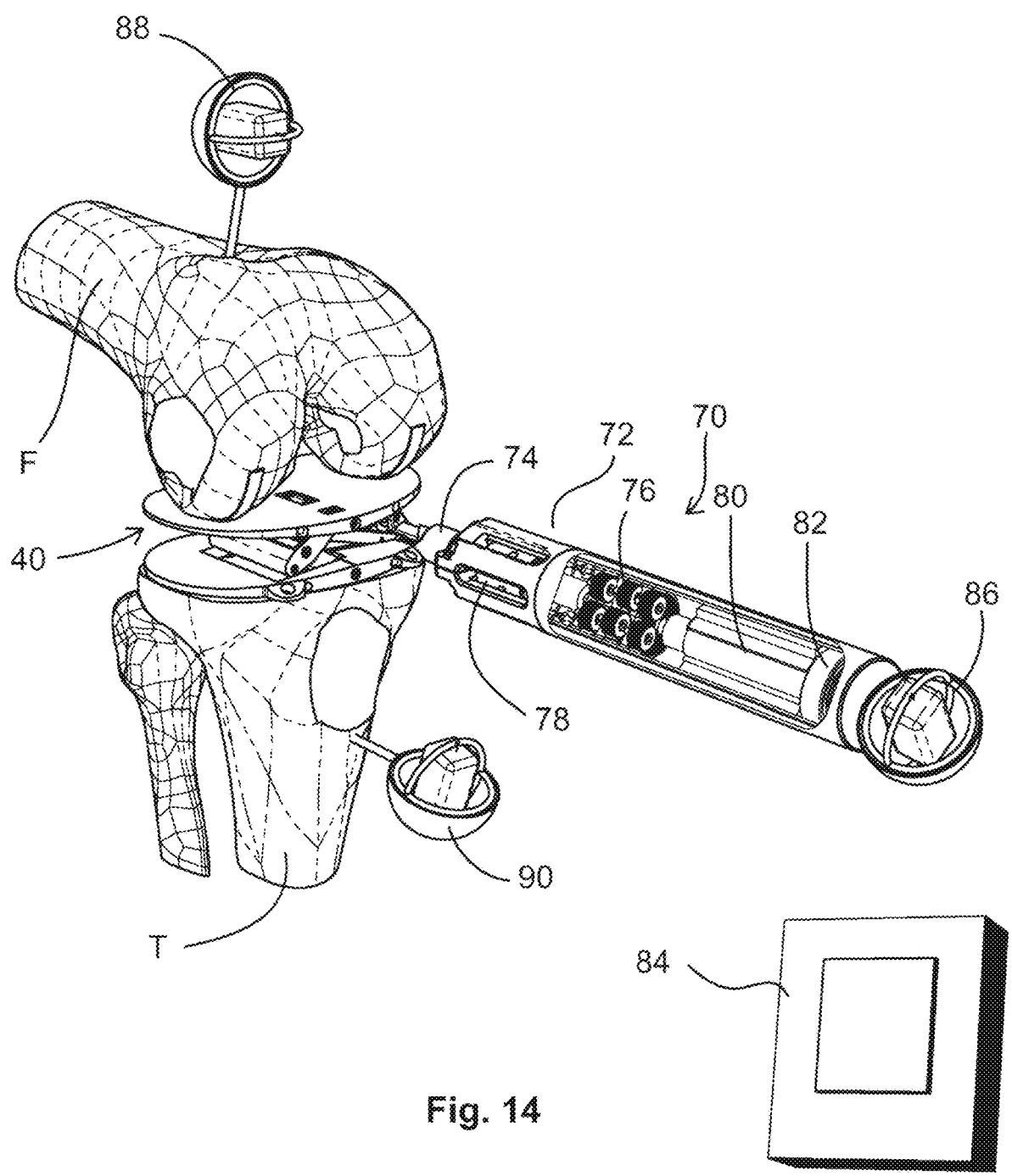
FIG. 14 is a perspective view of the human knee joint with a tensioner-balancer inserted therein and coupled to a instrument.

FIG. 14 illustrates an exemplary actuating instrument 70 for use with the tensioner-balancer 40. The actuating instrument 70 includes a barrel 72 with an instrument coupler 74 at its distal end defining a second interface (hidden in this view) which is complementary to the first interface 53 of the tensioner-balancer 40. The interior of barrel 72 includes an appropriate internal mechanism to apply torque to the instrument coupler 74, through a shaft 78, such as a servo or stepper motor 80 with related control electronics including a rotary encoder coupled to a planetary gearset 76 that interconnects the servo motor 80 and shaft 78.

The internal mechanism is operable to apply an actuating load to the tensioner-balancer 40. The actuating instrument 70 includes an electronic data transceiver, shown schematically at 82. The transceiver 82 may operate over a wired or wireless connection. The actuating instrument 70 may be supplied with an appropriate combination of transducers (not shown in FIG. 14) to detect physical properties such as force, tilt angle, and/or applied load and generate a signal representative thereof. For example, the tensioner-balancer 40 may be provided with sensors operable to detect the magnitude of extension (i.e. "gap height"), the angle of the top plate about the pivot axis (i.e. varus/valgus), and/or the applied force in the extension direction. Nonlimiting examples of suitable transducers include strain gages, load cells, linear variable differential transformers ("LVDT"), rotary variable differential transformers ("RVDT"), or linear or rotary encoders or resolvers.

Displacement of the tensioner-balancer 40 may be derived from the encoder signals, knowing the kinematics of the linkage 46. The transceiver 82 is operable to transmit the signal.

A remote display 84 is configured to receive the signal and produce a display of the transducer data. As one example, the remote display 84 may be embodied in a conventional portable electronic device such as a "smart phone" or electronic tablet with suitable software programming. Optionally, the remote display 84 or other suitable transmitting device may be used to send remote operation commands to the actuating instrument 70.

In use, the remote display 84 permits the surgeon to observe the physical properties of the tensioner-balancer 40 in real time as the actuating instrument 70 is used to operate the tensioner-balancer 40.

Optionally, the actuating instrument 70 may incorporate a tracking marker 86. The tracking marker 86 is operable such that, using an appropriate receiving device, the position and orientation of the receiving device relative to the tracking marker 86 may be determined by receipt and analysis at the receiving device of signals transmitted by the tracking marker 86.

As illustrated, the tracking marker 86 may be configured as an inertial navigation device including one or more accelerometers and gyroscopic elements capable of providing angular rate information and acceleration data in 3D space.

In an alternative embodiment which is not illustrated, the tracking marker may include one or more tracking points which may be configured as transmitting antennas, radiological markers, or other similar devices.

6 degree-of-freedom, local NAV, non-line-of sight, tracking markers 86 and appropriate receivers are known within the state-of-the-art.

A tracking marker 88 would be attached to the femur F in such a way that it has a substantially fixed position and orientation relative to the femur F. For example, a tracking marker 88 may be attached directly to the femur F.

In addition to the femur-mounted tracking marker 88, at least one additional tracking marker is provided which has a substantially fixed position and orientation relative to the tibia T. Where the actuating instrument 70 is rigidly coupled to the tensioner-balancer 40, the tibial tracking function may be provided by the tracking marker 86 of the actuating instrument 70. Alternatively, a tracking marker 90 may be attached directly to the tibia T.

Figure 15:
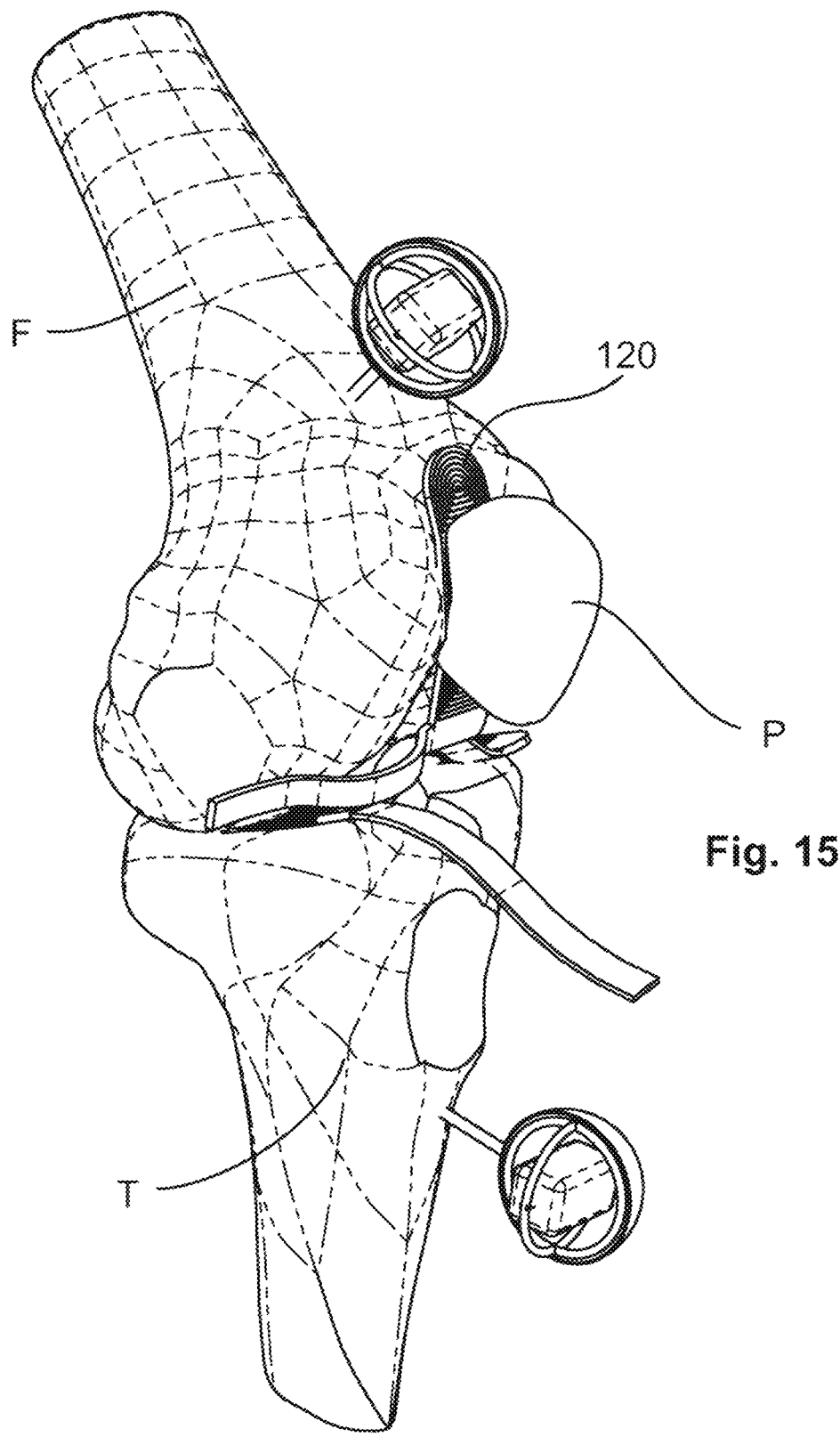
FIG. 15 is a perspective view of a human knee joint with a load cell disposed contact with the patella.

In addition to collecting force, pressure, and/or displacement data between the femur F and the tibia T, an additional device may be used to collect force, pressure, and/or displacement data between the femur F and the patella P. FIG. 15 shows a human knee joint J in flexion. A patella force sensor 120 is shown disposed between the patella P and the femur F. The patella force sensor 120 may include one or more individual sensors operable to detect force, pressure, and/or displacement and produce representative signals, as described above with respect to the sensors of the gap balancer embodiments. This data may be transmitted through a flexible cable as shown in FIG. 15, or over a wireless connection.

Figure 16:
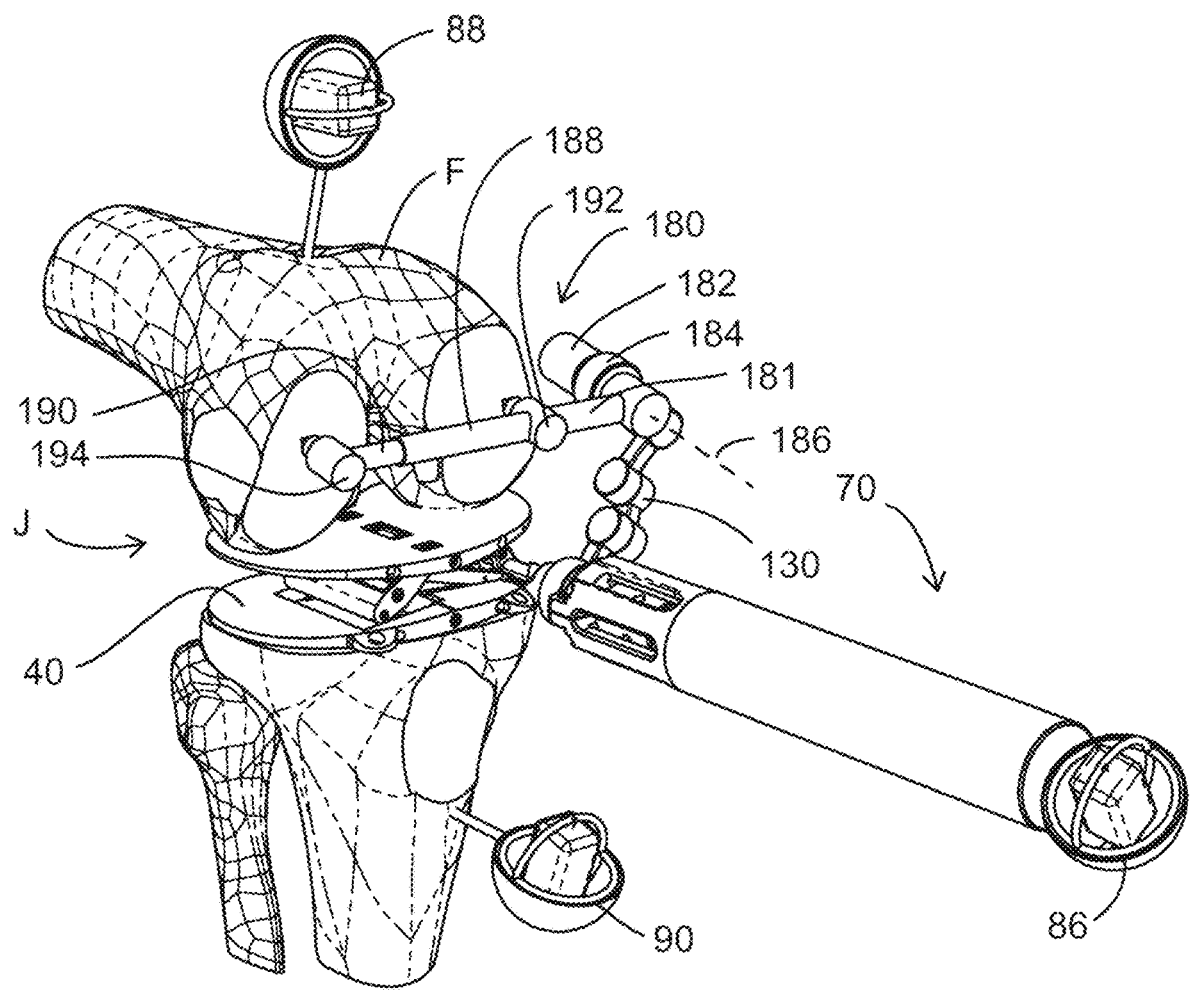
FIG. 16 is a perspective view of a tensioner-balancer inserted into human knee joint, in combination with a spotting apparatus.

The utility of the tensioner-balancer 40 may be extended by various attachments. As an example, FIG. 16 illustrates a spotting apparatus 180. This comprises a bar 181 extending from an articulated mount 182 which is in turn coupled to the tensioner-balancer 40. The mount 182 includes an actuator 184 permitting the bar 180 to pivot about a first axis 186. The bar 181 is formed in two telescoping sections 188, 190 which may be extended or retracted using an internal actuator (not shown). The first telescoping section 188 carries a first spotting element 192 such as a rotary center drill, and the second telescoping section 190 carries a second spotting element 194 such as a rotary center drill. Movement of the spotting apparatus 180 permits the first and second spotting elements 192, 194 to be driven to selected locations relative to the condyles of the femur F. The spotting elements 192, 194 may then be used to form identifiable reference features in the femur F, such as small blind center drill holes. These reference features may then be used to provide a fixed position reference on the femur F for further surgical procedures.

The apparatus described above is suitable for various surgical procedures.

In one procedure, the tensioner-balancer 40 is used to evaluate the knee and to model and digitize the articular surfaces of the knee over its range of motion.

More particularly, the locus of points of contact of the femur F and the top plate 44 are modeled as a medial spline and the lateral spline.

To carry out this modeling, the tensioner-balancer is inserted between the femur F and the tibia T. As shown in FIG. 14, this is accomplished after having first made the tibial plateau cut. However, the tibial plateau cut is not required.

The actuating instrument 70 is coupled to the tensioner-balancer 40. Femoral tracking marker 88 is implanted to the femur F. At least one of tibial tracking marker 90 and instrument tracking marker 86 is placed.

The tensioner-balancer 40 is extended to apply a load to the knee joint. While different modes of operation are possible, one exemplary mode is to extend the tensioner-balancer 40 until a predetermined distraction load is applied. Feedback control or mechanical spring preload may then be used to maintain this distraction load, while the top plate 44 is permitted to pivot freely and translate vertically while the degrees of pivot and vertical displacement are measured, tracked, and recorded by the feedback control hardware and software. One example of a suitable distraction load is approximately 130 N (30 lb.) to 220 N (50 lb.). Another exemplary mode is to extend the tensioner-balancer 40 until a predetermined distraction distance is applied. Feedback control may then be used to maintain this distraction distance, while the top plate 44 is permitted to pivot freely and while the degrees of pivot and distraction load are measured, tracked, and recorded by the feedback control hardware and software.

Figure 17:
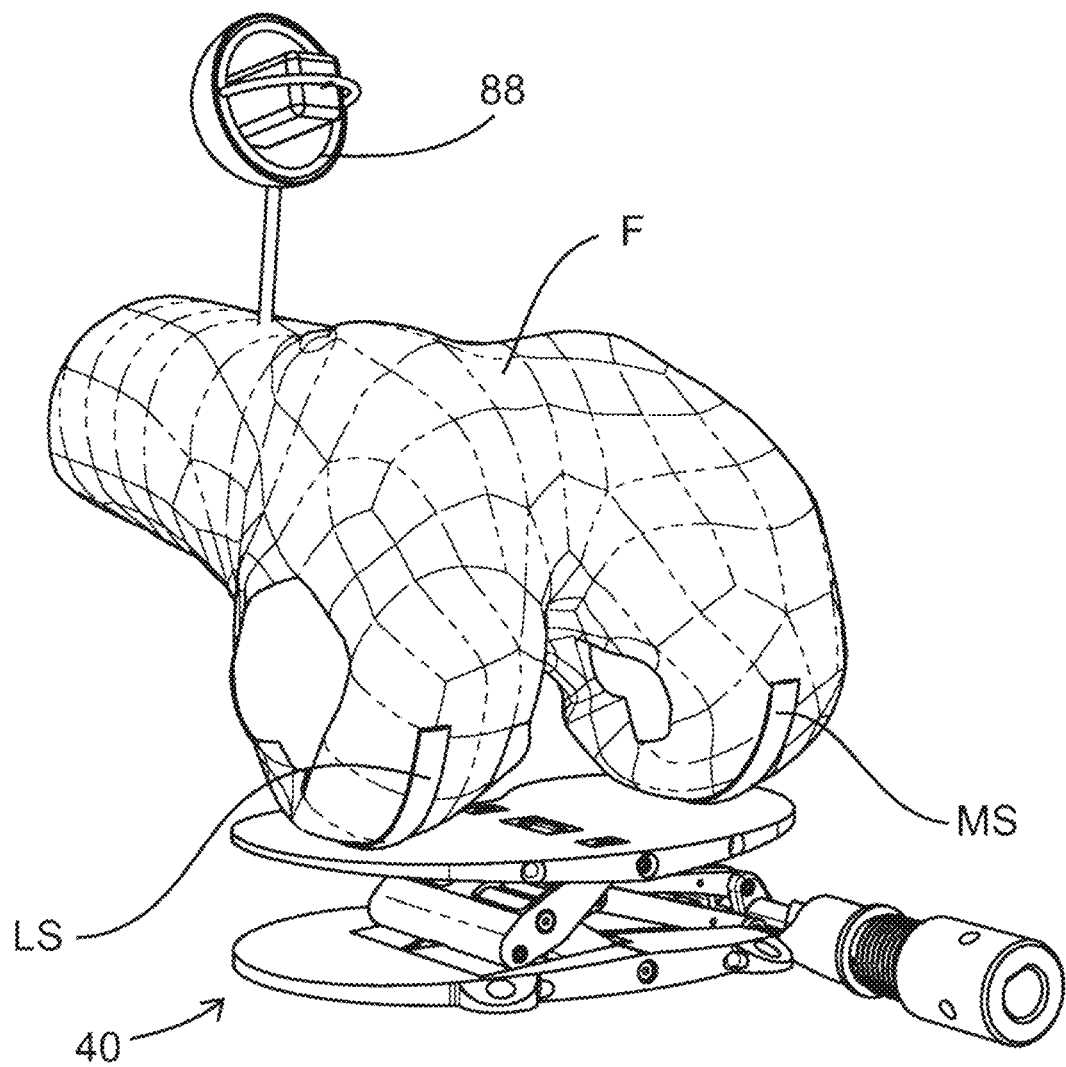
FIG. 17 is a perspective view showing a femur in contact with a tensioner-balancer.
Figure 18:
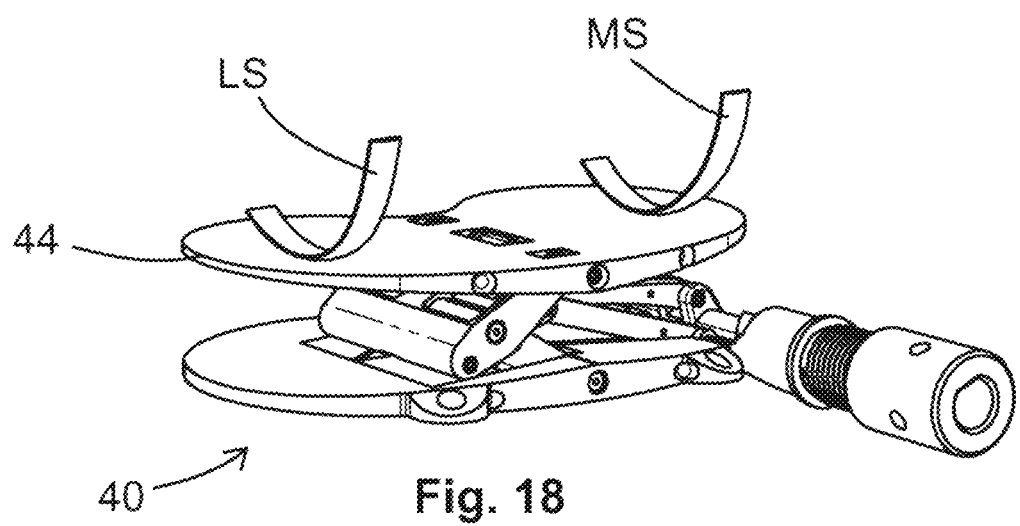
FIG. 18 is a perspective view showing plots of collected spline data superimposed on the top plate of a tensioner-balancer.
Figure 19:
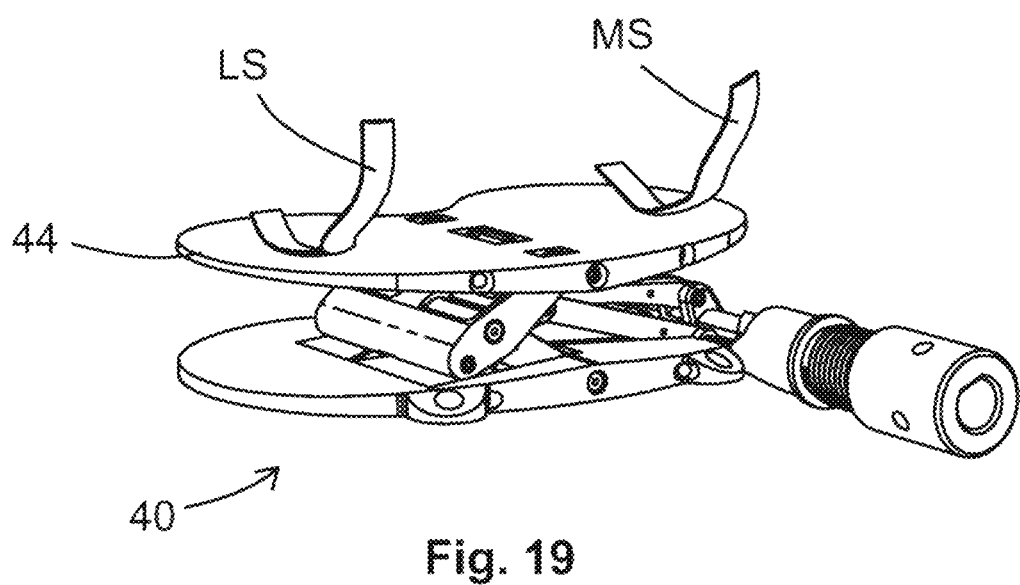
FIG. 19 is another perspective view showing plots of collected spline data superimposed on the top plate of a tensioner-balancer.

The knee joint J is then moved through its range of motion from full extension to full flexion while collecting data from the tensioner-balancer 40 and tracking markers 86, 88, 90. Specifically, the instantaneous location of the load centers LC and MC are recorded and correlated to the flexion angle of the knee joint (as determined from the tracking marker data). The recorded data is represented by the medial spline "MS" and the lateral spline "LS" as shown in FIG. 17. FIGS. 18 and 19 show the splines superimposed on the top plate of the tensioner-balancer 40. FIG. 18 illustrates idealized or nominal shape splines. FIG. 19 illustrates splines indicative of discontinuities, "notching", articular irregularities and incongruencies which may be found in an actual or pathological knee joint J. The splines may be characterized by two or more points (a Starting point and Terminal point, with zero or more Intermediary points in between), each with a location (defined by cartesian or polar coordinates relative to a fixed reference point defined by tracker on the tensioner-balancer baseplate), a direction, and a first and second derivative. Each spline point may also have an associated flexion angle and load. Given the datum of the tibia cut surface, and the fact that the tensioner balancer is fixed relative to the tibia and fixed relative to the tibia cut surface, the tracking system is functional with tracker 86 or 90 individually, or using both synchronously.

The spline information may be used to select an appropriate endoprosthetic, specifically a femoral component. Multiple femoral components of different sizes and articular surface profiles may be provided, and the one which has the best fit to the splines MS, LS may be selected for implantation. Alternatively, the spline information may be used to generate a profile for manufacture of a patient-specific femoral component.

Figure 20:
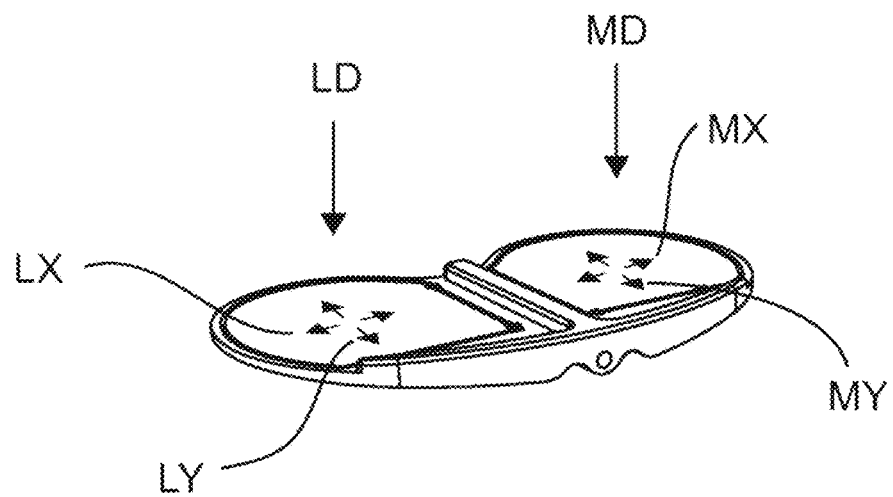
FIG. 20 is a diagram showing a tensioner-balancer labeled with data parameters.
Figure 21:
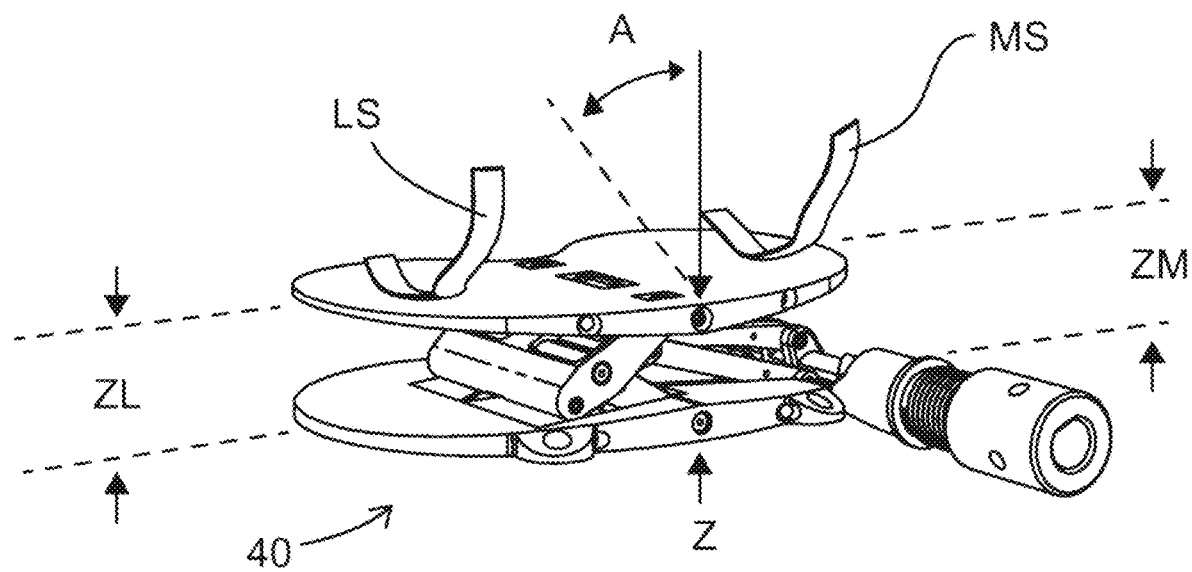
FIG. 21 is a diagram showing a knee joint and tensioner-balancer labeled with data parameters.
Figure 22:
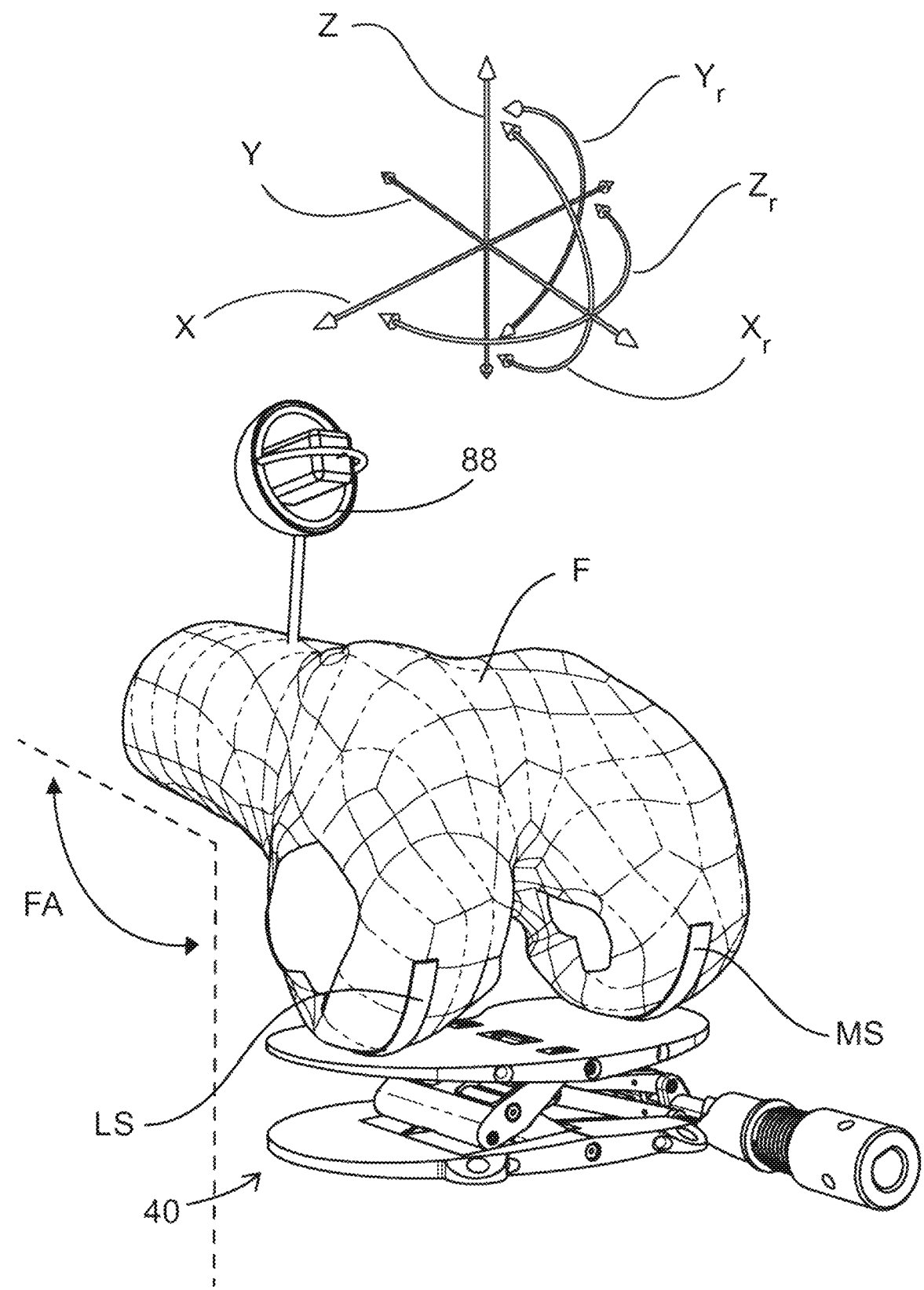
FIG. 22 is a diagram showing a knee joint and tensioner-balancer labeled with data parameters.

The spline information may be used in conjunction with other information to determine appropriate cutting planes for the femur F. For example, the back surface 28 of the femoral component 14 has a known relationship to the articular surface 30. The desired final location and orientation of the articular surface 30 is known in relation to the top plate 44 of the tensioner-balancer 40, which serves as a proxy for the tibial component 12. The final location of the tibial component 12 is known in relationship to the position of the tibial tracking marker 90. Finally, the actual orientation and location of the femur F in relation to the other parts of the joint J is known from the information from the femoral tracking marker 88. Using appropriate computations, the orientation and location of the cutting planes of the femur F can be calculated and referenced to the position the tensioner-balancer 40 or its tracker 86, or referenced to the position of the tibia or its tracker 90. With reference to FIGS. 20-22, it will be understood that the tensioner-balance 40 and associated tracking apparatus may be used to collect the following data related to the knee joint: distraction height "Z" of the top plate 44, tilt angle "A" (i.e., varus-valgus) of the top plate 44), medial and lateral distraction heights "ZM", "ZL" (e.g., derived from the top plate distraction height and top plate tilt angle), the medial and lateral spline data, the position of the contact points of the femur F on the top plate (medial-lateral and anterior-posterior) (MX, MY, LX, LY), the distraction load on the medial and lateral condyles (MD, LD), the knee joint flexion angle "FA", and the abovementioned 6-DoF position data for each tracking marker (X, Y, Z position and Xr, Yr, Zr rotation).

FIG. 23 is a chart illustrating how the real-time data from the tensioner-balancer 40 and the tracking markers can be recorded, with multiple data channels are parameters being recorded for each time step.

In collecting the spline information and tracking information, it is helpful to make reference to one or more positional datums. Each datum is a 6 DoF reference (e.g. position and orientation about three mutually perpendicular axes). The datum may refer to a geometrical construct as well as a virtual software construct.

Figure 24:
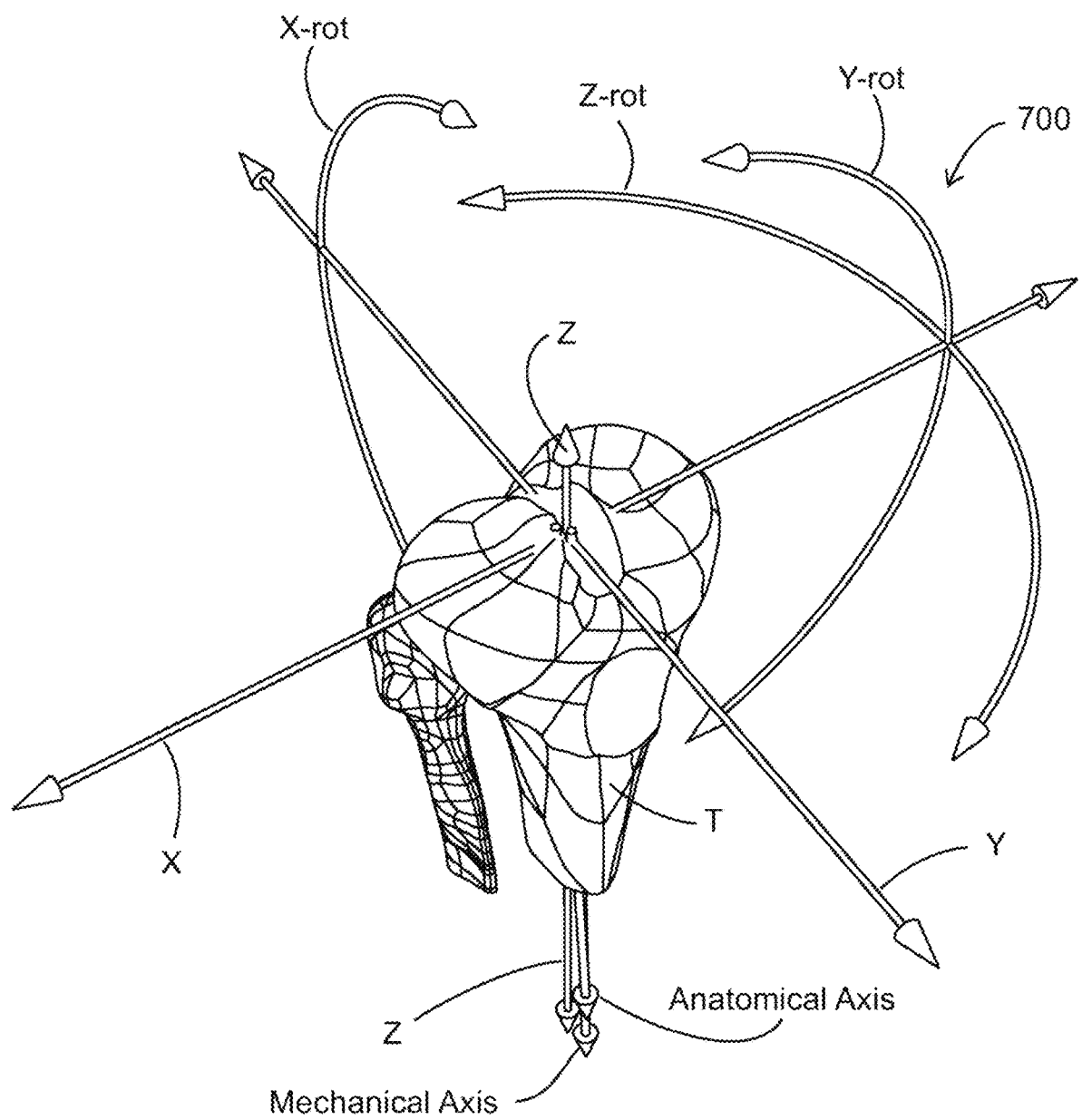
FIG. 24 is a perspective view of a tibia having a reference datum superimposed thereupon.

FIG. 24 shows an example of a datum 700 superimposed on a tibia T. As illustrated, the datum 700 is a coordinate framework with X, Y, and Z axes, as well as rotations about each of those three axes. Some respects of the position and orientation of the datum 700 relative to the tibia T may be arbitrary selected. In one example, the Z-axis may be positioned in a predetermined relationship to a known anatomical reference such as the tibia anatomical axis or tibia mechanical axis. The XY plane may be positioned normal to the Z axis and intersecting the tibia at the position of an actual or assumed tibial plateau cutting plane, or oriented at some defined angular displacement relative to an actual or assumed tibia cutting plane. Thus positioned, the datum 700 provides a reference for measurements using the tracking markers and/or the tensioner-balancer 40.

Figure 25:
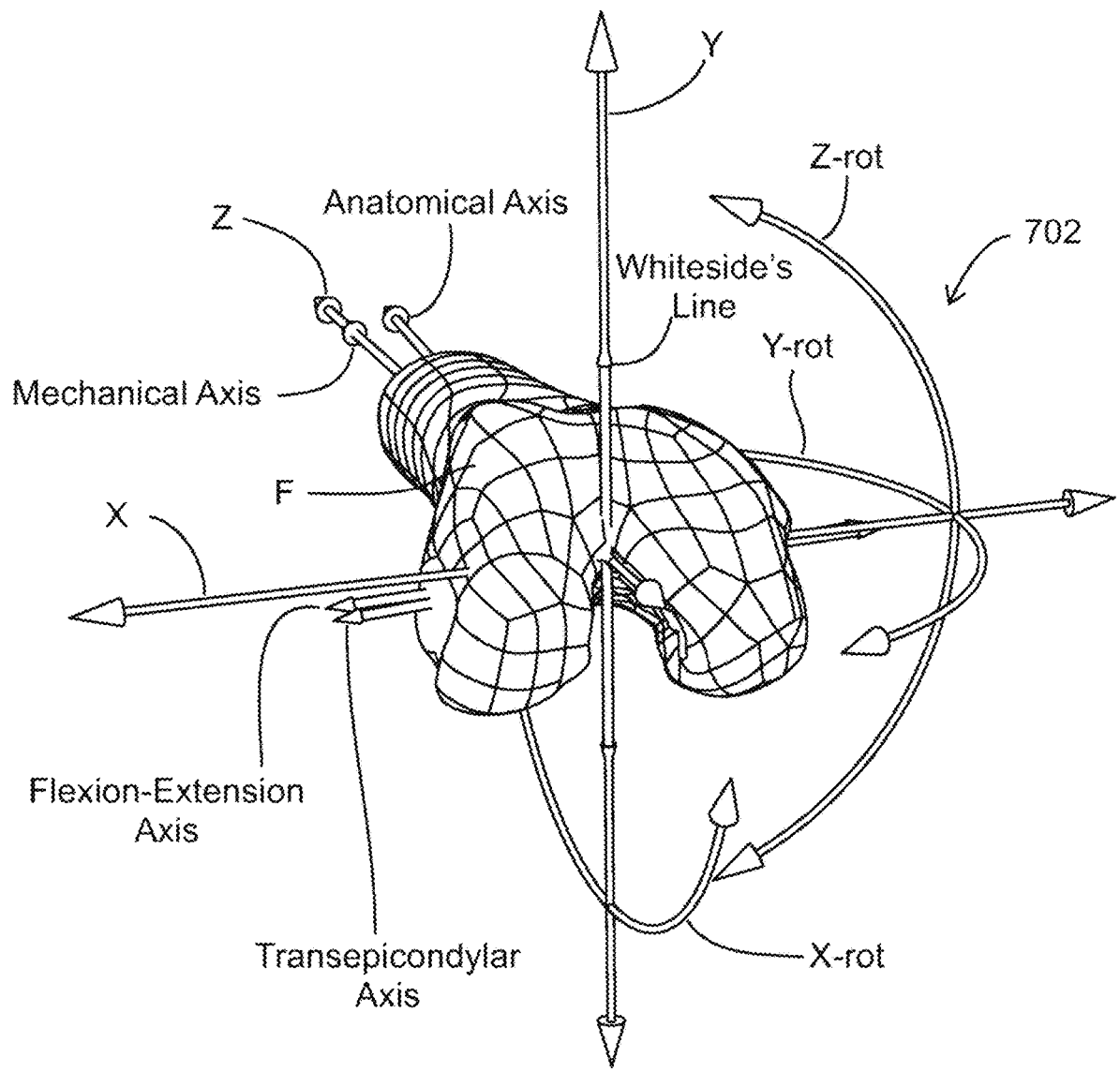
FIG. 25 is a perspective view of a femur having a reference datum superimposed thereupon.

FIG. 25 shows an example of a datum 702 superimposed on a femur F. As illustrated, the datum 702 is a coordinate framework with X, Y, and Z axes, as well as rotations about each of those three axes. Some respects of the position and orientation of the datum 702 relative to the femur F may be arbitrary selected. In one example, the Z-axis may be positioned in a predetermined relationship to a known anatomical reference such as the femur anatomical axis or femur mechanical axis. The XY plane may be positioned normal to the Z axis. Longitudinally, the XY plane may be positioned, for example intersecting an anatomical reference such as Whiteside's line. Thus positioned, the datum 702 provides a reference for measurements using the tracking markers and/or the tensioner-balancer 40.

Figure 26:
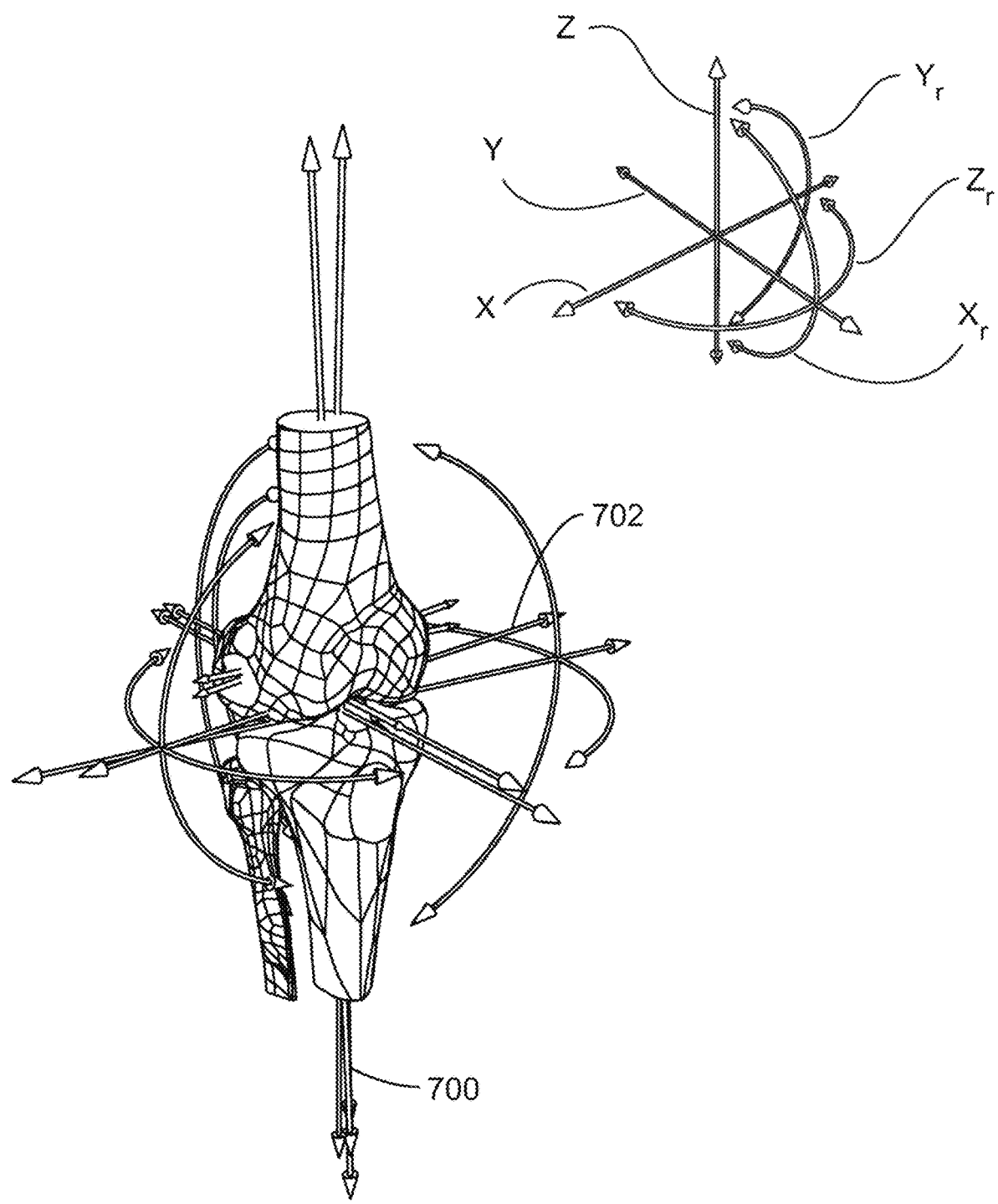
FIG. 26 is a perspective view of a knee joint having reference datums superimposed thereupon.

FIG. 26 shows the assembled knee joint J with the two datums 700, 702. For measurement and computational purposes, one of the datums may be designated a "primary" datum, with the remaining data is being designated as "secondary" datums. In one example, the datum 700 associated with the tibia T may be designated a primary datum. With the position and orientation of the datum 700 known in space (i.e., from tracking marker information), the position and orientation of the datum 702 associated with the femur F may be reported as a relative position and orientation to the datum 700 (primary data).

In another example, and arbitrary primary datum 704 may be positioned at arbitrary predetermined location outside of the body. With the position and orientation of the primary datum 704 known in space, the position and orientation of the datum 700 associated with the tibia T (considered a secondary datum in this case) may be reported as a relative position and orientation to the datum 704. In this example, the position and orientation of the datum 702 associated with the femur F would also be considered a secondary datum and would be reported as a relative position and orientation to the datum 704.

Figure 27:
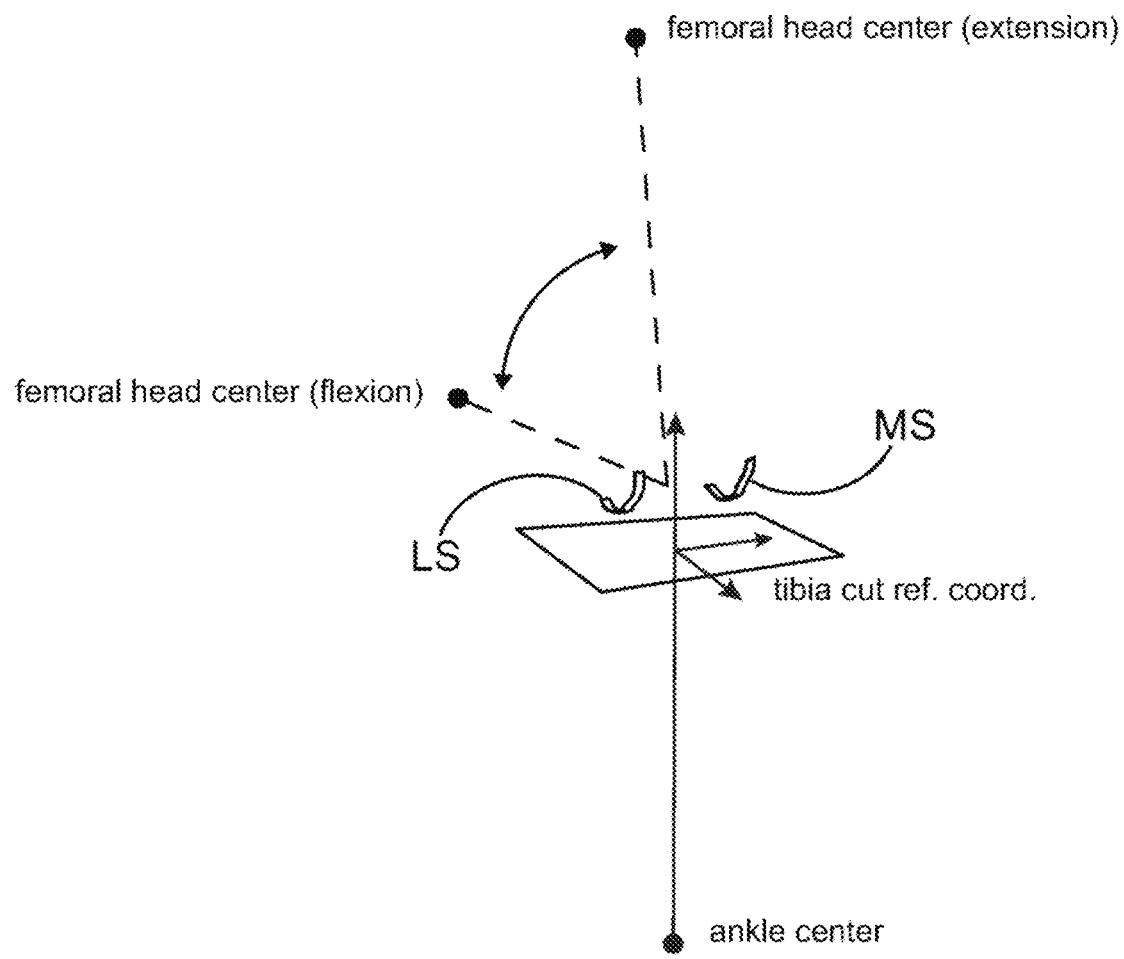
FIG. 27 is a diagram illustrating data collected by tensioner-balancer and tracking markers.
Figure 28:
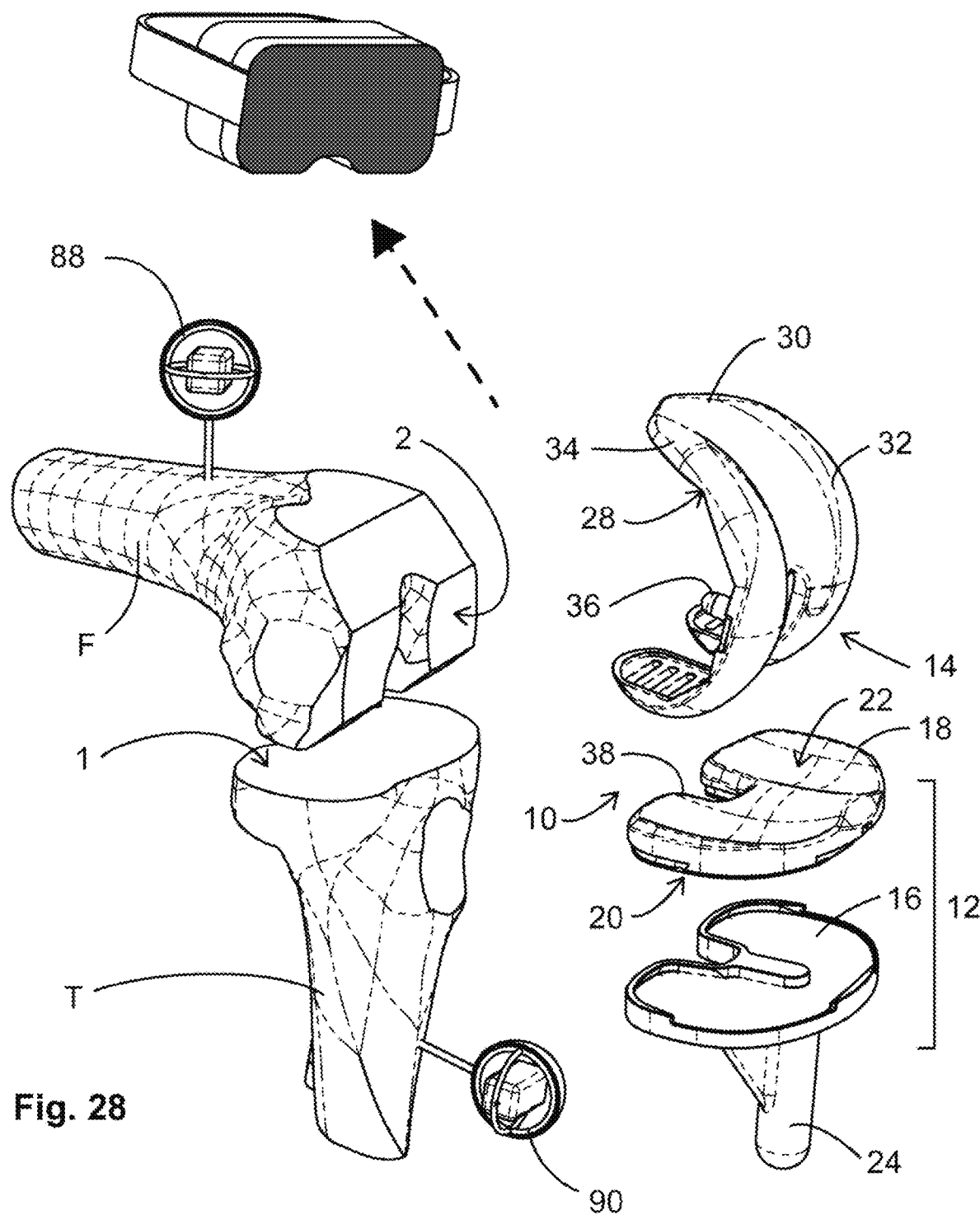
FIG. 28 is a perspective view of a human knee joint in conjunction with an exploded view of an endoprosthesis.
Figure 29:
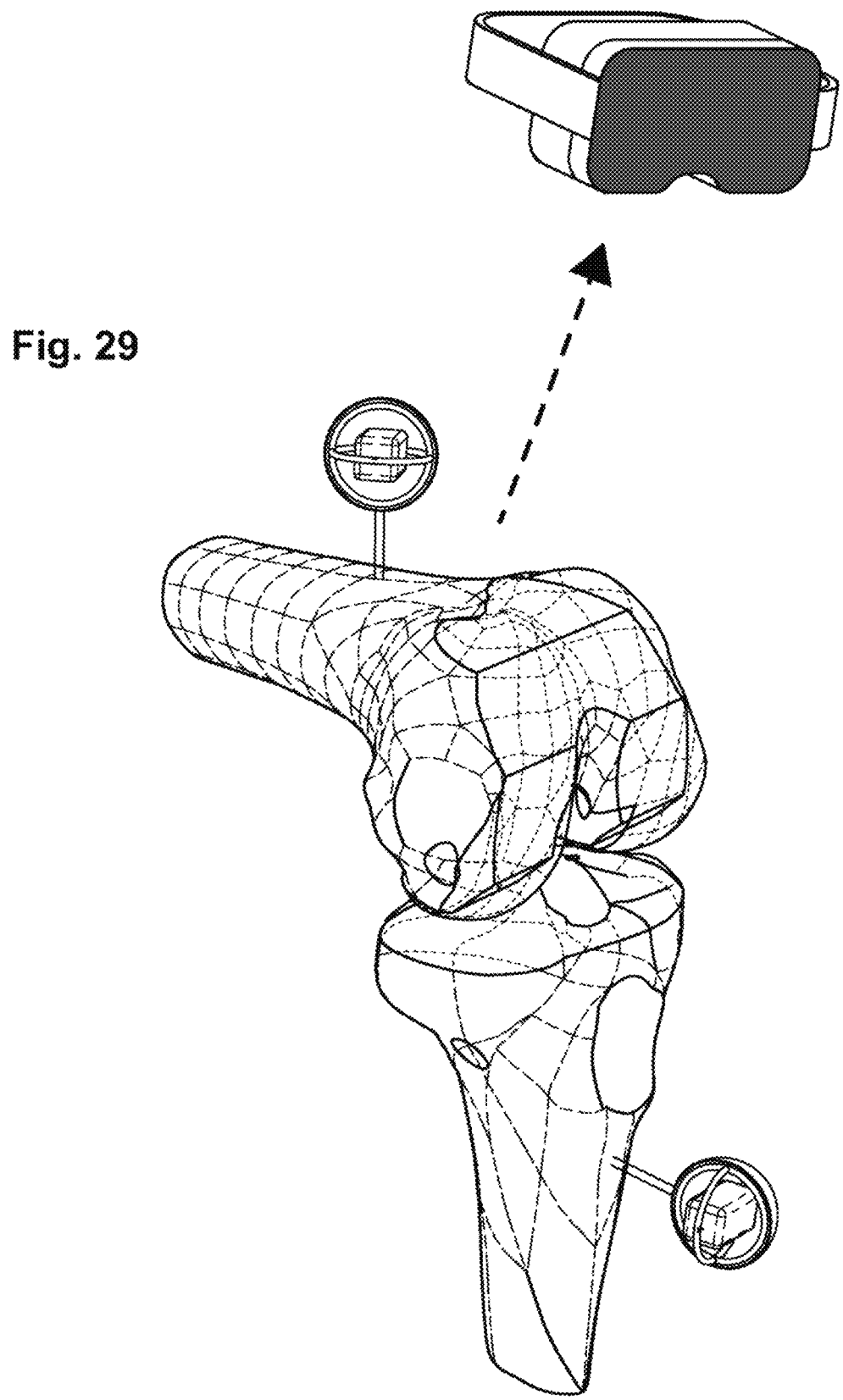
FIG. 29 is a perspective view of a human knee joint showing proposed cutting planes, in conjunction with a mixed reality display device.

FIG. 27 illustrates the organization of the data collected by the tracking markers in the tensioner-balancer 40. It can be seen that the overall modeling of the complex 3D knee geometry can be reduced for practical purposes to a relatively small set of elements including: tibial plateau cut plane, the medial and lateral splines, the position of the medial and lateral spine contacts on the tibial plateau cut plane, and axis or vector passing from the ankle center through the tibial plateau cut plane, and a femoral axis passing through the femoral head.

A nominal distal femoral cutting plane 2 (FIG. 30) may be determined by anatomical analysis using known anatomical references and techniques. For example, this plane 2 could be uniformly spaced away from and parallel to the tibial cutting plane 1 (i.e., a nominal cut). Alternatively, this plane 2 could be at an oblique angle to the tibial cutting plane 1, in one or more planes (i.e., simple or compound tilted cut, potentially usable as a corrective cut).

Figure 30:
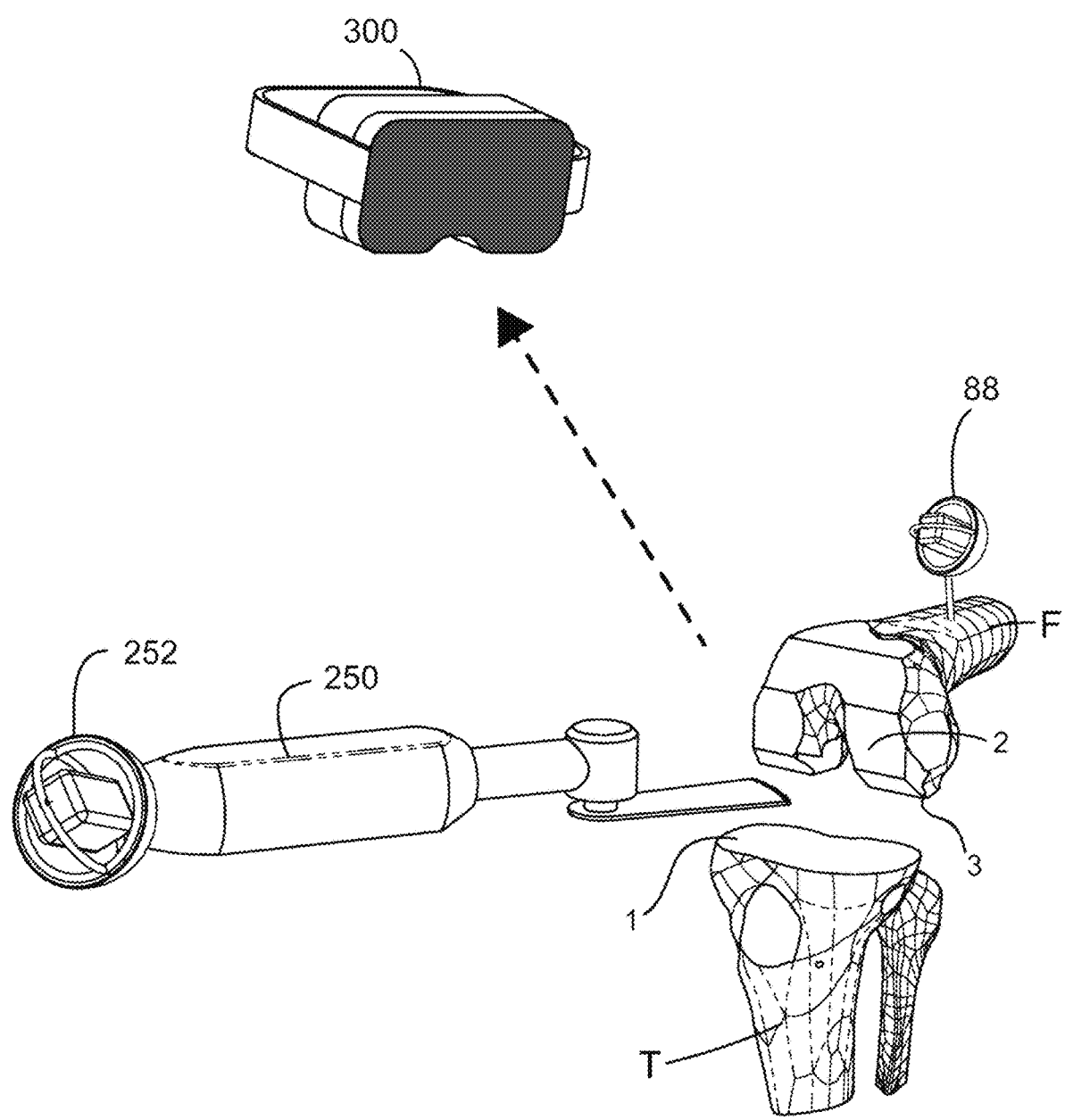
FIG. 30 is a perspective view of a human knee joint in conjunction with a mixed reality display device and an instrumented bone saw.

Information from the tensioner-balancer 40 and tracking markers may be used with hand-held equipment. Once the cutting planes are determined, the tracking markers 86, 88, or 90 may be used to guide a bone saw 250 equipped with a tracking marker 252 to make the distal femoral cut 2 at appropriate angle and location, as depicted in FIG. 30. In this context, the cutting plane (or a portion thereof) defines a computed tool path. This guidance is possible because intercommunication between the bone saw 250 and the associated tracking marker 252 will give the relative position and orientation of the bone saw 250 to that tracking marker. The cutting guidance may be provided in the form of information displayed on the remote display 84 described above. For this purpose, 2-way data communications may be provided between and among the bone saw 250 (or other surgical instrument), the tracking markers 86, 88, or 90, and the remote display 84.

Figure 31:
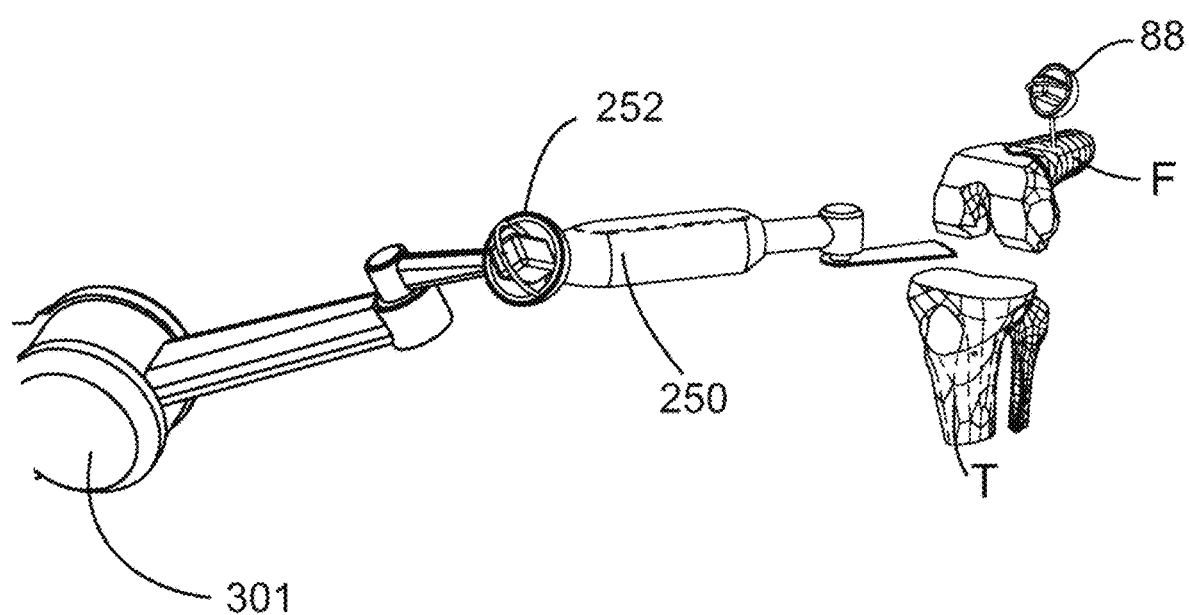
FIG. 31 is a perspective view of a human knee joint in conjunction with an instrumented bone saw coupled to a robot.

It should be noted that the bone saw 252 can be guided with reference to only a single tracking marker 88 coupled to the femur F. Alternatively, the cutting guidance (optionally along with other information, such as the virtual future position of the drilled holes and implants used) may be displayed on a body-worn display providing 2D or 3D graphics or providing a holographic heads-up display with an information panel (e.g., a Virtual Reality or augmented reality or mixed reality headset 300). Alternatively, the cutting guidance may be provided to a conventional robot 301 (FIG. 31) to which the bone saw is mounted.

Figure 32:
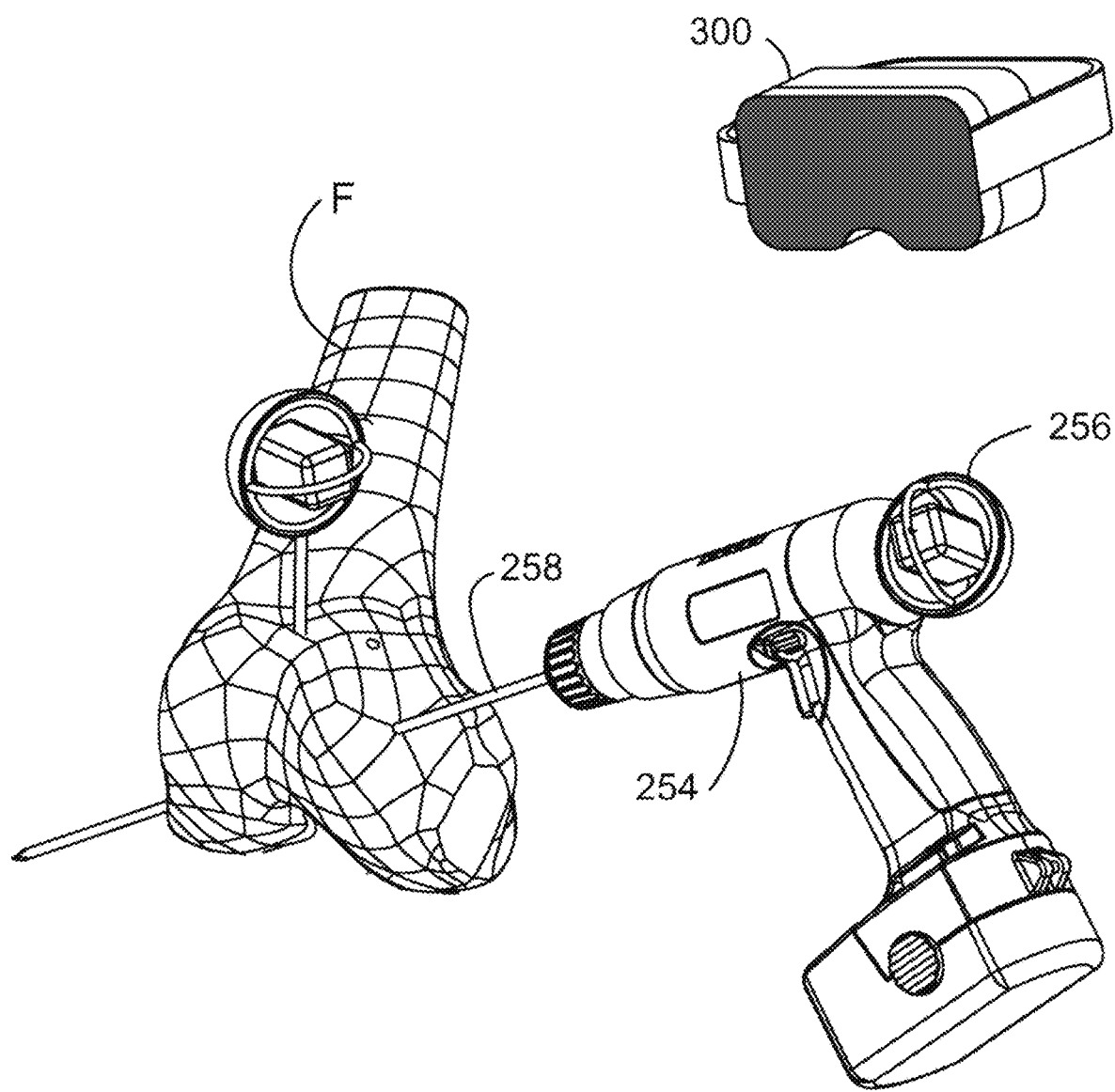
FIG. 32 is a perspective view of a human knee joint in conjunction with a mixed reality display device and an instrumented drill.
Figure 33:
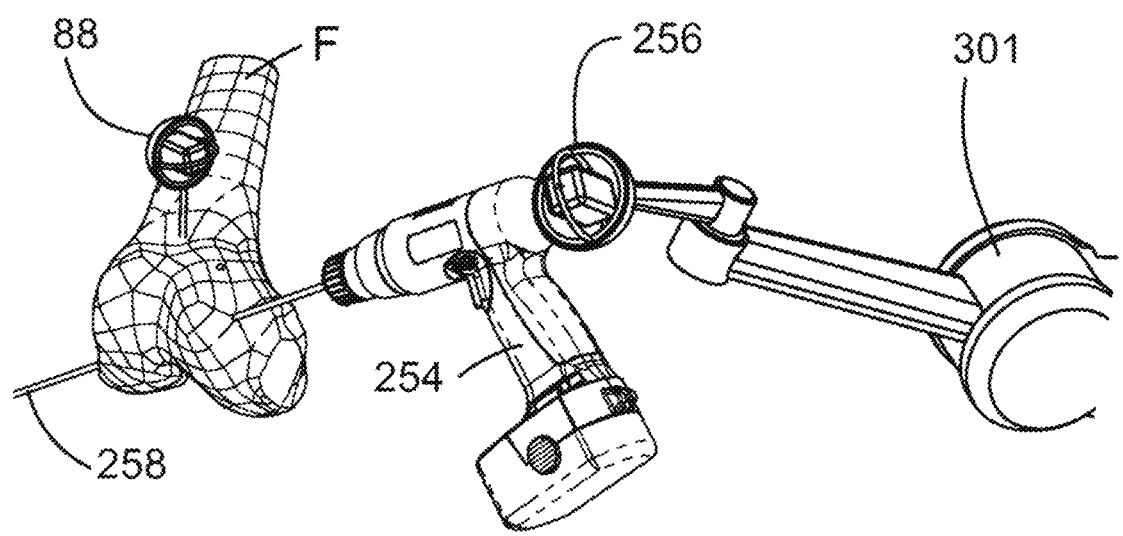
FIG. 33 is a perspective view of a human knee joint in conjunction with an instrumented drill coupled to a robot.

Information from the tensioner-balancer 40 and tracking markers may optionally be used for drilling holes, for example to anchor tensile elements. Referring to FIG. 32, once a position of a hole to be drilled is determined, the tracking markers 86, 88, or 90 may be used to guide a cordless drill 254 equipped with a tracking marker 256 to drill a hole, with the drill bit 258 extending an appropriate angle. In this context, the hole to be drilled (or a portion thereof) defines a computed tool path. Guidance along the tool path is possible because intercommunication between the cordless drill 254 and the tracking marker 256 will give the relative position and orientation of the cordless drill 254 to those markers. The drilling guidance may be provided in the form of information displayed on the remote display 84 described above. For this purpose, two-way data communications may be provided between and among the cordless drill 254 (or other surgical instrument), the tracking markers 86, 88, or 90, the actuating instrument 70, and the remote display 84. It should be noted that the drill 254 can be guided with reference to only a single tracking marker 88 coupled to the femur F. Alternatively, the drilling guidance (optionally along with other information, such as the virtual future position of the drilled holes and implants used) may be displayed on a body-worn display providing 2D or 3D graphics or providing a holographic heads-up display with an information panel (e.g., a Virtual Reality or augmented reality or mixed reality headset 300). Alternatively, the drilling guidance may be provided to a conventional robot 301 (FIG. 33) to which the bone saw is mounted.

Figure 34:
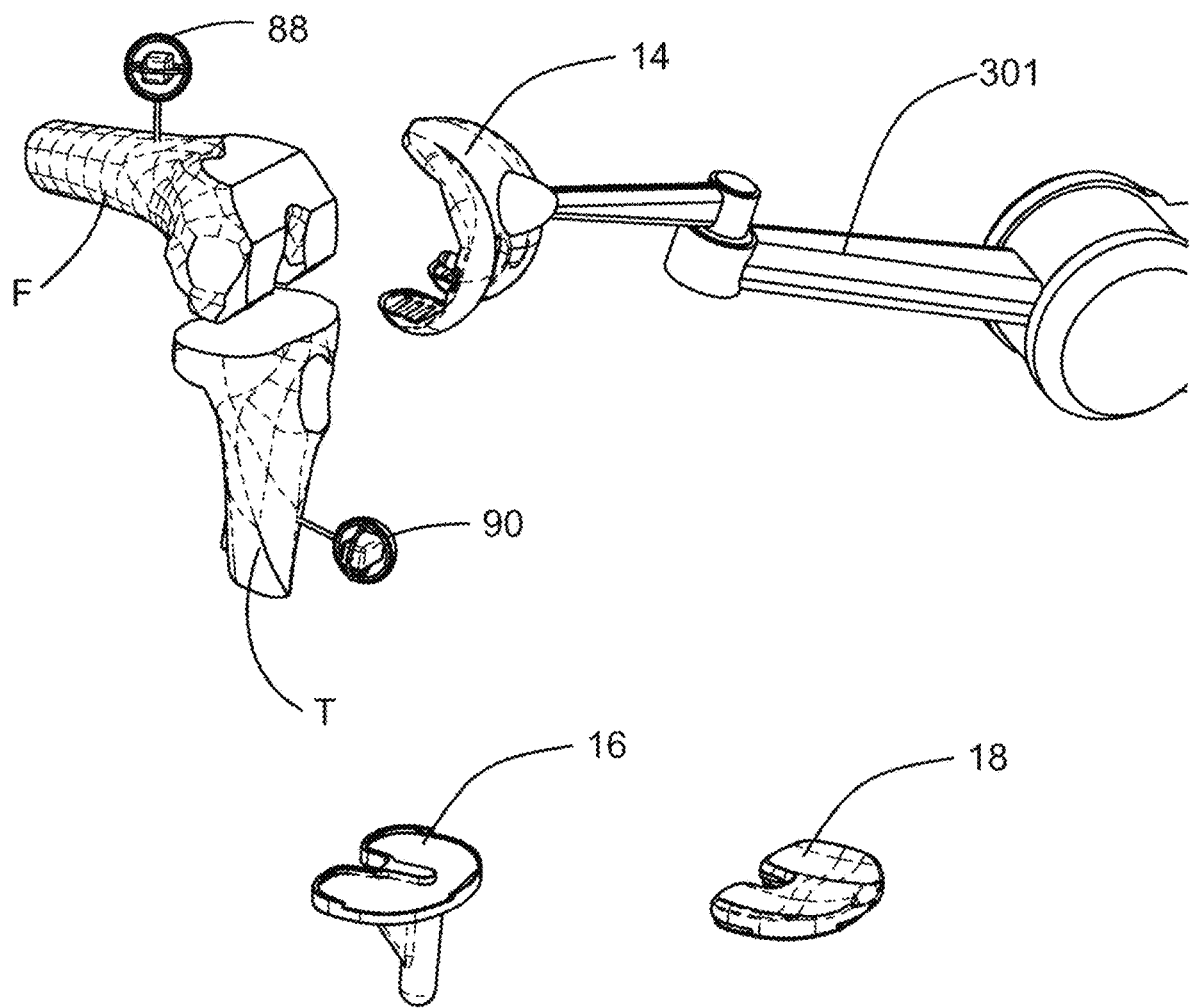
FIG. 34 is a perspective view of a human knee joint in conjunction with a robot that is manipulating an endoprosthesis.

Information from the tensioner-balancer 40 and tracking markers may optionally be used for automated placement of components. Referring to FIG. 34, the tracking markers 86, 88, or 90 may be used to guide a robot 301 to implant one or more of the endoprosthetic components into the knee joint J, such as the tibial tray 16, insert 18, and/or femoral component 14 to which the bone saw is mounted.

Figure 35:
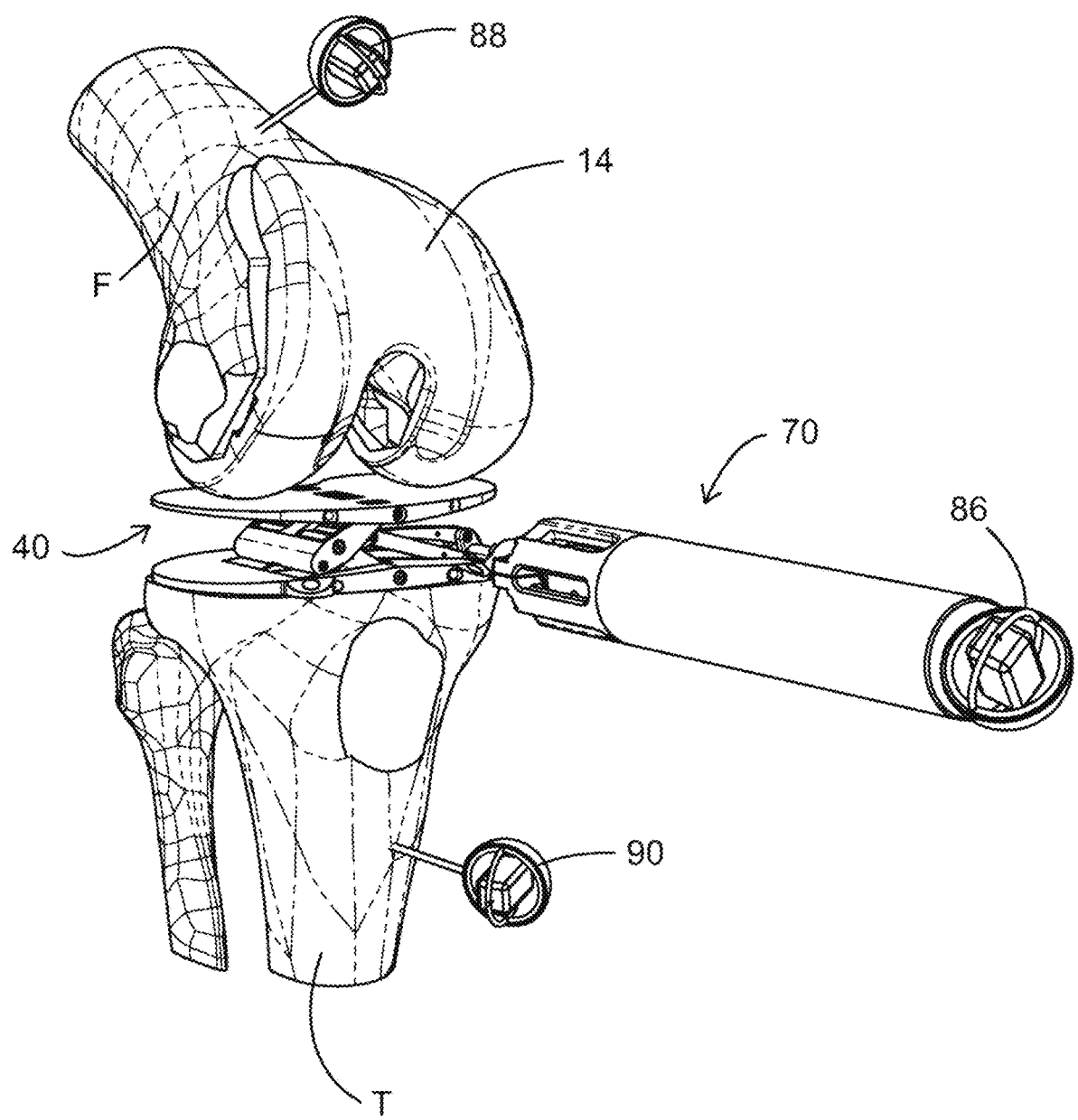
FIG. 35 is a perspective view of a human knee joint having a trial endoprosthesis device implanted, in conjunction with a tensioner-balancer.

As seen in FIG. 35, the tensioner-balancer 40 may be used with a trial implant (femoral component 14) to collect data and evaluate the femoral component 14.

In addition to retaining the patients' PCL in a knee arthroplasty, it may be augmented (reinforced) using one or more artificial tensile members. The term "tensile member" as used herein generally refers to any flexible element capable of transmitting a tensile force. Nonlimiting examples of known types of tensile members include sutures and orthopedic cables. Commercially-available tensile members intended to be implanted in the human body may have a diameter ranging from tens of microns in diameter to multiple millimeters in diameter. Commercially-available tensile members may be made from a variety of materials such as polymers or metal alloys. Nonlimiting examples of suitable materials include absorbable and resorbable polymers, nylon, ultrahigh molecular weight polyethylene ("UHMWPE") or polypropylene titanium alloys, or stainless steel alloys. Known physical configurations of tensile members include monofilament, braided, twisted, woven, and wrapped. Optionally, the tensile member may be made from a shape memory material, such as a temperature-responsive or moisture-response material.

Figure 36:
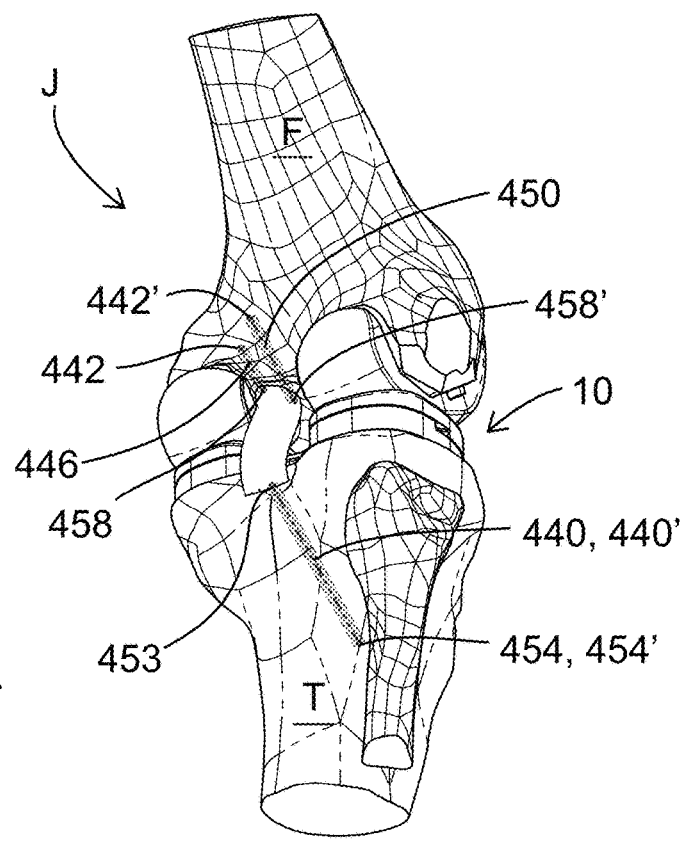
FIG. 36 is a perspective view of a posterior aspect of a human knee joint having a posterior cruciate ligament reinforced by artificial tensile member.
Figure 37:
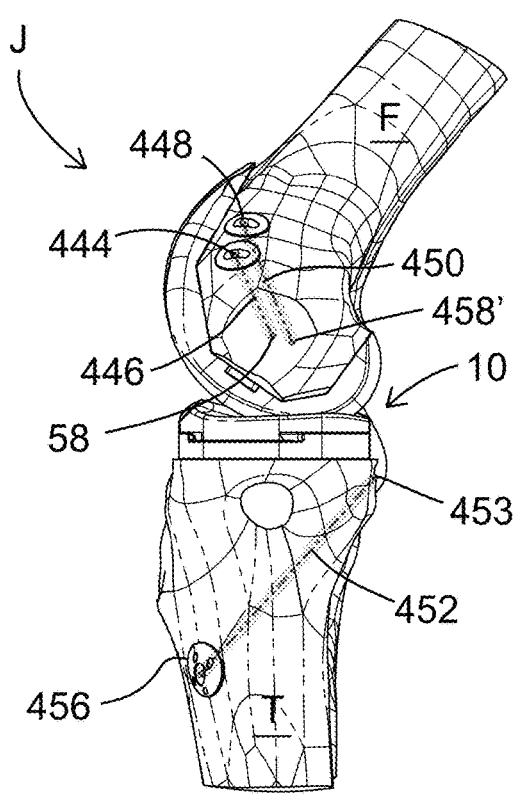
FIG. 37 is a view of the medial aspect of the human knee joint of FIG. 36.

FIGS. 36 and 37 illustrate a tensile member passing through transosseous passaged formed in bone (e.g., by drilling), fixed by anchors, and routed across the posterior aspect of a human knee joint J. The tensile member replaces or augments or reinforces or tethers the PCL.

In the illustrated example, two tensile members are present, referred to as first and second tensile members 440, 440' respectively.

The first tensile member 440 has a first end 442 secured to the femur F on the outboard side thereof, by a first anchor 444. (With reference to this example, the terms "inboard" and "outboard" are used to describe locations relative to their distance from the meeting articular surfaces of the joint J. For example, the endoprosthetic 10 would be considered "inboard" of the joint J, while the anchor 444 would be considered "outboard"). The first tensile member 440 passes through a first femoral passage 446 formed in the femur F, exiting the inboard side of the femur F.

The second tensile member 440' has a first end 442' secured to the femur F on the outboard side thereof, by a second anchor 448. The second tensile member 440' passes through a second femoral passage 450 formed in the femur F, exiting the inboard side of the femur F.

The first and second tensile members 440, 440' span the gap between femur F and tibia T and enter a tibial passage 452 at an inboard side. The first and second tensile members 440, 440' pass through the tibial passage 452 at a single entry 453, exiting the outboard side of the tibia T. Second ends 454, 454' of the first and second tensile members 440, 442' are secured with a third anchor 456.

The term "anchor" as it relates to elements 444, 448, and 456 refers to any device which is effective to secure a tensile member passing therethrough. Nonlimiting examples of anchors include washers, buttons, flip-anchors, adjustable loop devices, fixed loop devices, interference screw devices, screw plates, ferrules, swages, or crimp anchors.

The tensile members 440, 440' can be routed through or along the PCL.

Figure 38:
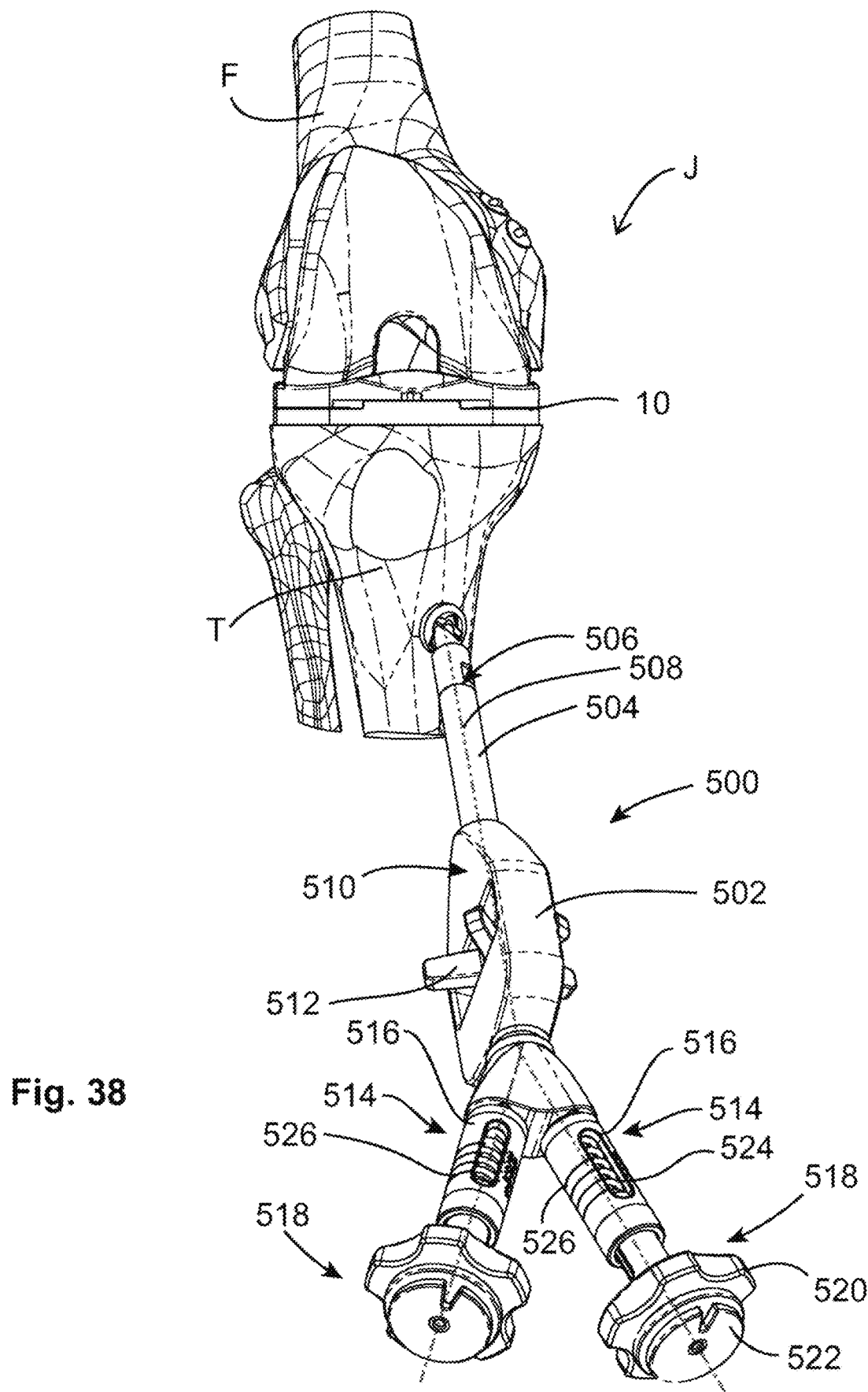
FIG. 38 is a view of the anterior aspect of the human knee joint in combination with an instrument for tensioning an artificial tensile member.

FIG. 38 illustrates an exemplary insertion instrument 500 which may be used to insert, tension, and activate swage-type anchors. The basic components of the insertion instrument 500 are a body 502, a stem 504 extending from the body 502 and having an anchor connection mechanism 506 disposed at a distal end thereof, a hollow pushrod 508 extending through the stem 504 and slidably movable between retracted and extended positions, and a driving mechanism 510 for moving the pushrod 508 between retracted and extended positions. The stem 504 and the pushrod 508 may be rigid or flexible.

In the illustrated example, the driving mechanism 510 comprises an internal threaded mechanism which is manually operated by a star wheel 512.

A tensioner 514 is part of or connected to the insertion instrument 500. It has a housing 516. A shuttle assembly 518 including an adjustment knob 520 and a grooved spool 522 is received inside the housing 516. A compression spring 524 is captured between the shuttle assembly 518 and the housing 516. The shuttle assembly 518 can translate forward and aft relative to the housing 516 in response to rotation of the adjustment knob 520.

In use, a first end of a tensile member 440 passes through the hollow interior of tensioner 514 and is secured to the spool 522. The tension applied to the tensile member 440 may be indicated, for example, by observing the position of the shuttle assembly 518 relative to a calibrated scale 526 on the housing 516. When a suitable final tension is achieved, the star wheel 512 may be operated to actuate the pushrod 508, swaging the tensile member 440 and fracturing the breakaway structure of the anchor. In the illustrated example, two separate tensioners 514 are provided, allowing the tension of each of the tensile members to be set independently.

In one example procedure where two tensile members are used, a first provisional tension is applied to the first tensile member and a second provisional tension is applied to the second tensile member. The second tensile member may have the same or different tension at the first tensile member. Next, the provisional tensions evaluated to determined if they are suitable. In response to the evaluation, they may be increased or decreased. Finally, the anchor may be swaged to secure the tensile members and finalize the tension. In one example, the tension may be from about 0 N (0 lb.) to about 220 N (50 lb.)

Figure 39:
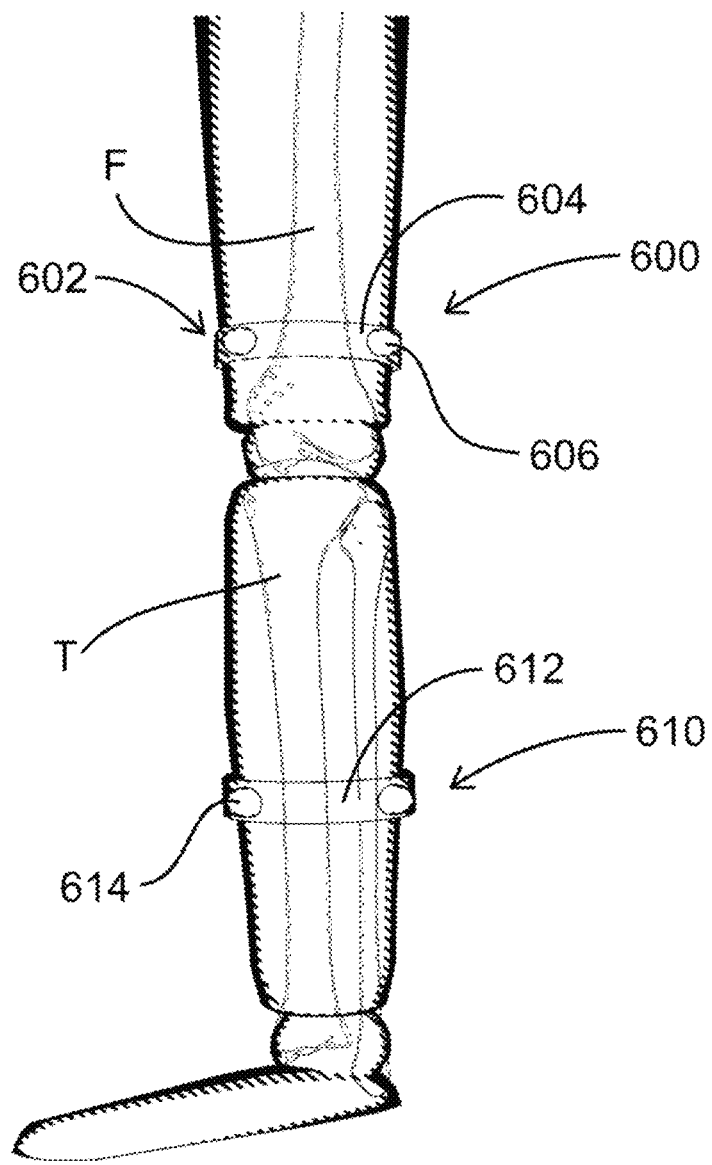
FIG. 39 is a schematic diagram of a human leg having a body-worn tracking system placed thereon.

In addition to or as an alternative to other devices and methods described herein, the range of motion of the knee joint J may be evaluated using non-image-based devices and methods. As it is used, the phrase "image-based" refers to common preoperative and intraoperative imaging techniques including x-ray, fluoroscopy, radiograph, CT scan, CAT Scan, MRI, or digital registration. For example, FIG. 39 illustrates schematically a human leg which has been instrumented for measurement using a body-worn tracking apparatus, indicated generally at 600.

At least one upper leg garter 602 is secured around the upper leg. The upper leg garter 602 includes a band 604 configured to be secured around the upper leg, for example by elastic tension, or an adjustable mechanism such as hook and loop fasteners or a buckle (not shown). It further includes at least one tracking marker 606. The tracking marker 606 is operable such that, using an appropriate receiving device, the position and orientation of the receiving device relative to the tracking marker 606 may be determined by receipt and analysis at the receiving device of signals transmitted by the tracking marker 606.

As illustrated, the six degree-of-freedom, local NAV, non-line-of sight tracking marker 606 may be operable to determine six degree-of-freedom position information in a local coordinate system. For example, it may be configured as an inertial navigation device including one or more accelerometers and gyroscopic elements capable of providing angular rate information and acceleration data in 3D space.

Figure 40:
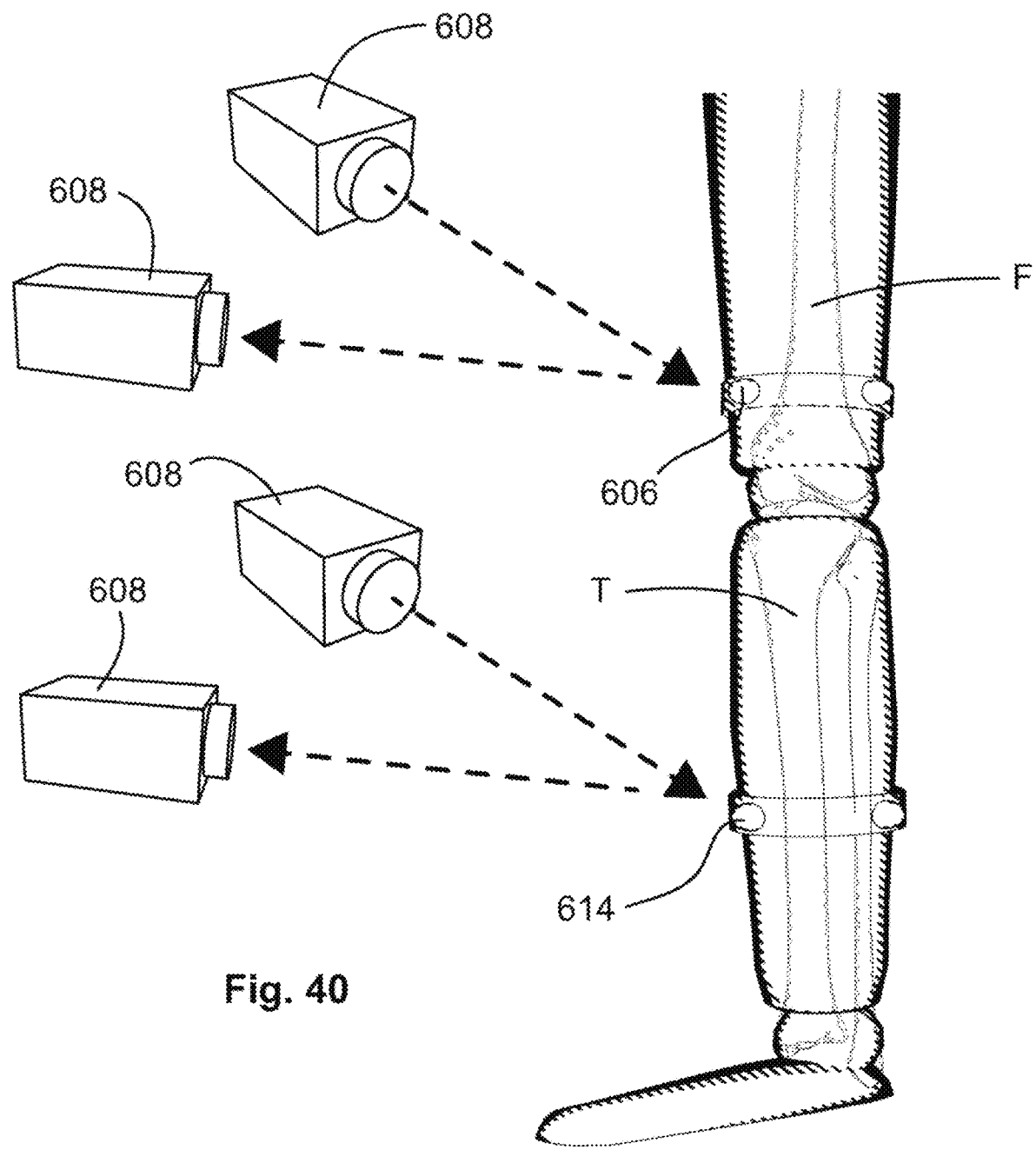
FIG. 40 is a schematic diagram of a human leg having a body-worn tracking system placed thereon, in conjunction with tracking sensors.
Figure 41:
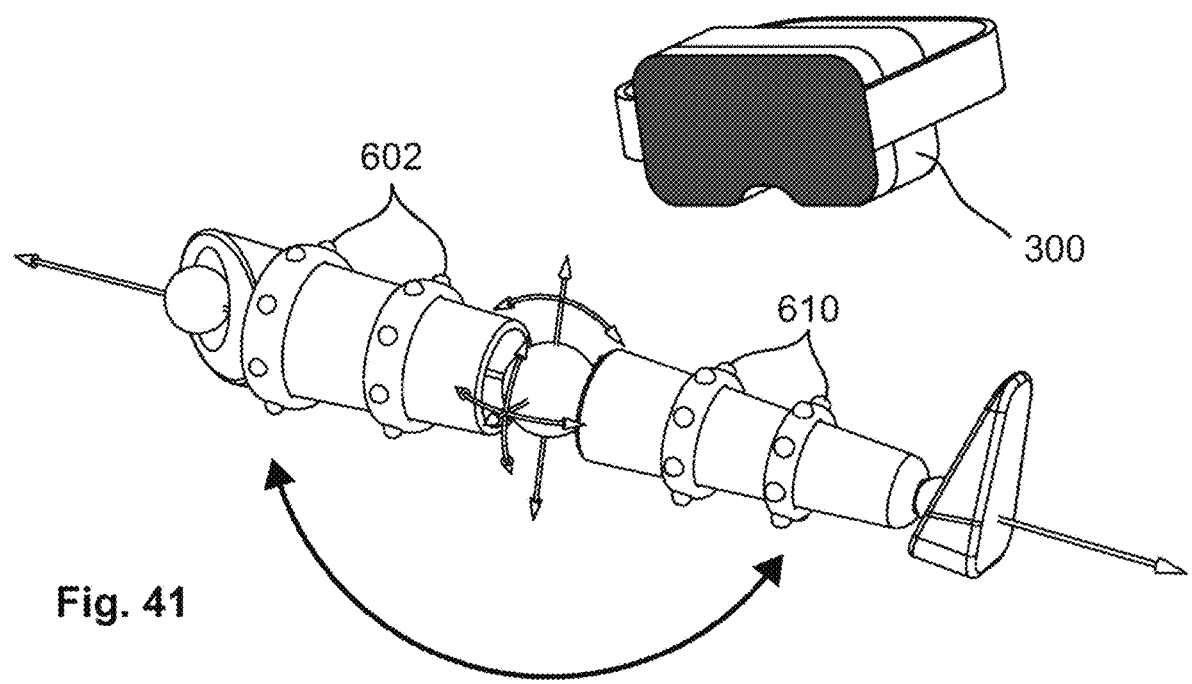
FIG. 41 is a schematic diagram of a human leg having a body-worn tracking system thereon, in conjunction with a mixed reality display device, where the leg is in a extended position.
Figure 42:
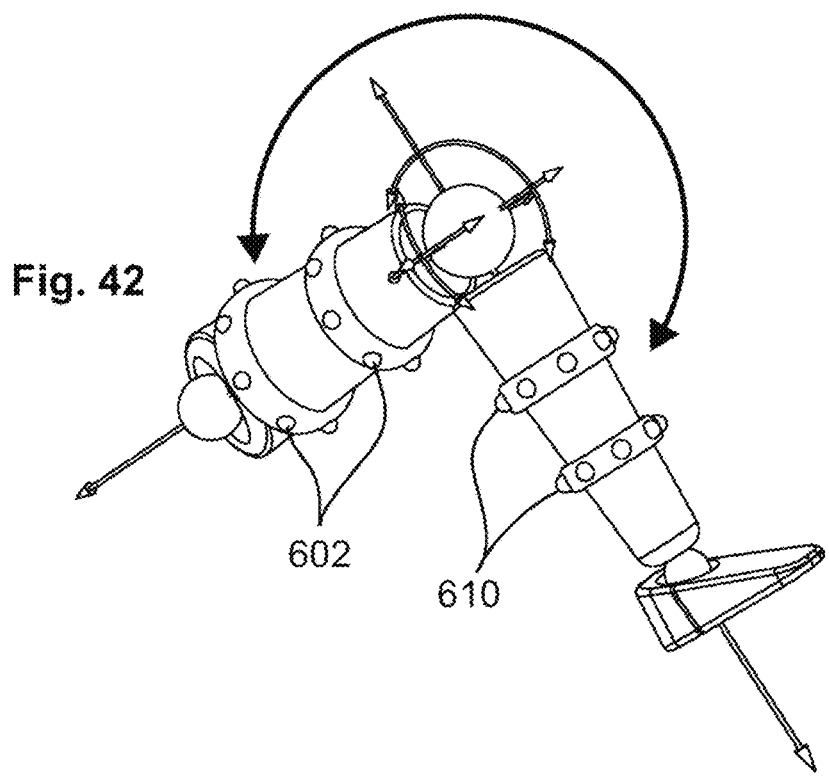
FIG. 42 is a schematic diagram of a human leg having a body-war tracking system thereon, where the leg is in a flexed position.

In an alternative embodiment shown in FIG. 40, the tracking marker 606 may include one or more tracking points which may be configured as transmitting antennas, radiological markers, or other similar devices. Tracking markers 606 and appropriate receivers are known within the state-of-the-art. Nonlimiting examples of known tracking methods include LIDAR, time-of-flight sensors, infrared detectors, moiré patterns, and ultrasonic trackers. FIG. 40 illustrates exemplary receiving devices 608.

By securing the upper leg garter 602 around the upper leg, the tracking marker 606 would have a substantially fixed position and orientation relative to the femur F.

At least one lower leg garter 610 is secured around the lower leg. The lower leg garter 610 is of similar or identical construction to the upper leg garter 602. It includes a band 612 and at least one tracking marker 614. Thus secured, the tracking marker 614 would have a substantially fixed position and orientation relative to the tibia T.

Once the upper and lower leg garters 602, 610 are secured, they may be placed in data communication with a suitable electronic receiving device by a wired or wireless connection. Appropriate processors and software may be provided for interpretation of the signals from the garters 602, 610.

Appropriate processing of signals generated by the garters 602, 610 may be used to generate kinematics of the knee joint J in numeric and/or graphical form.

The received data may be displayed on a display providing 2D or 3D graphics or providing a holographic heads-up display with an information panel (e.g., a Virtual Reality or augmented reality or mixed reality headset 300), or on a conventional display such as a computer monitor (not shown).

The body-worn tracking apparatus 600 can be used for several kinds of measurement, which may be referred to herein as "dynamic imaging". For example, it can be used to quantify the range of motion of the knee joint J, i.e., by measuring the flexion angle from the patient's most extended position to the patient's most flexed position. In another example, the body-worn tracking apparatus 600 can be used to quantify the results of a "drawer test" in which the patient's lower leg is pulled axially away from the upper leg, by measuring the amount of deflection when a force is applied. This quantifies the "tightness" of the knee joint J. And in another example the tracking apparatus 600 can be used to pinpoint the femoral head center, the ankle center, the mechanical axes of the tibia and femur, and the knee center along with the instantaneous axis of rotation of the knee, which changes position but is traceable throughout the arc of motion.

The body-worn tracking apparatus 600 can be used preoperatively in order to evaluate the patient's normal or pathological knee. The body-worn tracking apparatus 600 can be used post-operatively in order to evaluate the results of a knee procedure. Nonlimiting examples of biological markers that may be tracked include actual range of motion, swelling in and around the joint, patellar movement. Nonlimiting examples of known methods to visualize and track the described kinematics include the drawer test, varus-valgus stress test, hyperextension, range of motion analysis, and standing-walking-running and stairstep tests.

Figure 43:
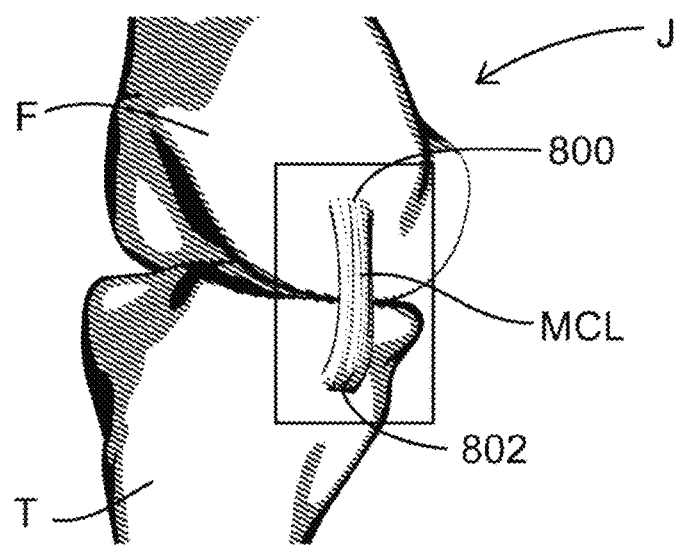
FIG. 43 is a diagram of a human knee joint showing the MCL, in an extended position.
Figure 44:
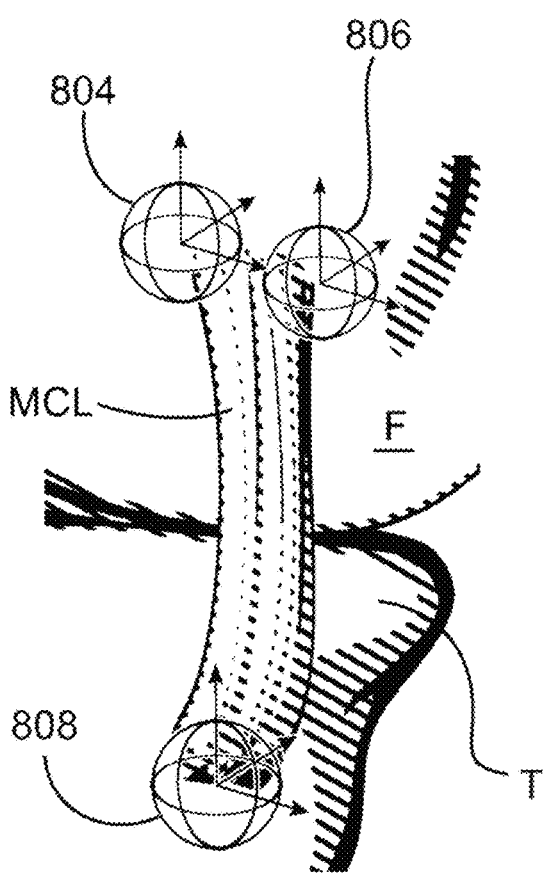
FIG. 44 is an enlarged view of FIG. 43, with virtual sockets superimposed over the MCL.
Figure 46:
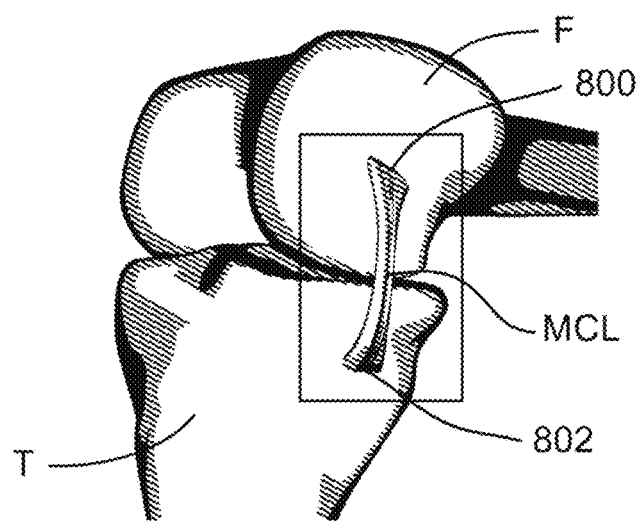
FIG. 46 is a diagram of a human knee joint showing the MCL, in a flexed position.
Figure 47:
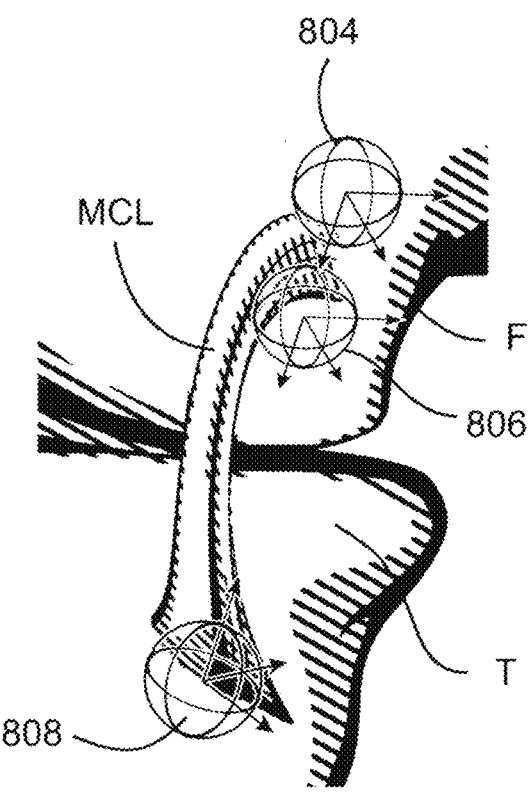
FIG. 47 is an enlarged view of FIG. 46, with virtual sockets superimposed over the MCL.

In addition to the modeling of the joint surfaces and joint kinematics described above, the inventors have discovered that the complexity and totality of the soft tissue of the knee joint J may be modeled with high fidelity producing actionable results by using a simplified construct of six-degree of freedom points with centroids, orientations, directions of momentum and acceleration, referred to as "sockets" coupled by digital or mathematically modeled tensile members representing individual ligament, tendons, ligament or tendon masses, ligament or tendon bundles, or tissue bundles having defined properties. An individual ligament or tendon can be modeled with one or more sockets for each end of the ligament. Each socket may be defined instantaneously. FIGS. 43 and 44 illustrate the MCL of human knee joint J. The MCL J is relatively broad and flat, extending some distance in the superior-inferior direction. It has a proximal end 800 that originates at the femur F and a distal end 802 having its insertion in the tibia T. FIGS. 43 and 44 show the knee J and MCL in the extended position, while FIGS. 46 and 47 show the knee J and MCL in the flexed position. It can be observed that the MCL is not purely under tension but undergo some bending during the movement. In the flexed position, the footprint of its proximal end 800 is bent over or twisted or inverted as seen in FIG. 46. It can also be observed that the complex mechanical dynamics of the MCL can be simplified for computational purposes with one or more distinct tensile members, each with programmed nonlinear stress-strain properties and definitions of starting point tangency and terminal point tangency.

Figure 45:
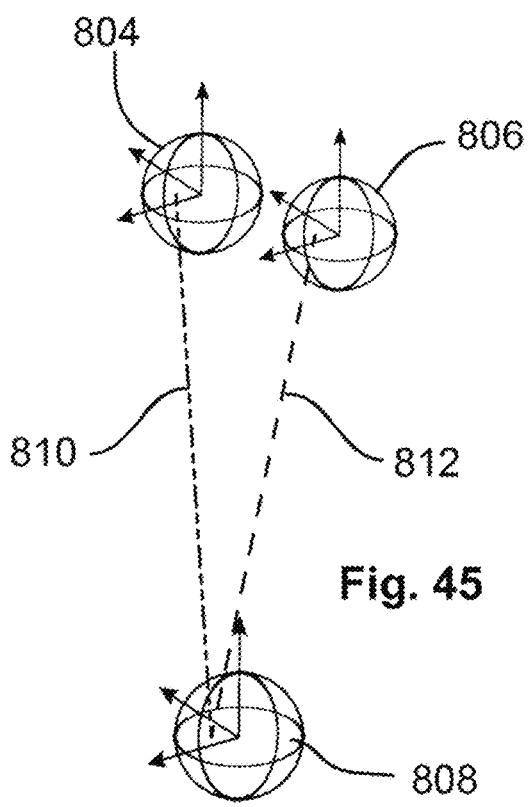
FIG. 45 is a view of the socket and tensile member virtual construct of an MCL, in the extended position.
Figure 48:
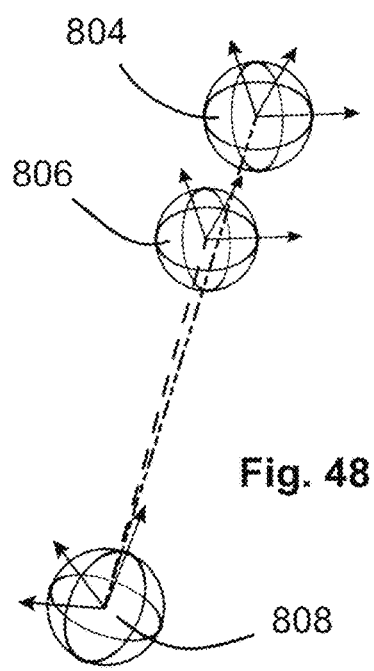
FIG. 48 is a view of the socket and tensile member virtual construct of an MCL, in the flexed position.

FIGS. 45 and 48 illustrate a modeling configuration for the MCL. In this model, a first socket 804 is disposed at the anterior portion of the proximal end 800 of the MCL. A second socket 806 is disposed at the posterior portion of the proximal end 800 of the MCL. A third socket 808 is disposed at the distal end 802 of the MCL.

As noted above, each socket is a mathematical construct which can be manipulated by conventional modeling software, including but not limited to finite element analysis. The accuracy, repeatability, and reliability of these mathematical constructs may be confirmed through empirical imaging and analysis using known techniques, including Biplanar fluoroscopy or shear wave and strain sonoelastography. Each socket defines a point in space which has properties of position in three axes e.g. X, Y, Z and orientation and three axes, e.g., X, Y, Z. Each socket may translate along any of three axes, rotate about any the three axes, or have forces or torques applied to or reacted from any of the three axes.

The modeling configuration further includes tensile members representing the MCL interconnecting the sockets. In the illustrated example, a first tensile member 810 extends from the first socket 804 to the third socket 808. A second tensile member 812 extends from the second socket 806 to the third socket 808. Each tensile member 810, 812 is associated with a set of properties i.e. a ligament stiffness, more specifically a stress versus strain curve, described in more detail below.

Figure 49:
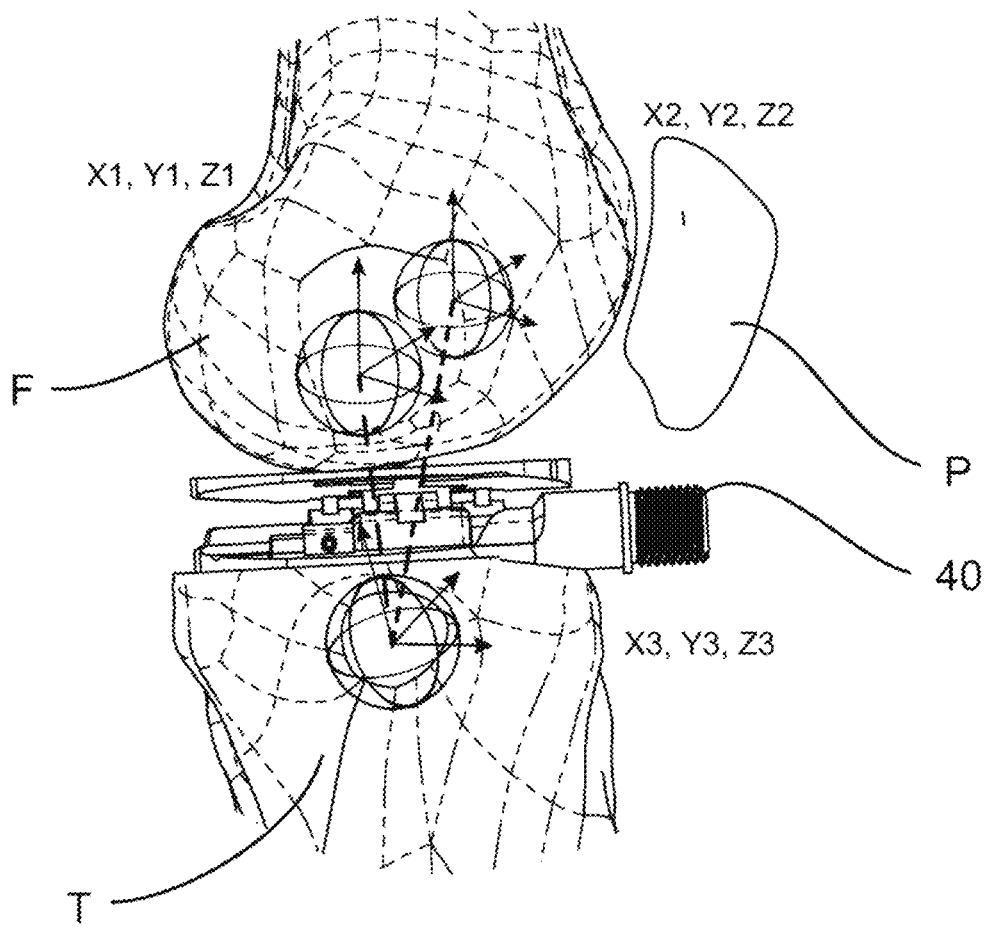
FIG. 49 is a view of a human knee joint with a tensioner-balancer inserted therein, with virtual sockets superimposed over the joint.

FIG. 49 further illustrates the mathematical socket construct overlaid onto a knee joint J having a tensioner-balancer 40 inserted therein, with the patella P in place. The socket-based model is thus also useful Intraoperatively.

Figure 50:
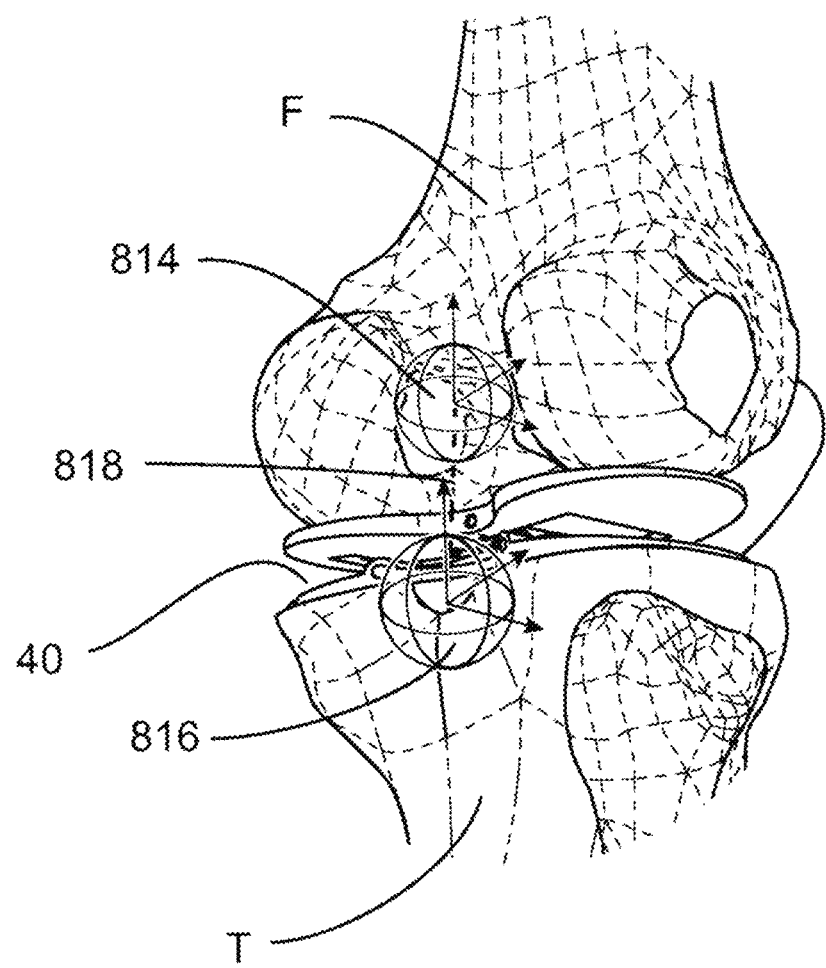
FIG. 50 is a view of the human knee joint with a tensioner-balancer inserted therein, with virtual sockets representing a PCL.

It is noted that the socket construct may be used with any soft tissue member. For example, FIG. 50 shows a pair of sockets 814, 816 and a tensile member 818 being used to model the PCL of the human knee joint J.

Figure 51:
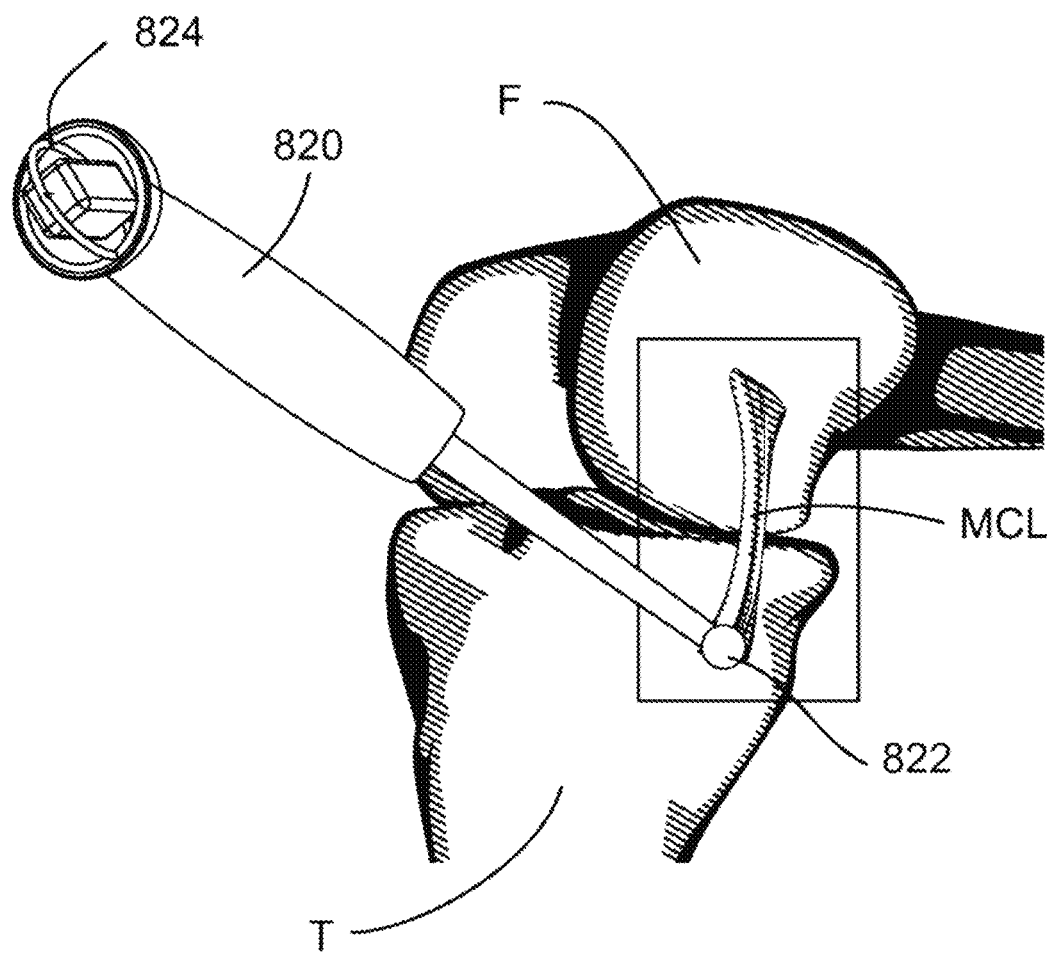
FIG. 51 is a view of the human knee joint showing an instrumented probe being used to register a position of a ligament of the joint.

The position of the sockets (or at least their initial assumed position) may be an input into the software arbitrarily, or may be measured. For example, FIG. 51 illustrates an instrumented probe 820 having a tip 822 and a tracking marker 824 as described above. The probe 820 may be used preoperatively or intraoperatively to collect actual position data of the insertion and/or origin of the soft tissue such as the MCL. This position data within be used in the software for the position of the associated socket.

Figure 52:
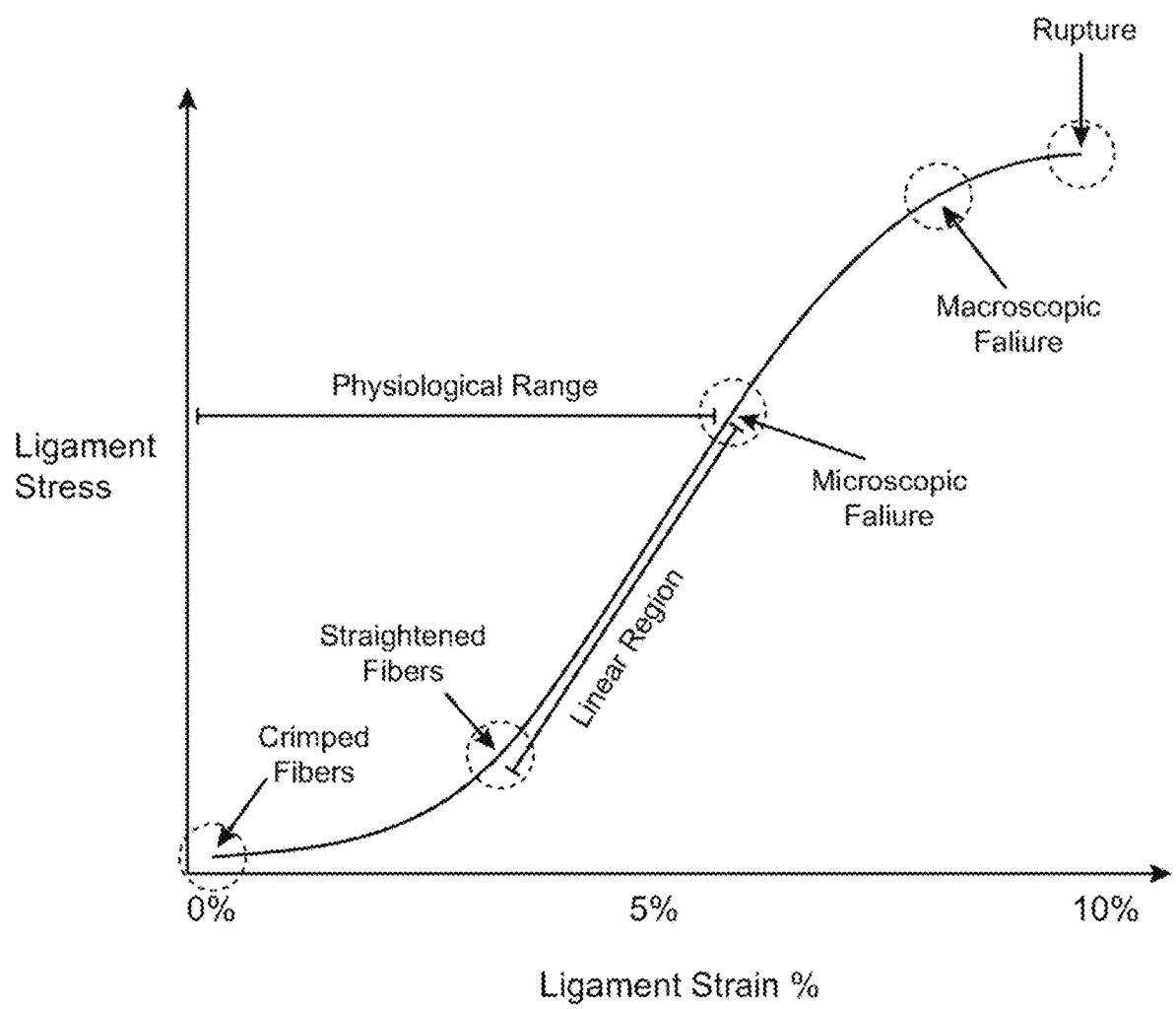
FIG. 52 is a representative stress-strain curve of a ligament of a human joint.
Figure 53:
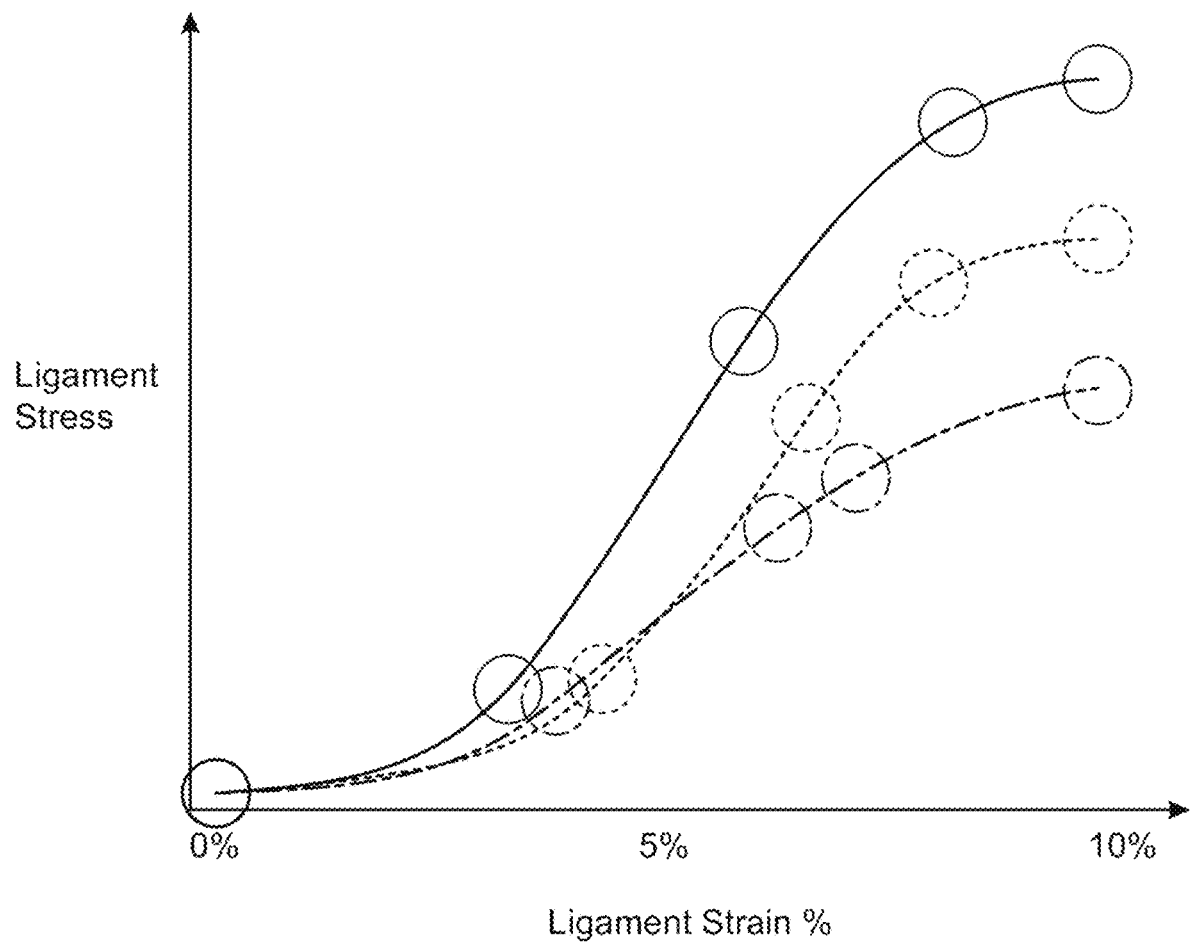
FIG. 53 is a series of stress-strain curves of human ligaments for different individuals.

FIG. 52 is a schematic diagram representing the stiffness of a human knee ligament. This is a stress-strain curve illustrating ligament percent strain on the X-axis and ligament stress on the Y-axis. Beginning at the current origin can be seen that there is an initial nonlinear range is the individual ligament fibers are strained and tend to "align" themselves from laxity to parallel paths under a very low initial tension when a load is applied (i.e. strain is applied without any resultant loading), followed by a generally linear region where the ligament is seen to behave more elastically and/or viscoelastically. As stress is increased, microscopic failures began, giving way to macroscopic failure and finally to rupture of the ligament when its breaking strength is exceeded. This curve indicates the overall characteristic of a given ligament. However, it will be understood that the specific tensile characteristics will vary for an individual patient or patient population based on numerous factors such as age, gender, body mass, physique, level of athletic training, and existence or absence of pathology. In FIG. 53, the solid line is representative of a healthy young athlete, while the dotted line is representative of an elderly person, and the dot-dash line is representative of a person having soft tissue damage.

Figure 54:
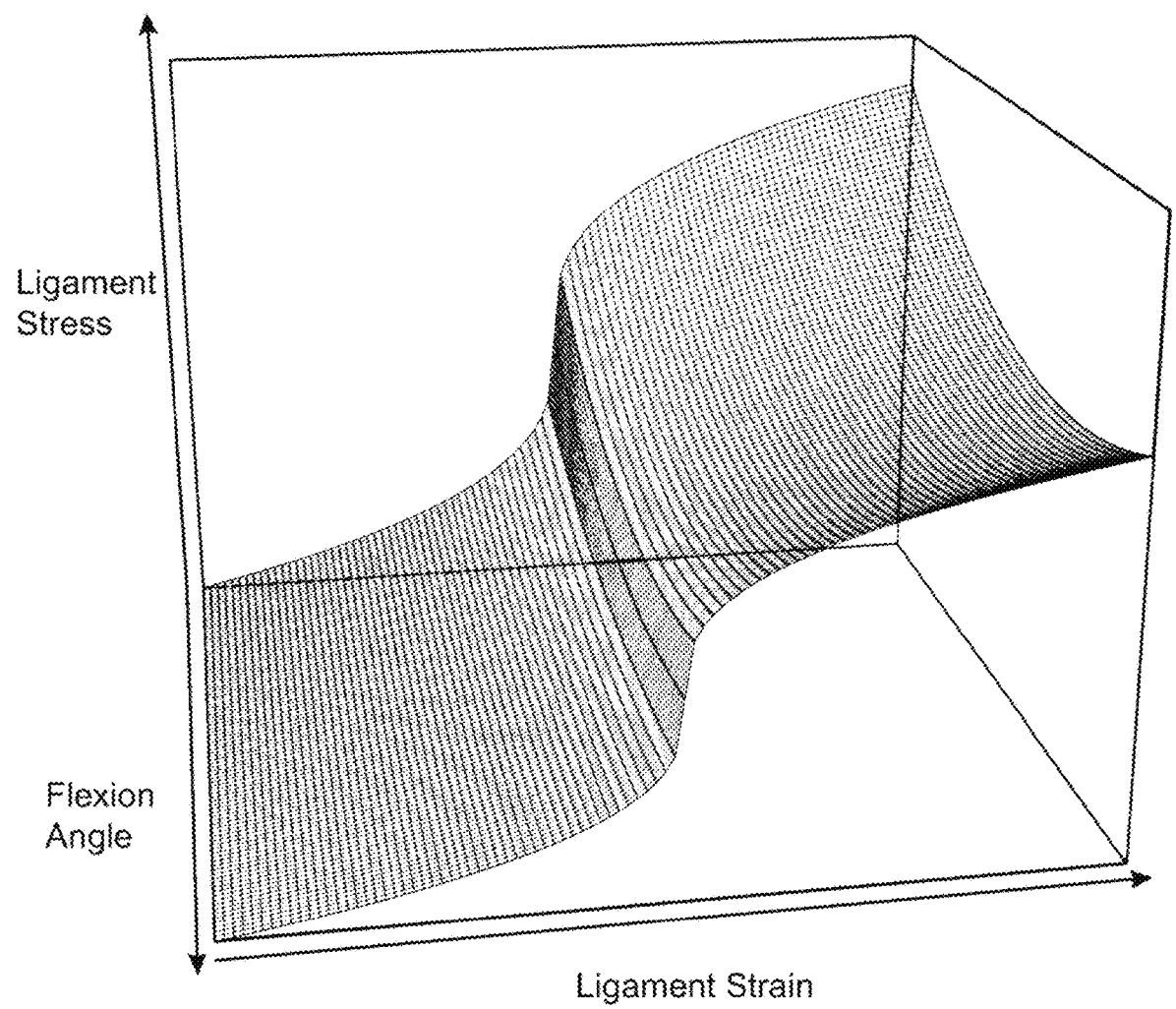
FIG. 54 is a 3D plot of stress-strain curves of human ligaments for a human knee joint of a specific individual, over a range of knee flexion angles.

It will be understood that the stress-strain characteristics are dynamic in nature and can vary with the flexion angle of the knee joint J. Referring to FIG. 54, this is a three-dimensional plot of ligament stress versus strain over a range of flexion angles. This is due to the fact that the ligaments are in fact not point to point lines, but are masses of soft tissue which engage and disengage different parts of their bone attachment "footprints" as the joint is flexed.

An example of a nonlinear equation with associated variables and coefficients:

$$y(x, z) = \left(B1 + B2 * z^f\right) \times \left[A1 + A2 \times \frac{1}{\left(1 + e^{-k*x}\right)^a}\right]$$

x=ligament length
z=flexion angle
k="stiffness factor" (affects the slope of the curve)
a="strain skew" (affects the shift of the inflection points in the Strain axis)
f="flexion power" (affects the amplitude [curviness vs flatness] of the curve through the 3rd dimension, Flexion Angle
A1=Strain Intercept
A2=Strain Coefficient
B1=Flexion Intercept
B2=Flexion Coefficient In modeling the soft tissue of a specific patient as described above, an appropriate patient specific set of intraoperative and postoperative parameters for a plan of care may be developed. The parameters may be influenced or selected by populational and demographic data such as age, gender, stature, pathology, disease state, activity level, outcome goals, and lifestyle. The parameters described may include the total distraction load to be used for balancing the knee, patient-specific medial and lateral contact loads, patient-specific prosthesis geometry and sizing, flexion-angle-specific loads, ligament-specific loads, or position and tension applied to any implanted tensile members for ligament augmentation or reinforcement. Patient-specific parameters will also be influenced by a patient's individual anatomy and kinematics, and may be used to generate three-dimensional plots driven by nonlinear equations. An appropriate three-dimensional plot may also be proposed by a teaching and learning system. A Machine Learning system may be allowed to compute and define patient specific stress and strain characteristics for patient specific analysis.

Figure 55:
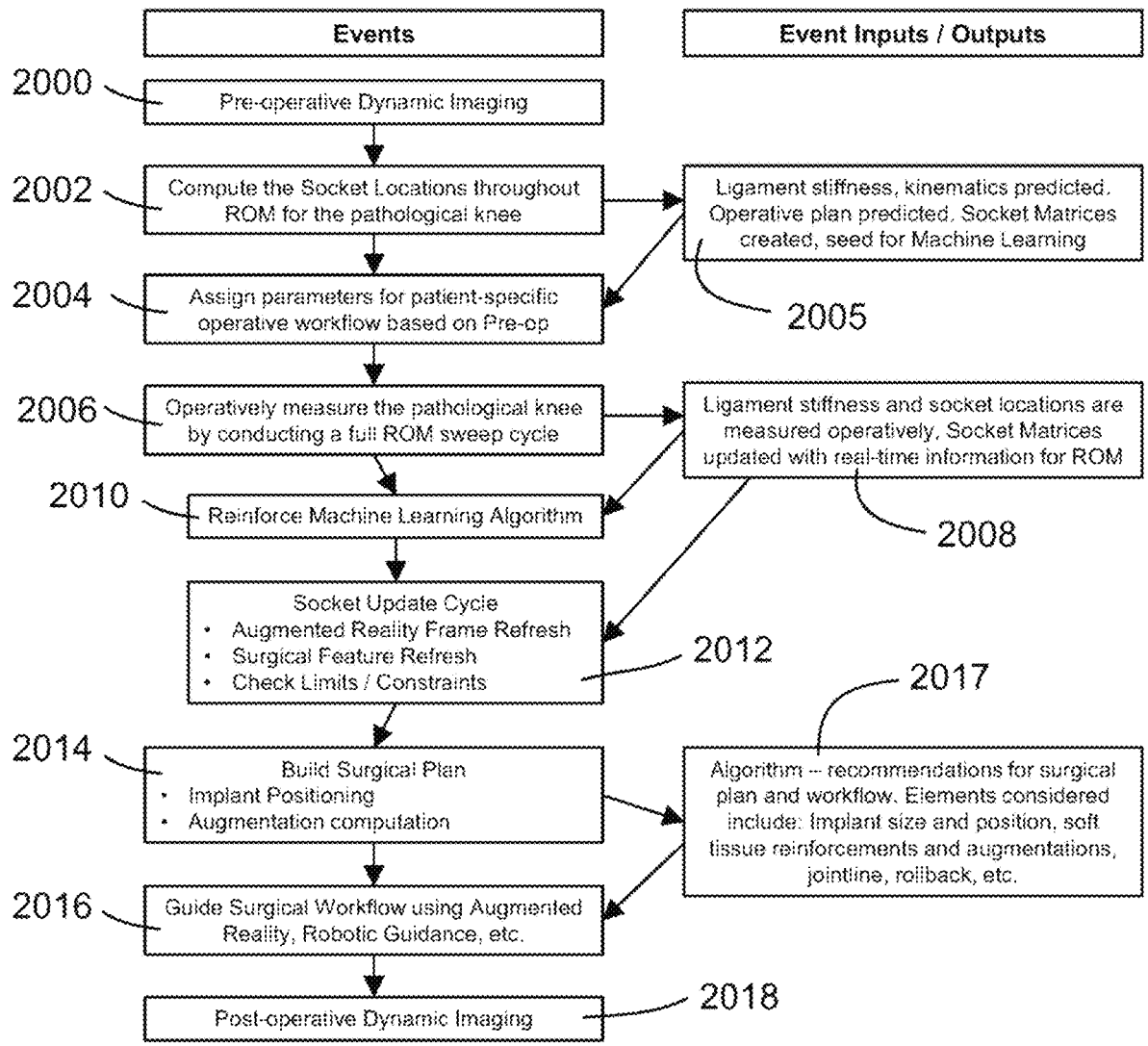
FIG. 55 is a flowchart of a example surgical process.
Figure 56:
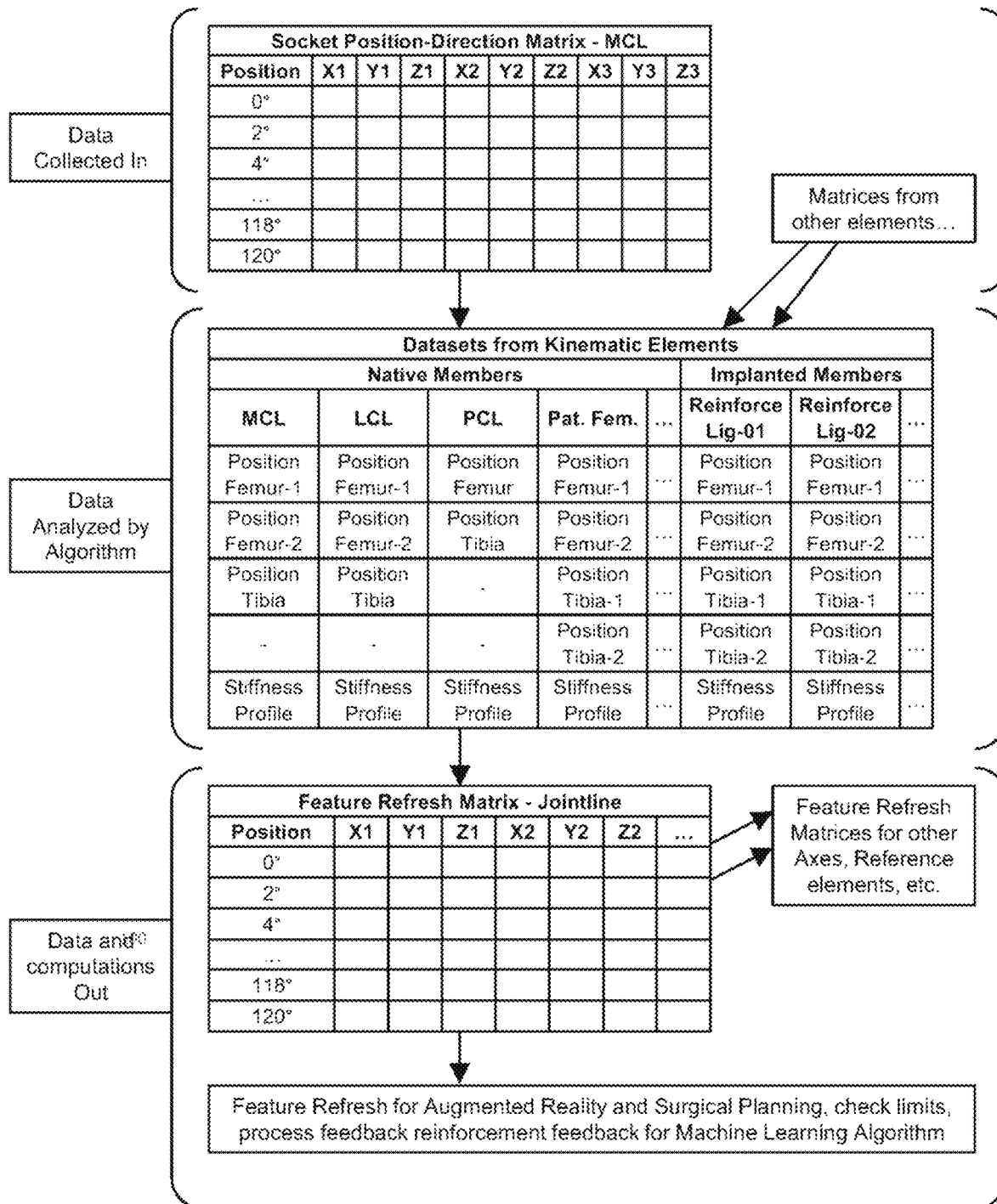
FIG. 56 is a diagram of a software algorithm.

One or more of the methods described herein may be incorporated into a complete surgical flow process. FIG. 55 illustrates an exemplary process as it applies to knee joint J. For purposes of explanation, the pre-operative knee joint J is assumed to have some wear, injury, or disease process and is referred to as a "pathological knee".

At block 2000, optionally pre-operative dynamic imaging may be used to evaluate the overall characteristics of the knee joint J, including for example the range of motion. The body-worn tracking apparatus 600 described above may be used for this purpose.

At block 2002, a software application is used to compute socket locations throughout the range of motion for the pathological knee. At this point, the software application may be used to predict the ligament stiffness and joint kinematics. An operative plan may be proposed or predicted or computed. Socket matrices may be created, this may serve as a seed for machine learning component (if used).

At the block 2004 the software application assigns parameters for patient-specific operative workflow based on the pre-op dynamic imaging.

At block 2006, the surgeon will operatively measure the pathological knee by using the tensioner-balancer 40, tracking marker, and related apparatus described above and sweeping the knee through a range of motion while using the apparatus to collect data. Optionally during this process, ligament stiffness and socket locations may be measured operatively (block 2008). If measured, the socket matrices are updated with real-time information.

At block 2010, if a machine learning component is utilized, the information collected from the patient's knee would be used to reinforce that component.

At block 2012, the software application performs a socket update cycle. Within the cycle performs the following functions (1) augmented reality frame refresh; (2) surgical feature refresh; (3) check limits/constraints.

At block 2014, the software application builds a surgical plan. The surgical plan includes implant positioning and augmentation computation. Fundamentally, the surgical plan embodies an algorithm (block 2017) which takes as input the pre-existing conditions of the pathological knee, the desired end condition (i.e. the repaired knee), and computes one or more corrections necessary to achieve the desired end condition. Nonlimiting examples of required corrections are: implant size selection, implant contact surface/articular surface best curve fit, and soft tissue augmentations.

At block 2016, guided surgical workflow is carried out this could be using augmented reality, robotic guidance, or the like.

Finally, at block 2018 optionally post-operative dynamic imaging may be carried out.

Some or all of the functions of the surgical flow process may be performed by a machine learning system. Numerous types of machine learning software are known in the art which are capable of correlating multiple inputs to multiple outputs without the necessity for manually programming the exact interrelationships of the inputs and the outputs.

In one example, inputs to the machine learning system may be the position of the sockets and the ligament loads and stiffnesses (e.g. stress versus strain curve).

The Machine Learning system may assign and compute a Hierarchy of Ligament Significance to overall knee motion, action, stability, and kinematics. The Machine Learning system may assign and compute tunability sensitivities of various ligaments in the six degrees of motion of the knee to define the kinematic relationship of the tibia to femur. Nonlimiting examples of ligaments include deep and superficial MCL (medical collateral ligament), deep and superficial LCL (lateral collateral ligament), anterolateral ligament, Fibula collateral ligament, popliteal ligament, patella-femoral ligament, lateral patellar retinaculum, both bundles of the ACL and PCL, and menisci of the knee.

The output may be the kinematics of the pathological or native knee joint or the kinematics of the repaired knee joint with prosthetic components included.

Machine learning systems may be provided with initial seed data, and trained with known reinforcement learning (e.g., supervised or semi-supervised) methodologies. Unsupervised learning methods may also be deployed in laboratory settings to explore potential kinematic outcomes rapidly and in bulk (without having to wait many months to study large populations). The machine learning system may incorporate historical populational data to make decisions. Furthermore, patient-specific inputs to the evaluation may be collected digitally over some or all of the lifetime of the patient. The machine learning system may be improved with patient feedback by evaluating qualitatively and quantitatively the postoperative the patient result as a dataset; using the result dataset as an input into a large database; and using the database to develop future procedural pathways and to use as inputs into machine learning-based decisions. Reward functions may be used as inputs to the machine learning system to drive better qualitative and quantitative patient outcomes.

Figure 57:
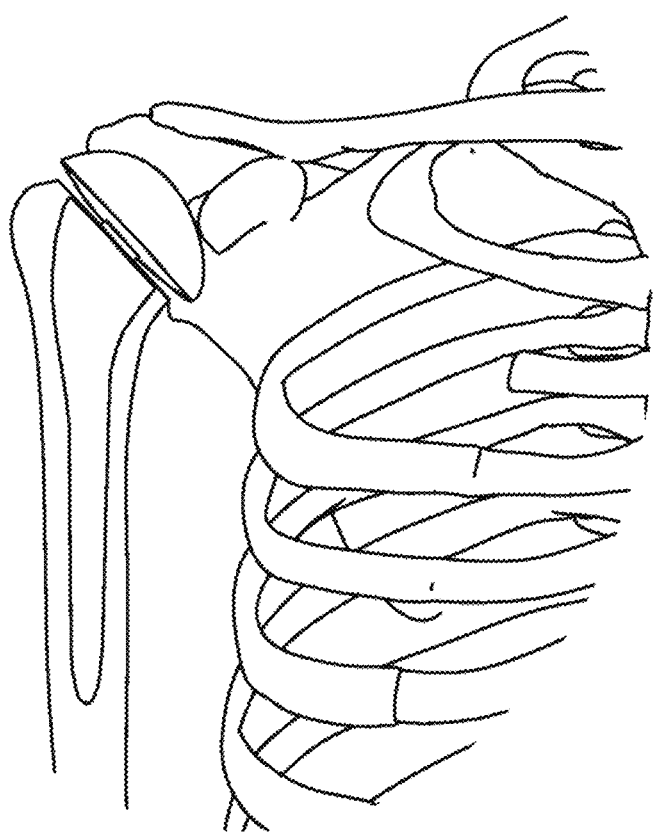
FIG. 57 is a schematic diagram of a human shoulder joint.
Figure 58:
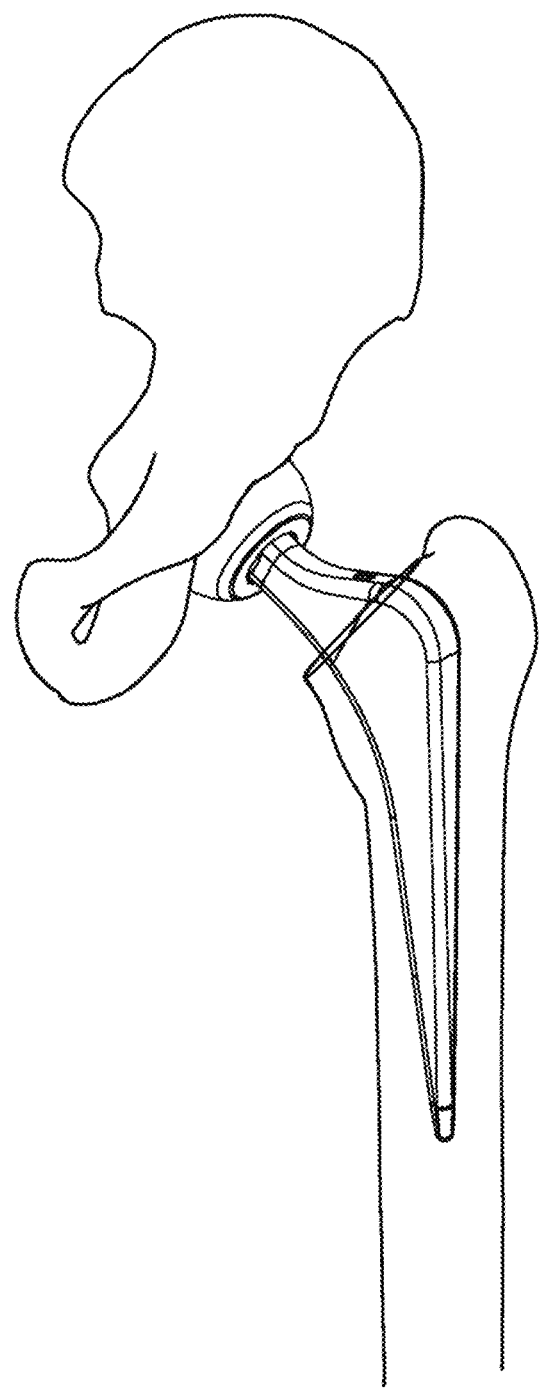
FIG. 58 is a schematic diagram of the human hip joint.

While the methods described herein have been explained using a knee joint as an example, it will be understood that at least some of the methods are applicable to other joints having two or more bones connected together by soft tissue to form and articulating joint. For example, the socket modeling construct could be used to model the soft tissue of a shoulder joint having a scapula and a humerus and associated ligaments and tendons as shown in FIG. 57, or a hip joint having a pelvis and a femur and associated ligaments and tendons as shown in FIG. 58.

The methods and apparatus described herein have numerous advantages. They will permit the repair or reconstruction of the knee joint or other joints with good post-operative results without requiring unusual skill from the surgeon.

The foregoing has described a knee evaluation and arthroplasty method. All of the features disclosed in this specification, and/or all of the steps of any method or process so disclosed, may be combined in any combination, except combinations where at least some of such features and/or steps are mutually exclusive.

Each feature disclosed in this specification may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends, or to any novel one, or any novel combination, of the steps of any method or process so disclosed.

What is claimed is:

1. A method of generating an evaluation of a human joint which includes two or more bones and ligaments, wherein the ligaments are under anatomical tension to connect the bones together, creating a load-bearing articulating joint, the method comprising:

inputting locations of one or more sockets into a software application, each socket representing a ligament attachment point to bone;

interconnecting the one or more sockets with mathematical relationships that describe the kinematic physics of the one or more sockets relative to one another;

providing spatial information to describe the movement of the sockets relative to one another;

defining an initial kinematic state of the joint;

defining a final kinematic state of the joint;

using a software application to compute a difference between the initial and final kinematic states; and using the software application to compute one or more corrections required to achieve the final kinematic state of the joint, wherein the computed corrections constitute an evaluation of the joint; and implementing the computed corrections in a guided surgical workflow on the human joint, the guided surgical workflow including at least one of the following:

positioning an implant in the joint; and augmenting at least one of the ligaments.

2. The method of claim 1, wherein the software application performs a machine learning methodology to carry out the steps of the method.

3. The method of claim 2, wherein the machine learning methodology used is a supervised learning methodology.

4. The method of claim 2, wherein the machine learning methodology used is unsupervised learning.

5. The method of claim 2, wherein the machine learning methodology used is semi-supervised learning.

6. The method of claim 2, wherein the machine learning methodology used is reinforcement learning.

7. The method of claim 2, wherein the machine learning methodology incorporates historical populational data to make decisions.

8. The method of claim 1 wherein the joint is a knee or shoulder or hip or ankle.

9. The method of claim 1, wherein the software application generates a mathematical representation of a ligament or tendon using two or more of the sockets for each ligament or tendon.

10. The method of claim 9, further comprising assigning hierarchies and sensitivities to individual sockets and ligaments.

11. The method of claim 1, wherein each end of a ligament is represented by one or more sockets.

12. The method of claim 1, wherein each socket has a centroid, a position, a magnitude and direction of velocity, and a magnitude and direction of acceleration.

13. The method of claim 1, wherein the evaluation is used to develop a patient-specific operative procedure preoperatively.

14. The method of claim 1, wherein the evaluation is used to develop a patient-specific postoperative plan of care.

15. The method of claim 1, wherein the evaluation is used to develop a patient-specific endoprosthesis.

16. The method of claim 1, wherein the evaluation is used to develop a patient-specific augmentation or replacement or repair of a ligament or a tendon.

17. The method of claim 1, wherein at least one patient-specific input to the evaluation is collected digitally over some or all of a lifetime of the patient.

18. The method of claim 1, wherein the evaluation is used to assign specific kinematics to the individual ligaments of a knee joint.

19. The method of claim 1, wherein the evaluation is used as input to other evaluations.

20. The method of claim 1, wherein a first resection cut is made to one of the two or more bones with a surgical instrument, prior to the step of inputting locations of one or more sockets into the software application.

21. The method of claim 1, wherein outputs of the evaluation instruct and define a prosthesis size and best-fit location to be used.

22. The method of claim 1, further comprising using an apparatus to measure and record physical properties of a knee joint.

23. The method of claim 22 wherein the apparatus includes:

a tensioner-balancer, including:

a baseplate;

a top plate; and a linkage positioned between and interconnecting the baseplate and the top plate and operable to move the top plate relative to the bottom plate between retracted and extended positions in response to application of an actuating force wherein the linkage comprises links operable to move the top plate in an axial direction in response to pivotal/rotary movement of the links in a plane parallel to the axial direction wherein the top plate is pivotally connected to the linkage so as to be able to freely pivot about a single mechanical pivot axis to change its angular orientation relative to the baseplate.

24. The method of claim 1, wherein a digital display is used to portray the evaluated joint.

25. The method of claim 1, wherein a virtual reality display is used to portray the evaluated joint.

* * * * *